US012626305B2

(12) United States Patent
Zahora et al.

(10) Patent No.: US 12,626,305 B2
(45) Date of Patent: May 12, 2026

(54) SYSTEMS AND METHODS FOR PREDICTION AND ESTIMATION OF MEDICAL CLAIMS PAYMENTS

(71) Applicant: ZOLL Medical Corporation, Chelmsford, MA (US)

(72) Inventors: Kevin M. Zahora, Liberty Township, OH (US); Jennifer A. Carlson, Broomfield, CO (US); Charles E. Fuller, III, Westminster, CO (US); Jessica P. Deschane, Thornton, CO (US); Paul D. Canino, Miller Place, NY (US)

(73) Assignee: ZOLL Medical Corporation, Chelmsford, MA (US)

( * ) Notice: Subject to any disclaimer, the term of this patent is extended or adjusted under 35 U.S.C. 154(b) by 191 days.

(21) Appl. No.: 17/704,492

(22) Filed: Mar. 25, 2022

(65) Prior Publication Data

US 2022/0309592 A1     Sep. 29, 2022

Related U.S. Application Data

(60) Provisional application No. 63/166,690, filed on Mar. 26, 2021.

(51) Int. Cl.
*G06Q 40/08* (2012.01)
*G06N 20/00* (2019.01)
(Continued)

(52) U.S. Cl.
CPC ............. *G06Q 40/08* (2013.01); *G06Q 10/10* (2013.01); *G16H 10/60* (2018.01); *G06N 20/00* (2019.01)

(58) Field of Classification Search
USPC ........................................................ 705/2–3
See application file for complete search history.

(56) References Cited

U.S. PATENT DOCUMENTS 7,734,481 B1   6/2010  Hutton et al.
8,566,117 B1  10/2013  Troutt et al.
(Continued)

FOREIGN PATENT DOCUMENTS

WO      2022/006441 A     1/2022

OTHER PUBLICATIONS

Glisan, K. (2015). Reducing call center intake utilizing health insurance company web-based provider tools (Order No. 3715063). Available from ProQuest Dissertations and Theses Professional. (1710455065). Retrieved from https://dialog.proquest.com/professional/docview/1710455065?accountid=131444 (Year: 2015).*
(Continued)

*Primary Examiner* — Bennett Stephen Erickson
(74) *Attorney, Agent, or Firm* — Mintz, Levin, Cohn, Ferris, Glovsky and Popeo, P.C.

(57)          ABSTRACT

Systems and methods for calculating medical claims payment estimates may receive a medical claim for a first patient including billing code(s) and demographic data, apply the demographic data to identify payer(s) for the first patient, access a data universe including patient data collection(s) of patient data records for a second group of patients, payer data collection(s) of data records for payers, and a financial history data collection including financial data record(s) for the first patient, identify, for each billing code, a payer payment pattern based on a combination of the patient data records and payer data record(s) corresponding to the payer for the first patient, identify a patient payment pattern based on the financial data record(s), and apply the payer payment pattern and the patient payment pattern to the medical claim for the first patient to calculate a payment estimation for the medical claim.

36 Claims, 38 Drawing Sheets

(51) Int. Cl.
  *G06Q 10/10* (2023.01)
  *G16H 10/60* (2018.01)

(56) References Cited

U.S. PATENT DOCUMENTS

| | | | | |
|---|---|---|---|---|
| 8,930,216 | B1 * | 1/2015 | Johnson | G06Q 40/03 |
| | | | | 705/2 |
| 10,354,211 | B1 | 7/2019 | Pilkington et al. | |
| 10,410,305 | B1 * | 9/2019 | Pilkington | G06Q 50/22 |
| 10,510,440 | B1 | 12/2019 | Jose | |
| 10,598,508 | B2 | 3/2020 | Gotschall et al. | |
| 10,942,040 | B2 | 3/2021 | Gotschall et al. | |
| 10,970,785 | B2 | 4/2021 | Magnuson et al. | |
| 11,011,256 | B2 | 5/2021 | Dunleavy | |
| 11,114,185 | B1 | 9/2021 | Malec et al. | |
| 11,270,785 | B1 * | 3/2022 | Talvola | G16H 50/30 |
| 11,410,246 | B2 | 8/2022 | Bull | |
| 11,436,304 | B1 * | 9/2022 | Birgenheier | G16H 40/20 |
| 2003/0036926 | A1 | 2/2003 | Starkey et al. | |
| 2004/0133452 | A1 | 7/2004 | Denny et al. | |
| 2006/0041487 | A1 * | 2/2006 | Santalo | G06Q 10/10 |
| | | | | 705/30 |
| 2007/0011030 | A1 | 1/2007 | Bregante et al. | |
| 2007/0011031 | A1 | 1/2007 | Bregante et al. | |
| 2007/0011032 | A1 | 1/2007 | Bregante et al. | |
| 2007/0271119 | A1 | 11/2007 | Boerger et al. | |
| 2008/0195625 | A1 * | 8/2008 | Hargroder | G06Q 40/08 |
| | | | | 707/999.009 |
| 2008/0275737 | A1 | 11/2008 | Gentry et al. | |
| 2010/0063907 | A1 * | 3/2010 | Savani | G06Q 40/12 |
| | | | | 705/30 |
| 2011/0238451 | A1 | 9/2011 | Bazzani et al. | |
| 2012/0259773 | A1 | 10/2012 | Hoffman | |
| 2013/0054259 | A1 * | 2/2013 | Wojtusiak | G06Q 10/10 |
| | | | | 705/2 |
| 2013/0097157 | A1 | 4/2013 | Ng et al. | |
| 2013/0191895 | A1 | 7/2013 | Magee et al. | |
| 2013/0218587 | A1 | 8/2013 | Carter | |
| 2013/0246090 | A1 | 9/2013 | Hoffman et al. | |
| 2013/0262148 | A1 | 10/2013 | Weber et al. | |
| 2014/0046678 | A1 | 2/2014 | Lacy et al. | |
| 2014/0095188 | A1 | 4/2014 | Derer | |
| 2014/0278511 | A1 | 9/2014 | Fielding et al. | |
| 2014/0278525 | A1 | 9/2014 | Curran | |
| 2014/0379363 | A1 | 12/2014 | Hart et al. | |
| 2015/0032466 | A1 * | 1/2015 | Vaze | G06Q 10/10 |
| | | | | 705/2 |
| 2015/0088535 | A1 | 3/2015 | Smith et al. | |
| 2015/0100349 | A1 | 4/2015 | Lacy et al. | |
| 2015/0112711 | A1 * | 4/2015 | Dean | G06Q 40/12 |
| | | | | 705/2 |
| 2015/0127364 | A1 | 5/2015 | Long et al. | |
| 2015/0205846 | A1 | 7/2015 | Aldridge et al. | |
| 2016/0267230 | A1 | 9/2016 | Ochs et al. | |
| 2016/0342750 | A1 | 11/2016 | Alstad et al. | |
| 2017/0308652 | A1 | 10/2017 | Ligon | |
| 2017/0351821 | A1 | 12/2017 | Tanner et al. | |
| 2018/0197160 | A1 | 7/2018 | Hoffman | |
| 2020/0105392 | A1 * | 4/2020 | Karkazis | G16H 50/30 |
| 2020/0311823 | A1 | 10/2020 | D'Abbene et al. | |
| 2021/0295448 | A1 | 9/2021 | McClain et al. | |
| 2021/0304265 | A1 | 9/2021 | Yedlarajaiah et al. | |

OTHER PUBLICATIONS

Nyce, Charles, Predictive Analytics White Paper, American Institute for CPCU/Insurance Institute of America, Oct. 2007.

Accounts Receivable (AR) Solution | ZOLL AR Boost, Uncover More Revenue and Shrink AR by Knowing Your Patients Financially <www.zolldata.com/arboost>.

ZOLL AR Boost: Accounts Receivable Management <www.zolldata.com/accounts receivable-management>.

* cited by examiner

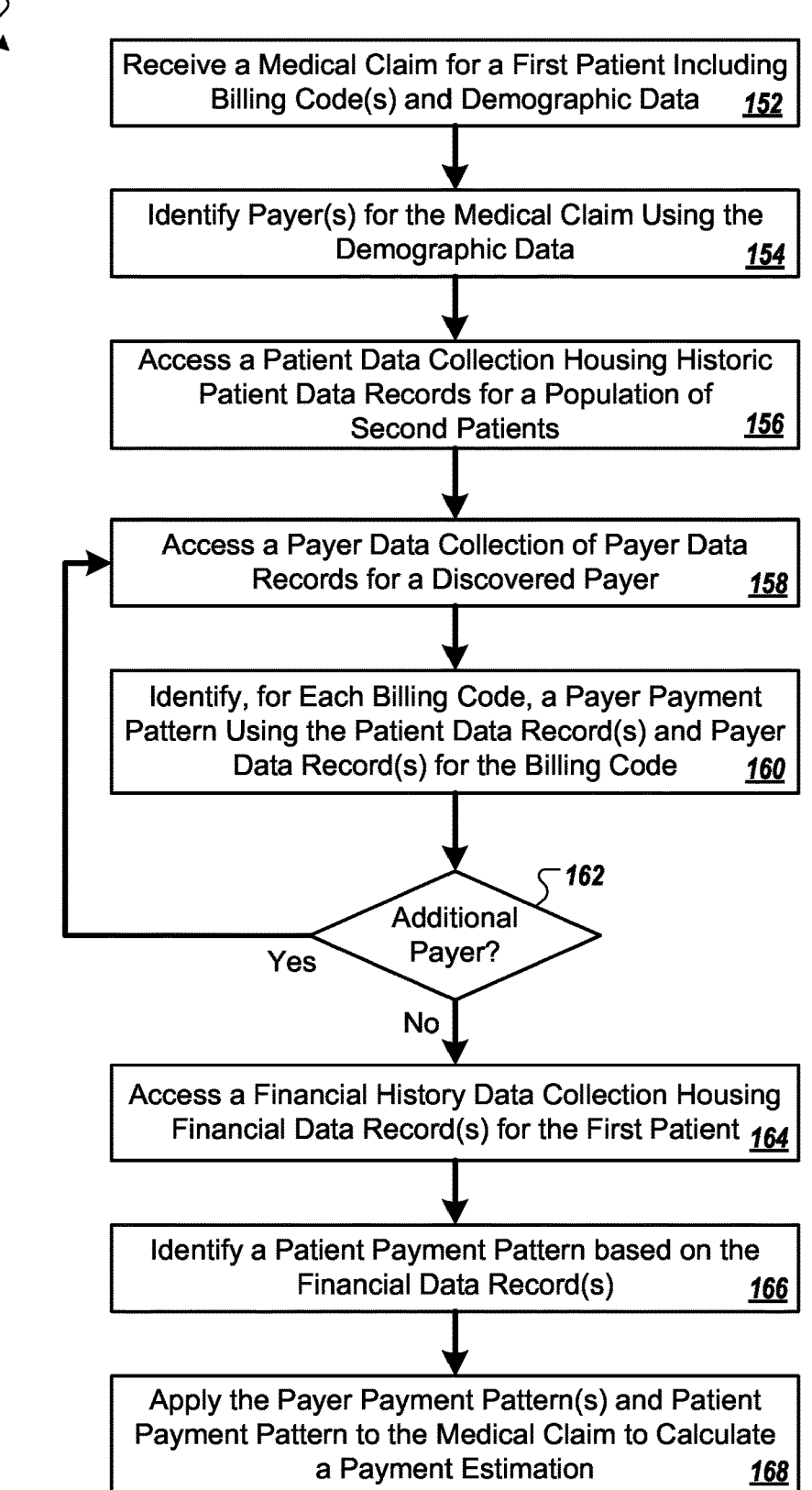

150

Receive a Medical Claim for a First Patient Including Billing Code(s) and Demographic Data     *152*

Identify Payer(s) for the Medical Claim Using the Demographic Data     *154*

Access a Patient Data Collection Housing Historic Patient Data Records for a Population of Second Patients     *156*

Access a Payer Data Collection of Payer Data Records for a Discovered Payer     *158*

Identify, for Each Billing Code, a Payer Payment Pattern Using the Patient Data Record(s) and Payer Data Record(s) for the Billing Code     *160*

*162*
Additional Payer?

Yes

No

Access a Financial History Data Collection Housing Financial Data Record(s) for the First Patient *164*

Identify a Patient Payment Pattern based on the Financial Data Record(s)     *166*

Apply the Payer Payment Pattern(s) and Patient Payment Pattern to the Medical Claim to Calculate a Payment Estimation     *168*

FIG. 1B

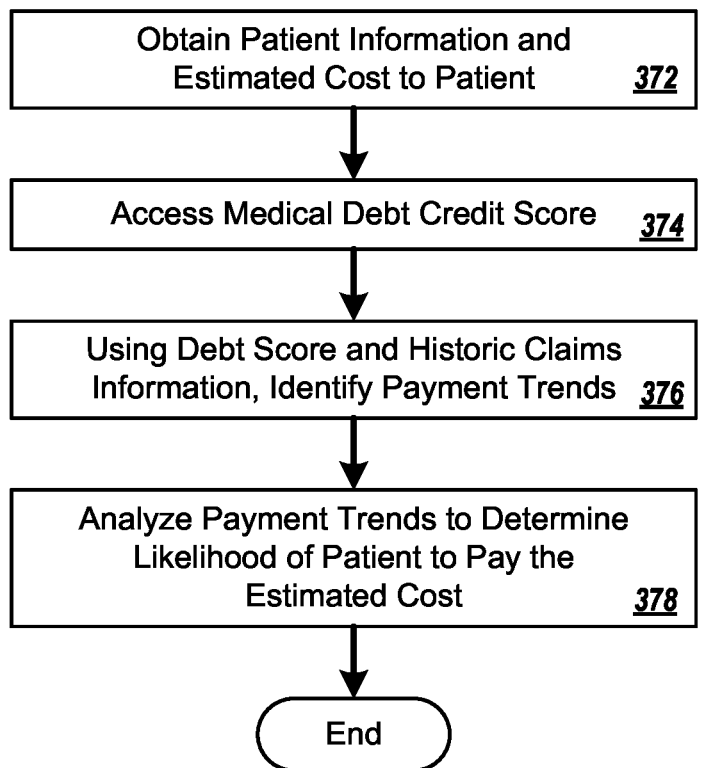
Obtain Patient Information and
Estimated Cost to Patient  _372_
Access Medical Debt Credit Score  _374_
Using Debt Score and Historic Claims
Information, Identify Payment Trends  _376_
Analyze Payment Trends to Determine
Likelihood of Patient to Pay the
Estimated Cost  _378_
End
FIG. 3D

900

Obtain Initial Patient Demographic Data from
a First Data Source          *902*

Analyze Initial Patient
Demographic Data in View of
Identification Criteria          *904*

Compare Initial Patient
Demographic Data to
Known Demographic Data          *906*

Data Insufficient?
*908*

No

Yes

Ambiguity /
Contradiction?
*910*

No

Yes

Use Portion(s) of Initial Patient Demographic Data to Access Additional
Data Source(s) to Supplement Initial Data          *912*

918

Patient Located via
Additional Source(s)?
*914*

No

Flag Data
Warning(s) in
Patient Data

Yes

Use Data from Additional Source(s) to
Supplement Missing Information and/or to
Resolve Ambiguities/Contraditions          *916*

End

Predictive Analytics Platform    *102*

Prescription Approval Analysis Engine *1034*

Estimate Medical Fees for Patient A   *1026*

Prescription Billing Codes *1028*

Patient A Demographic Data *1030*

Payer and payment verification and estimate *1032*

Prescription Services    *1022*

Prescription Requests *1024*

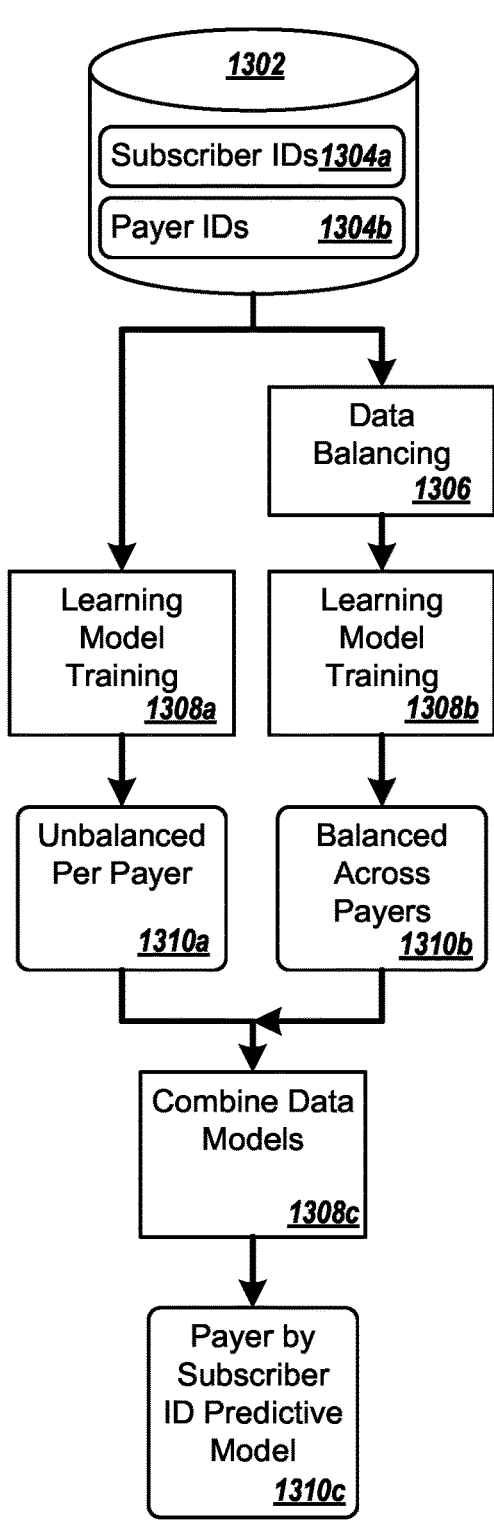
FIG. 13A

1320

1330

1500

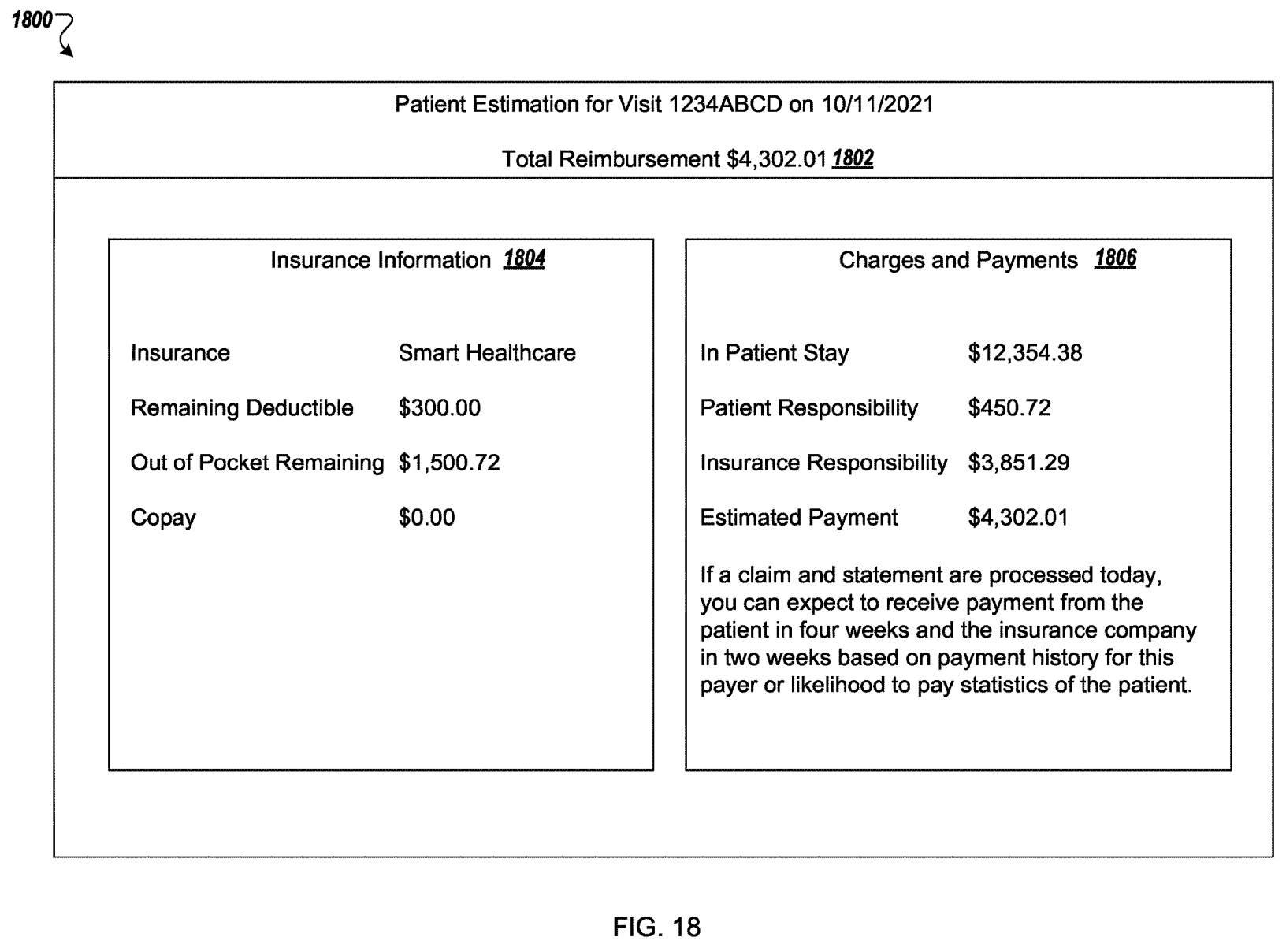

1800

Patient Estimation for Visit 1234ABCD on 10/11/2021

Total Reimbursement $4,302.01 *1802*

Insurance Information *1804*

Insurance                     Smart Healthcare

Remaining Deductible          $300.00

Out of Pocket Remaining       $1,500.72

Copay                         $0.00

Charges and Payments *1806*

In Patient Stay               $12,354.38

Patient Responsibility        $450.72

Insurance Responsibility      $3,851.29

Estimated Payment             $4,302.01

If a claim and statement are processed today, you can expect to receive payment from the patient in four weeks and the insurance company in two weeks based on payment history for this payer or likelihood to pay statistics of the patient.

FIG. 18

SYSTEMS AND METHODS FOR PREDICTION AND ESTIMATION OF MEDICAL CLAIMS PAYMENTS

RELATED APPLICATIONS

This application claims priority to U.S. Provisional Patent Application Ser. No. 63/166,690, entitled "Systems and Methods for Prediction and Estimation of Medical Claims Payments," filed Mar. 26, 2021, the contents thereof being hereby incorporated by reference in its entirety.

BACKGROUND

Payers of health services and products, such as health insurance companies, federal and state health coverage providers including Medicare and Medicaid, and liability insurance companies provide payment coverage to a wide variety of medical providers. The medical providers include traditional brick and mortar service providers such as, in some examples, hospitals, physician practices, emergency rooms, urgent care facilities, and surgical centers. Further, medical providers can include mobile providers such as emergency medical services (EMS) providers, ambulance companies, and medical evacuation providers. Medical providers can include specialty care providers such as dental care providers, chiropractors, and physical therapists. Further, medical providers include prescription medical device companies such as contact lens retailers, wheelchair companies, and prosthetic device manufacturers. As technological solutions expand, more and more wearable prescription medical device companies are included within the span of health product coverage, including, in some examples, wearable glucose monitors, wearable nerve stimulation devices, and the ZOLL LifeVest® wearable cardioverter defibrillator. Each of the medical providers seek reimbursement from payers for services and products provided to patients, and each of the medical providers maintains records related to patients and payer remittance.

Rather than submitting reimbursement directly to each medical provider, payers are often billed via a billing company or a medical provider administration platform used by the medical provider for managing the claims and patient invoicing. The billing company or medical provider administration platform, for example, may streamline the complexities of claims processing and records keeping on behalf of the medical provider.

Medical claims submission and processing involves many complex steps to move from initiating claims preparation to receiving payment and involves numerous entities and databases. Claim verification, for example, oftentimes involves confirmation of patient information as well as payer information. In another example, determining the correct billing amount can involve numerous factors, such as patient co-pay amount, patient deductible, multiple insurers and/or liability insurance, and location where the medical services were rendered.

SUMMARY OF ILLUSTRATIVE EMBODIMENTS

In one aspect, the present disclosure relates to a system for calculating medical claims payment estimates, the system including a payment pattern application engine including hardware logic and/or software logic configured to receive a medical claim for a first patient, the medical claim including at least one billing code and at least one item of demographic data for the first patient, and apply the at least one item of demographic data for the first patient to identify at least one payer of a number of payers for the first patient. The system may include a payment pattern identification engine including hardware logic and/or software logic configured to access data collections including at least one patient data collection including a number of patient data records for a number of second patients, at least one payer data collection including a number of payer data records for the number of payers, and a financial history data collection including at least one financial data record for the first patient, identify, for each billing code of the at least one billing code, a payer payment pattern for the respective billing code based on a combination of the number of patient data records and at least one payer data record of a portion of the number of payer data records corresponding to the at least one payer for the first patient, and identify a patient payment pattern based on the at least one financial data record. The payment pattern application engine may be further configured to apply the payer payment pattern and the patient payment pattern to the medical claim for the first patient to calculate a payment estimation for the medical claim.

In some embodiments, identifying the at least one payer includes automatically verifying, with an external computing system of the payer via a network, active coverage of the first patient. Automatically verifying the active coverage of the first patient may include locating a first plan for the first patient based on the at least one item of demographic data of the patient, the first plan including additional demographic data for the patient, identifying the first plan as an inactive plan, locating a second plan based on the additional demographic data for the first patient, and automatically verifying the second plan as the active coverage of the first patient.

In some embodiments, the payer is associated with a number of payer plans, the payment pattern application engine is further configured to determine an active plan of the number of payer plans for the first patient, and identifying the payer payment pattern includes identifying the payer payment pattern for the active plan.

In some embodiments, identifying the at least one payer includes identifying two or more payers, and ranking the two or more payers in order of preference. Ranking the two or more payers may include ranking at least in part based on the at least one billing code.

In some embodiments, identifying the at least one payer includes identifying at least one most likely payer of the number of payers based on at least a portion of the demographic data of the first patient, and contacting an external computing system of each payer of the at least one most likely payer, via a network, to query existence of active coverage of the first patient with the respective payer. The portion of the demographic data may include a geographic region associated with the at least the portion of the demographic data. Identifying the at least one most likely payer may include identifying the at least one most likely payer based on an association of the at least one most likely payer with the geographic region.

In some embodiments, identifying the payer payment pattern for the respective billing code includes identifying, in the portion of the number of payer data records, remittance data for each billing code of the at least one billing code, and calculating, using the remittance data, a remittance estimate. Identifying the payer payment pattern for the respective billing code may include calculating a confidence in similarity of the remittance estimate to an actual future remittance value. Calculating the confidence level may include adjusting the confidence level based at least in part on one or more dates corresponding to the remittance data, where a higher confidence level is associated with a more recent date to a date of the medical claim. Calculating the confidence level may include determining, using at least one machine learning classifier, at least one similarity metric between remittance rates from a prior year and remittance rates from a present year. The payer may be associated with a number of payer plans, and calculating the confidence level may include adjusting the confidence level based at least in part on a similarity between one or more plans corresponding to the remittance data and an active plan of the first patient.

In some embodiments, identifying the patient payment pattern includes matching a credit score of the first patient to a credit score range of a portion of the number of second patients. The credit score may be a medical debt credit score. Matching the credit score may include analyzing, using at least one machine learning classifier, payment trends of the number of second patients to determine the credit score range including the credit score of the first patient.

In some embodiments, identifying the patient payment pattern includes matching a portion of the demographic data of the first patient to demographic data of one or more second patients of the number of second patients.

In some embodiments, calculating the payment estimation includes applying at least one deductible amount corresponding to a deductible level of an active payer plan of first patient. Calculating the payment estimation may include automatically determining a first deductible amount of the at least one deductible amount by contacting an external computing system of the payer via a network to request a current balance of a remaining maximum deductible.

In some embodiments, identifying the at least one payer includes determining, for each billing code of the at least one billing code, a pre-authorization status corresponding to the respective billing code. Determining the pre-authorization status may include analyzing at least a portion of i) the number of payer data records and/or ii) the number of patient data records using the respective billing code to identify evidence of authorization requests from one or more of the number of second patients. Analyzing the i) the number of payer data records and/or ii) the number of patient data records may include determining a historic pattern of coverage declinations associated with the respective billing code indicative of likelihood of a pre-authorization requirement by the payer. The portion of i) the number of payer data records and/or ii) the number of patient data records may be analyzed further using an active payer plan of the first patient. The system may include a pre-approval authorization engine including hardware and/or software logic configured to initiate an authorization request submission with a first payer of the at least one payer on behalf of the first patient. Determining the pre-authorization status may include automatically issuing, to an external computing system of the payer via a network, a request to determine authorization status of a service corresponding to the respective billing code on behalf of the first patient.

In some embodiments, identifying the at least one payer includes identifying a liability payer of the at least one payer for the first patient. The payment pattern application engine may be further configured to determine, for each billing code of the at least one billing code, a likelihood of applicability to liability coverage. Determining the likelihood of applicability to liability coverage may include determining, using at least one machine learning classifier, a match between one or more billing codes of the at least one billing code and a historic pattern for remittance by one or more payers of a number of liability payers including the liability payer. Determining the likelihood of applicability to liability coverage may include analyzing the medical claim to identify one or more key words and/or phrases associated with liability coverage. Identifying the liability payer may include locating liability coverage using employment information of the first patient. Identifying the liability payer may include locating liability coverage using employment information of a guarantor associated with the first patient. Identifying the liability payer may include identifying, using at least one patient data record of the first patient, the guarantor. Calculating the payment estimation for the medical claim may include determining coverage coordination between the liability payer and a primary payer of the at least one payer.

In some embodiments, the payment pattern application engine is configured to identify eligibility for one or more medical payment assistance programs based on the at least one item of demographic data for the first patient. The payment pattern application engine may be configured to locate patient income based on the at least one item of demographic data for the first patient and identify the patient income as below a medical payment assistance program eligibility criterion. The payment pattern application engine may be configured to estimate a supplemental reimbursement from the medical payment assistance program. The payment pattern application engine may be configured to initiate enrollment of the first patient in the one or more medical payment assistance programs.

In some embodiments, the system includes a projected revenue analysis engine including hardware logic and/or software logic configured to analyze the number of payer data records to identify a set of payment trends across the number of payers. The projected revenue analysis engine may be configured to analyze a number of open claims including the medical claim and a corresponding number of payment estimations including the payment estimation to forecast projected revenue for a future time period. The projected revenue analysis engine may be configured to forecast the projected revenue for a number of future revenue cycles. The projected revenue analysis engine may be configured to analyze the number of payer data records to identify trends in length of time between claim submission and payer remittance for each payer of the number of payers. Identifying the trends in length of time between claims submission and payer remittance may include applying, for each payer of the number of payers, at least one machine learning classifier to a portion of the number of payer data records corresponding to the respective payer. The projected revenue analysis engine may be configured to analyze the number of payer data records to identify trends in payer remittance across a number of billing codes. The projected revenue analysis engine may be configured to apply the trends in payer remittance to billing codes associated with a number of open claims to forecast projected revenue for a future time period. Identifying the trends in payer remittance across the number of billing codes may include applying, for each payer of the number of payers, at least one machine learning classifier to a portion of the number of payer data records corresponding to the respective payer across the number of billing codes. The number of billing codes may be sorted into a set of billing code categories and identifying the trends in payer remittance across the number of billing codes may include identifying the trends in payer remittance for each billing category of the set of billing code categories. The projected revenue analysis engine may be configured to apply the trends in payer remittance to a number of projected billing codes to forecast projected revenue for a future time period. The projected revenue analysis engine may be configured to determine a number of projected billing codes at least in part through analyzing a number of historic claims. The projected revenue analysis engine may be configured to calculate a number of projected metrics related to the set of payment trends. The projected revenue analysis engine may be configured to generate, using the number of projected metrics, a revenue forecast report.

In some embodiments, the system includes a procedure trends analysis engine including hardware logic and/or software logic configured to analyze a number of historic claims related to the number of second patients to identify a number of sets of commonly paired procedures, where claim submission of a first procedure of the number of sets of commonly paired procedures precedes claim submission of a second procedure of the number of sets of commonly paired procedures by up to a threshold period of time, and for each set of commonly paired procedures, identifying includes determining that the first procedure is followed by the second procedure for at least a threshold percentage of a portion of the number of historic claims including the first procedure. The procedure trends analysis engine may be further configured to identify, within the number of sets of commonly paired procedures, a likelihood of the second procedure following the first procedure based on a set of demographic groups. The set of demographic groups may be one of age range, gender, body mass index range, or co-morbidity. The procedure trends analysis engine may be configured to apply the sets of commonly paired procedures to a number of recently filed claims to predict one or more projected additional claims involving the second procedure of one or more sets of the number of sets of commonly paired procedures. Predicting the one or more projected additional claims may include predicting a time period of the second procedure of the one or more sets. Predicting the one or more projected additional claims may include determining, based on the one or more projected additional claims, at least one projected remittance value. Determining the at least one projected remittance value may include determining a respective projected remittance value for each of two or more revenue cycles.

In some embodiments, the payment pattern application engine is configured to analyze the at least one item of demographic data in view of identification criteria to confirm sufficiency of provided information. Upon determining insufficiency of the provided information, the payment pattern application engine may be configured to locate patient information regarding the first patient in at least one additional data source to supplement the at least one item of demographic data.

In some embodiments, the payment pattern application engine is configured to identify at least one of a contradiction or an ambiguity in patient information by comparing the at least one item of demographic data to known demographic data for the first patient. Upon identifying one or more contradictions or ambiguities, the payment pattern application engine may be configured to locate patient information regarding the first patient in at least one additional data source resolve the one or more contradictions or ambiguities in the at least one item of demographic data.

In some embodiments, the medical claim includes a pre-service estimate for medical services and the payment pattern application engine is configured to calculate a payment estimation and confidence score for the pre-service estimate for the medical services. The medical services may include at least one of medical transport and a prescription. The payment pattern application engine may be configured to service an interactive user interface. The interactive user interface may include a medical transport scheduling and dispatch service. The interactive user interface may include a claims preparation service configured to automatically flag incorrect or inconsistent demographics information. The payment pattern application engine may be configured to calculate a payment estimation and confidence score for one or more candidate medical procedure codes. The payment pattern application engine may be configured to provide alternative or preferred medical procedure codes based on the calculated payment estimations. The payment pattern application engine may be configured to track payments of third-party providers, provide calculated payment estimations for a number of claim submission dates based on the third-party provider payments, and provide a recommended claim submission date based on the calculated payment estimation and the tracked payments of the third-party providers. The payment pattern application engine may be configured to calculate payment estimations and confidence scores and provide a recommended patient pre-payment amount based on the calculated payment estimations and confidence scores.

In some embodiments, the payment pattern application engine is communicatively coupled with a computer-aided dispatch (CAD) and configured to receive initial patient demographics for a patient from the CAD, identify supplemental patient demographics based on the initial patient demographics, identify insurance coverages for the patient based on the supplemental patient demographics, and provide the supplemental patient demographics and the insurance coverages to the CAD. The payment pattern application engine may be communicatively coupled to an electronic patient care record (ePCR) application and configured to provide the supplemental patient demographics and insurance coverages to the ePCR application. The payment pattern application engine may be configured to receive a patient medical condition from the CAD, calculate payment estimations based on the patient medical condition and the identified insurance coverages, and provide the payment estimations to one or more of the CAD and the ePCR. The payment pattern application engine may be configured to provide one or more of a recommended transport destination and medical procedure codes based on the payment estimations and identified insurance coverages. The payment pattern application engine may be configured to receive updated medical condition information from the ePCR application, update the payment estimations based on the updated medical condition information, and provide the updated payment estimations to the ePCR application. The CAD may be configured to store at least one of the supplemental patient demographics and the identified insurance coverages for the patient and access the stored information for subsequent EMS services provided for the patient.

In one aspect, the present disclosure relates to a system for calculating medical claims payment estimates, the system including a payment pattern application engine including hardware logic and/or software logic configured to receive a medical claim for a first patient, the medical claim including at least one billing code and at least one item of demographic data for the first patient, and apply the at least one item of demographic data for the first patient to identify at least one payer of a number of payers for the first patient, and a payment pattern identification engine including hardware logic and/or software logic configured to access a number of data collections including at least one patient data collection including a number of patient data records for a number of second patients, at least one payer data collection including a number of payer data records for the number of payers, and a financial history data collection including at least one financial data record for the first patient, identify, for each billing code of the at least one billing code, a payer payment pattern for the respective billing code based on a combination of the number of patient data records and at least one payer data record of a portion of the number of payer data records corresponding to the at least one payer for the first patient, and identify a patient payment pattern based on the at least one financial data record. The payment pattern application engine may be configured to apply the payer payment pattern and the patient payment pattern to the medical claim for the first patient to calculate a payment estimation for the medical claim.

In some embodiments, identifying the at least one payer includes automatically verifying, with an external computing system of the payer via a network, active coverage of the first patient. Automatically verifying the active coverage of the first patient may include locating a first plan for the first patient based on the at least one item of demographic data of the patient, the first plan including additional demographic data for the patient, identifying the first plan as an inactive plan, locating a second plan based on the additional demographic data for the first patient, and automatically verifying the second plan as the active coverage of the first patient. The payer may be associated with a number of payer plans, the payment pattern application engine may be further configured to determine an active plan of the number of payer plans for the first patient and identifying the payer payment pattern includes identifying the payer payment pattern for the active plan.

In some embodiments, identifying the at least one payer includes identifying two or more payers, and ranking the two or more payers in order of preference. Ranking the two or more payers may include ranking at least in part based on the at least one billing code.

In some embodiments, identifying the at least one payer includes identifying at least one most likely payer of the number of payers based on at least a portion of the demographic data of the first patient, and contacting an external computing system of each payer of the at least one most likely payer, via a network, to query existence of active coverage of the first patient with the respective payer. The portion of the demographic data may include a geographic region associated with the at least the portion of the demographic data and identifying the at least one most likely payer may include identifying the at least one most likely payer based on an association of the at least one most likely payer with the geographic region.

In some embodiments, identifying the payer payment pattern for the respective billing code includes identifying, in the portion of the number of payer data records, remittance data for each billing code of the at least one billing code, and calculating, using the remittance data, a remittance estimate. Identifying the payer payment pattern for the respective billing code may include calculating a confidence in similarity of the remittance estimate to an actual future remittance value. Calculating the confidence level may include adjusting the confidence level based at least in part on one or more dates corresponding to the remittance data, where a higher confidence level is associated with a more recent date to a date of the medical claim. Calculating the confidence level may include determining, using at least one machine learning classifier, at least one similarity metric between remittance rates from a prior year and remittance rates from a present year. The payer may be associated with a number of payer plans, and calculating the confidence level may include adjusting the confidence level based at least in part on a similarity between one or more plans corresponding to the remittance data and an active plan of the first patient.

In some embodiments, identifying the patient payment pattern includes matching a credit score of the first patient to a credit score range of a portion of the number of second patients. The credit score may be a medical debt credit score. Matching the credit score may include analyzing, using at least one machine learning classifier, payment trends of the number of second patients to determine the credit score range including the credit score of the first patient.

In some embodiments, identifying the patient payment pattern includes identifying correspondence between a portion of the demographic data of the first patient and demographic data of one or more second patients of the number of second patients. Calculating the payment estimation may include applying at least one deductible amount corresponding to a deductible level of an active payer plan of first patient. Calculating the payment estimation may include automatically determining a first deductible amount of the at least one deductible amount by contacting an external computing system of the payer via a network to request a current balance of a remaining maximum deductible.

In some embodiments, identifying the at least one payer includes determining, for each billing code of the at least one billing code, a pre-authorization status corresponding to the respective billing code. Determining the pre-authorization status may include analyzing at least a portion of i) the number of payer data records and/or ii) the number of patient data records using the respective billing code to identify evidence of authorization requests from one or more of the number of second patients. Analyzing the i) the number of payer data records and/or ii) the number of patient data records includes determining a historic pattern of coverage declinations associated with the respective billing code indicative of likelihood of a pre-authorization requirement by the payer. The portion of i) the number of payer data records and/or ii) the number of patient data records may be analyzed further using an active payer plan of the first patient. The system may include a pre-approval authorization engine including hardware and/or software logic configured to initiate an authorization request submission with a first payer of the at least one payer on behalf of the first patient. Determining the pre-authorization status may include automatically issuing, to an external computing system of the payer via a network, a request to determine authorization status of a service corresponding to the respective billing code on behalf of the first patient.

In some embodiments, identifying the at least one payer includes identifying a liability payer of the at least one payer for the first patient. The payment pattern application engine may be configured to determine, for each billing code of the at least one billing code, a likelihood of applicability to liability coverage. Determining the likelihood of applicability to liability coverage may include determining, using at least one machine learning classifier, a correlation between one or more billing codes of the at least one billing code and a historic pattern for remittance by one or more payers of a number of liability payers including the liability payer. Determining the likelihood of applicability to liability coverage may include analyzing the medical claim to identify one or more key words and/or phrases associated with liability coverage. Identifying the liability payer may include locating liability coverage using employment information of the first patient. Identifying the liability payer may include locating liability coverage using employment information of a guarantor associated with the first patient. Identifying the liability payer may include identifying, using at least one patient data record of the first patient, the guarantor. Calculating the payment estimation for the medical claim may include determining coverage coordination between the liability payer and a primary payer of the at least one payer.

In some embodiments, the payment pattern application engine is configured to identify eligibility for one or more medical payment assistance programs based on the at least one item of demographic data for the first patient. The payment pattern application engine may be configured to locate patient income based on the at least one item of demographic data for the first patient and identify the patient income as below a medical payment assistance program eligibility criterion. The payment pattern application engine may be configured to estimate a supplemental reimbursement from the medical payment assistance program. The payment pattern application engine may be configured to initiate enrollment of the first patient in the one or more medical payment assistance programs.

In some embodiments, the system includes a projected revenue analysis engine including hardware logic and/or software logic configured to analyze the number of payer data records to identify a set of payment trends across the number of payers. The projected revenue analysis engine may be configured to analyze a number of open claims including the medical claim and a corresponding number of payment estimations including the payment estimation to forecast projected revenue for a future time period. The projected revenue analysis engine may be configured to forecast the projected revenue for a number of future revenue cycles. The projected revenue analysis engine may be configured to analyze the number of payer data records to identify trends in length of time between claim submission and payer remittance for each payer of the number of payers. Identifying the trends in length of time between claims submission and payer remittance includes applying, for each payer of the number of payers, at least one machine learning classifier to a portion of the number of payer data records corresponding to the respective payer. The projected revenue analysis engine may be configured to analyze the number of payer data records to identify trends in payer remittance across a number of billing codes. The projected revenue analysis engine may be configured to apply the trends in payer remittance to billing codes associated with a number of open claims to forecast projected revenue for a future time period. Identifying the trends in payer remittance across the number of billing codes may include applying, for each payer of the number of payers, at least one machine learning classifier to a portion of the number of payer data records corresponding to the respective payer across the number of billing codes. The number of billing codes may be sorted into a set of billing code categories and identifying the trends in payer remittance across the number of billing codes may include identifying the trends in payer remittance for each billing category of the set of billing code categories. The projected revenue analysis engine may be configured to apply the trends in payer remittance to a number of projected billing codes to forecast projected revenue for a future time period. The projected revenue analysis engine may be configured to determine a number of projected billing codes at least in part through analyzing a number of historic claims. The projected revenue analysis engine may be configured to calculate a number of projected metrics related to the set of payment trends. The projected revenue analysis engine may be configured to generate, using the number of projected metrics, a revenue forecast report.

In some embodiments, the system includes a procedure trends analysis engine including hardware logic and/or software logic configured to analyze a number of historic claims related to the number of second patients to identify a number of sets of commonly paired procedures, where claim submission of a first procedure of the number of sets of commonly paired procedures precedes claim submission of a second procedure of the number of sets of commonly paired procedures by up to a threshold period of time, and for each set of commonly paired procedures, identifying includes determining that the first procedure is followed by the second procedure for at least a threshold percentage of a portion of the number of historic claims including the first procedure. The procedure trends analysis engine may be configured to identify, within the number of sets of commonly paired procedures, a likelihood of the second procedure following the first procedure based on a set of demographic groups. The set of demographic groups may be one of age range, gender, body mass index range, or co-morbidity. The procedure trends analysis engine may be configured to apply the sets of commonly paired procedures to a number of recently filed claims to predict one or more projected additional claims involving the second procedure of one or more sets of the number of sets of commonly paired procedures. Predicting the one or more projected additional claims may include predicting a time period of the second procedure of the one or more sets. Predicting the one or more projected additional claims may include determining, based on the one or more projected additional claims, at least one projected remittance value. Determining the at least one projected remittance value may include determining a respective projected remittance value for each of two or more revenue cycles.

In some embodiments, the payment pattern application engine is configured to analyze the at least one item of demographic data in view of identification criteria to confirm sufficiency of provided information. Upon determining insufficiency of the provided information, the payment pattern application engine may be configured to locate patient information regarding the first patient in at least one additional data source to supplement the at least one item of demographic data. The payment pattern application engine may be configured to identify at least one of a contradiction or an ambiguity in patient information by comparing the at least one item of demographic data to known demographic data for the first patient. Upon identifying one or more contradictions or ambiguities, the payment pattern application engine may be configured to locate patient information regarding the first patient in at least one additional data source resolve the one or more contradictions or ambiguities in the at least one item of demographic data.

In some embodiments, the medical claim includes a pre-service estimate for medical services and the payment pattern application engine is configured to calculate a payment estimation and confidence score for the pre-service estimate for the medical services. The medical services may include at least one of medical transport and a prescription.

In some embodiments, the payment pattern application engine is configured to service an interactive user interface. The interactive user interface may include a medical transport scheduling and dispatch service. The interactive user interface may include a claims preparation service configured to automatically flag incorrect or inconsistent demographics information, and the payment pattern application engine may be configured to calculate a payment estimation and confidence score for one or more candidate medical procedure codes. The payment pattern application engine may be configured to provide alternative or preferred medical procedure codes based on the calculated payment estimations. The payment pattern application engine may be configured to track payments of third-party providers, provide calculated payment estimations for a number of claim submission dates based on the third-party provider payments, and provide a recommended claim submission date based on the calculated payment estimation and the tracked payments of the third-party providers. The payment pattern application engine may be configured to calculate payment estimations and confidence scores and provide a recommended patient pre-payment amount based on the calculated payment estimations and confidence scores.

In some embodiments, the payment pattern application engine is communicatively coupled with one or more of a computer-aided dispatch (CAD) and an electronic patient care record (ePCR) application hosted by an ePCR system and configured to receive initial patient demographics for a patient from the CAD and/or the ePCR application, identify supplemental patient demographics based on the initial patient demographics, identify insurance coverages for the patient based on the supplemental patient demographics, and provide the supplemental patient demographics and the insurance coverages to the CAD and/or the ePCR application. The payment pattern application engine may be configured to receive the initial patient demographics for the patient from the CAD and is configured to provide the supplemental patient demographics and insurance coverages to the ePCR application. The payment pattern application engine may be configured to receive a patient medical condition from the CAD and/or the ePCR application, calculate payment estimations based on the patient medical condition and the identified insurance coverages, and provide the payment estimations to one or more of the CAD and the ePCR. The payment pattern application engine may be configured to provide one or more of a recommended transport destination and medical procedure codes based on the payment estimations and identified insurance coverages. The payment pattern application engine may be configured to provide one or more of the supplemental patient demographics, identified insurance coverages, and payment estimations to the recommended transport destination. The payment pattern application engine may be configured to receive updated medical condition information from the ePCR application, update the payment estimations based on the updated medical condition information, and provide the updated payment estimations to the ePCR application. The CAD and/or an ePCR system hosting the ePCR application may be configured to store at least one of the supplemental patient demographics and the identified insurance coverages for the patient and access the stored information for a subsequent EMS services provided for the patient.

In some embodiments, the at least one billing code identifies a prescription product, and the system includes a prescription approval analysis engine including hardware logic and/or software logic configured to, for each billing code of the at least one billing code identify a payer approval pattern for the respective billing code based on the number of patient data records and the at least one payer data record, and responsive to the payer approval pattern indicating a propensity for denial of the respective billing code, identify at least one reason or justification correlated to approval of the respective billing code by the payer. The prescription approval analysis engine may be configured to generate suggested language applicable to the at least one reason or justification. The prescription product may be a medical device. The at least one reason or justification may be identified based on patient data records corresponding to approvals of the respective billing code within a past year.

In some embodiments, the at least one billing code identifies a medical transport service and calculating the payment estimation includes estimating payment for transporting the patient. The at least one billing code may identify a service for providing during transit. Receiving the medical claim for the first patient may include receiving, from a medical transport scheduling and dispatch system, a number of medical claims for a number of patients for scheduling future medical transport services. The medical transport scheduling and dispatch system may distribute transport requests to a number of transport providers based in part on respective payment estimations for each of the number of patients.

In one aspect, the present disclosure relates to a system for enhancing claims processing and patient admission processing using machine learning based data analytics, the system including a data collection stored to least one non-volatile computer readable medium, the data collection including a number of payer records corresponding to a number of payers, a number of patient records corresponding to a number of individuals each insured by one or more respective payers of the number of payers, and a number of claims records corresponding to a number of previously submitted insurance claims, and software logic configured for execution via processing circuitry and/or hardware logic, the software logic and/or hardware logic being configured to perform operations of a predictive analytics system. The operations may include obtaining patient information of an individual and one or more billing codes corresponding to one or more medical services for the individual, determining at least one payer for the one or more billing codes, determining, based on the at least one payer, a current deductible amount for the individual, calculating, based on at least a portion of the number of patient records related to the at least one payer, an estimated coverage amount by the at least one payer, applying the estimated coverage amount and the current deductible to a cost of the one or more medical services to calculate an estimated balance corresponding to the patient, determining, based at least in part on the current deductible amount, the estimated coverage amount, and the estimated balance, a recommended action related to obtaining remittance for the one or more medical services, where the recommended action includes one or more of a recommended timing for claim submission and a recommended pre-payment amount for the individual, and preparing, for presentation to at a display, a recommendation interface including identification of the payer, identification of the patient, identification of a service provider for performing the one or more medical services, and the recommended action.

In some embodiments, the data collection includes a number of patient financial records, and determining the recommended action includes determining the recommended pre-payment amount by identifying a patient payment pattern based on a portion of the number of patient financial records, applying the patient payment pattern to estimate a patient likelihood to pay, and calculating the recommended pre-payment amount based in part on the patient likelihood to pay. Identifying the patient payment pattern may include matching a credit score of the individual to a credit score range of a portion of the number of patients. The credit score may be a medical debt credit score. Matching the credit score may include analyzing, using at least one machine learning classifier, payment trends of the number of second patients to determine the credit score range including the credit score of the first patient. Identifying the patient payment pattern may include identifying correspondence between a portion of the patient information of the individual and demographic data of one or more patients of the number of patients.

In some embodiments, the data collection includes a number of patient financial records, and determining the recommended action includes determining the recommended pre-payment amount by identifying, through a subject financial record of the number of patient financial records corresponding to the individual, one or more sources of immediate funds for prepayment of at least a portion of the one or more medical services. The operations may include identifying eligibility of the individual for one or more medical payment assistance programs based on the patient information. The operations may include locating an income of the individual based on the patient information of the individual and identifying the income as below a medical payment assistance program eligibility criterion. The operations may include estimating a supplemental reimbursement from the one or more medical payment assistance programs. The operations may include initiating enrollment of the individual in the one or more medical payment assistance programs.

In some embodiments, the at least one payer includes two or more payers, the data collection includes a number of remittance records, where at least a portion of the number of remittance records correspond to a first payer of the at least one payer, and determining the recommended action includes determining the recommended timing of claim submission by estimating, based on the portion of the number of remittance records, a likely timing of reimbursement by the first payer, and recommending submission of a residual balance to a next payer of the two or more payers after the likely timing of reimbursement. Calculating the estimated coverage amount may include determining coverage coordination between a liability payer of the two or more payers and a primary payer of the two or more payers.

In some embodiments, calculating the estimated coverage amount includes applying, for each billing code of the one or more billing codes, one or more machine learning classifiers to determine a payer payment pattern for the respective billing code based on the number of patient records and the at least one payer record, where the machine learning classifier was trained using at least the portion of the number of patient records related to the at least one payer. Determining the at least one payer may include, based on the patient information, automatically identifying, using a subject patient record of the number of patient records corresponding to the individual, the at least one payer. The operations may include automatically confirming, using the subject record and/or at least one payer record of the number of payer records corresponding to the at least one payer, active coverage of the individual by the at least one payer. Determining the deductible amount may include contacting an external computing system of the payer via a network to request a current balance of a remaining maximum deductible.

In some embodiments, identifying the at least one payer includes identifying two or more payers, and ranking the two or more payers in order of preference. Ranking the two or more payers may include ranking at least in part based on the at least one billing code.

In some embodiments, identifying the at least one payer includes identifying at least one most likely payer of the number of payers based on at least a portion of the patient information of the first patient, and contacting an external computing system of each payer of the at least one most likely payer, via a network, to query existence of active coverage of the first patient with the respective payer. The portion of the patient information may include a geographic region associated with the individual and identifying the at least one most likely payer may include identifying the at least one most likely payer based on an association of the at least one most likely payer with the geographic region.

In some embodiments, calculating the estimated coverage amount includes identifying, in the portion of the number of payer records, remittance data for each billing code of the at least one billing code, and calculating, using the remittance data, a remittance estimate. Calculating the estimated coverage amount may include calculating a confidence in similarity of the remittance estimate to an actual future remittance value. Calculating the confidence level may include adjusting the confidence level based at least in part on one or more dates corresponding to the remittance data, where a higher confidence level is associated with a more recent date to a date of the medical claim. Calculating the confidence level may include determining, using at least one machine learning classifier, at least one similarity metric between remittance rates from a prior year and remittance rates from a present year. The payer may be associated with a number of payer plans, and calculating the confidence level may include adjusting the confidence level based at least in part on a similarity between one or more plans corresponding to the remittance data and an active plan of the individual.

In some embodiments, the operations include determining, for each billing code of the at least one billing code, a pre-authorization status corresponding to the respective billing code. Determining the pre-authorization status may include analyzing at least a portion of i) the number of payer records and/or ii) the number of patient records using the respective billing code to identify evidence of authorization requests from one or more of the number of patients. Analyzing the i) the number of payer records and/or ii) the number of patient records may include determining a historic pattern of coverage declinations associated with the respective billing code indicative of likelihood of a pre-authorization requirement by the payer. The portion of i) the number of payer data records and/or ii) the number of patient data records may be analyzed further using an active payer plan of the individual. The operations may include initiating an authorization request submission with a first payer of the at least one payer on behalf of the individual. Determining the pre-authorization status may include automatically issuing, to an external computing system of the payer via a network, a request to determine authorization status of a service corresponding to the respective billing code on behalf of the individual.

In some embodiments, identifying the at least one payer includes identifying a liability payer of the at least one payer for the first patient. The operations may include determining, for each billing code of the at least one billing code, a likelihood of applicability to liability coverage. Determining the likelihood of applicability to liability coverage may include determining, using at least one machine learning classifier, a correlation between one or more billing codes of the at least one billing code and a historic pattern for remittance by one or more payers of a number of liability payers including the liability payer. Identifying the liability payer may include locating liability coverage using employment information of the individual. Identifying the liability payer may include locating liability coverage using employment information of a guarantor associated with the individual. Identifying the liability payer may include identifying, using the patient information of the individual, the guarantor.

In one aspect the present disclosure relates to a cloud network-based platform for emergency medical services applications, the platform including a computer-aided dispatch (CAD) system including software logic configured for execution on processing circuitry and/or hardware logic, where the software logic and/or hardware logic is configured to perform CAD operations including identifying, in relation to a dispatch event involving an individual, dispatch information including location information identifying a location of the dispatch event, and demographic information identifying the individual, and providing, via a first network interface for use by an emergency medical services (EMS) charting system of a caregiver team dispatched by the CAD system, the dispatch information, the charting system including software logic configured for execution on processing circuitry and/or hardware logic, where the software logic and/or hardware logic is configured to perform EMS operations including obtaining, via a second network interface, the dispatch information, receiving, via one or more input interfaces, one or more indicators of care provided to the individual by the caregiver team, and using the one or more indicators, automatically populating an electronic patient record (ePCR), and the predictive analytics platform including software logic configured for execution on processing circuitry and/or hardware logic, where the software logic and/or hardware logic is configured to perform analytics platform operations including receiving, via a third network interface, the demographic information, accessing a data collection including a number of patient data records corresponding to a number of patients, automatically identifying, using the demographic information, a patient record in the data collection corresponding to the individual, and providing, via a fourth network interface, at least a portion of a set of data elements of the patient record to the charting system. The charting system may automatically populate a demographic information portion of the ePCR using the portion of the set of data elements of the patient record.

In some embodiments, the charting system obtains the dispatch information from a computing system of an EMS agency. A computing system associated with a transport vehicle may include at least a portion of the software logic and/or hardware logic of the charting system. Receiving the one or more indicators may include automatically receiving at least one indicator from an input interface of the one or more input interfaces communicatively coupling the charting system to a medical device.

In some embodiments, the dispatch information relates to a non-emergency dispatch event, and the analytics platform operations include accessing a number of payer records of the data collection, where the number of payer records corresponding to a number of payers, identifying, using the number of payer records, at least one payer for the individual, and automatically pre-qualifying the individual for transport by the caregiver team. Automatically pre-qualifying the individual for transport may include automatically verifying, with an external computing system of the payer via a network, active coverage of the individual. Identifying the at least one payer may include identifying at least one most likely payer of the number of payers based on at least a portion of the demographic information of the patient and contacting an external computing system of each payer of the at least one most likely payer, via a network, to query existence of active coverage of the individual with the respective payer. Automatically pre-qualifying the individual for transport may include obtaining pre-approval for transport. Identifying the at least one payer may include determining, for each billing code of at least one billing code corresponding to the non-emergency dispatch event, a pre-authorization status corresponding to the respective billing code. Determining the pre-authorization status includes analyzing at least a portion of i) the number of payer data records and/or ii) the number of patient data records using the respective billing code to identify evidence of authorization requests from one or more of the number of patients. Analyzing the i) the number of payer data records and/or ii) the number of patient data records may include determining a historic pattern of coverage declinations associated with the respective billing code indicative of likelihood of a pre-authorization requirement by the payer. Determining the pre-authorization status may include automatically issuing, to an external computing system of the payer via a network, a request to determine authorization status of a service corresponding to the respective billing code on behalf of the individual. The analytics platform operations may include initiating an authorization request submission with a first payer of the at least one payer on behalf of the individual.

In some implementations, the dispatch information relates to an emergency dispatch event, and the analytics platform operations include determining, for each billing code of at least one billing code corresponding to the emergency dispatch event, a likelihood of applicability to liability coverage. Determining the likelihood of applicability to liability coverage may include determining, using at least one machine learning classifier, a correlation between one or more billing codes of the at least one billing code and a historic pattern for remittance by one or more payers of a number of liability payers including the liability payer. The analytics platform operations may include, responsive to receiving the demographic information, identifying supplemental demographic information correcting incorrect or inconsistent demographics information.

The foregoing general description of the illustrative implementations and the following detailed description thereof are merely exemplary aspects of the teachings of this disclosure and are not restrictive.

BRIEF DESCRIPTION OF THE DRAWINGS

The accompanying drawings, which are incorporated in and constitute a part of the specification, illustrate one or more embodiments and, together with the description, explain these embodiments. The accompanying drawings have not necessarily been drawn to scale. Any values dimensions illustrated in the accompanying graphs and figures are for illustration purposes only and may or may not represent actual or preferred values or dimensions. Where applicable, some or all features may not be illustrated to assist in the description of underlying features. In the drawings:

FIG. 1B is a flow chart of an example method for performing machine learning analysis on a data universe of information resources to calculate a payment estimation by applying historic payment patterns to a present medical claim;

FIG. 3A through FIG. 3D are flow charts of an example method and sub-methods for calculating a combined payment estimate by applying historic patient payment patterns and historic payer payment patterns to a present medical claim;

FIG. 9 is a flow chart of an example method for correcting and/or updating patient data through analyzing patient information available in a data universe of information resources;

FIG. 13A illustrates a flow diagram of an example process for training machine learning models and deriving combined data models directed to predicting the identity of payers based on subscriber identification format;

FIGS. 13B-1 and 13B-2 illustrate flow diagrams of example processes for applying and updating the trained machine learning models of FIG. 13A;

FIG. 13C-1 and FIG. 13C-2 illustrate a flow chart of an example method for identifying potential payers for a patient's medical treatments;

FIG. 15B-1 and FIG. 15B-2 illustrate a flow chart of an example method for estimating reimbursement amounts for services;

FIG. 16C-1 and FIG. 16C-2 illustrate a flow chart of an example method for determining whether a liability payer is likely responsible for payment for medical services rendered to a patient;

FIG. 18 illustrates a screen shot of an example user interface for presenting payers, estimated reimbursement amounts, and estimated payment dates for medical services rendered to a patient.

DETAILED DESCRIPTION OF ILLUSTRATIVE EMBODIMENTS

Figure 1A:
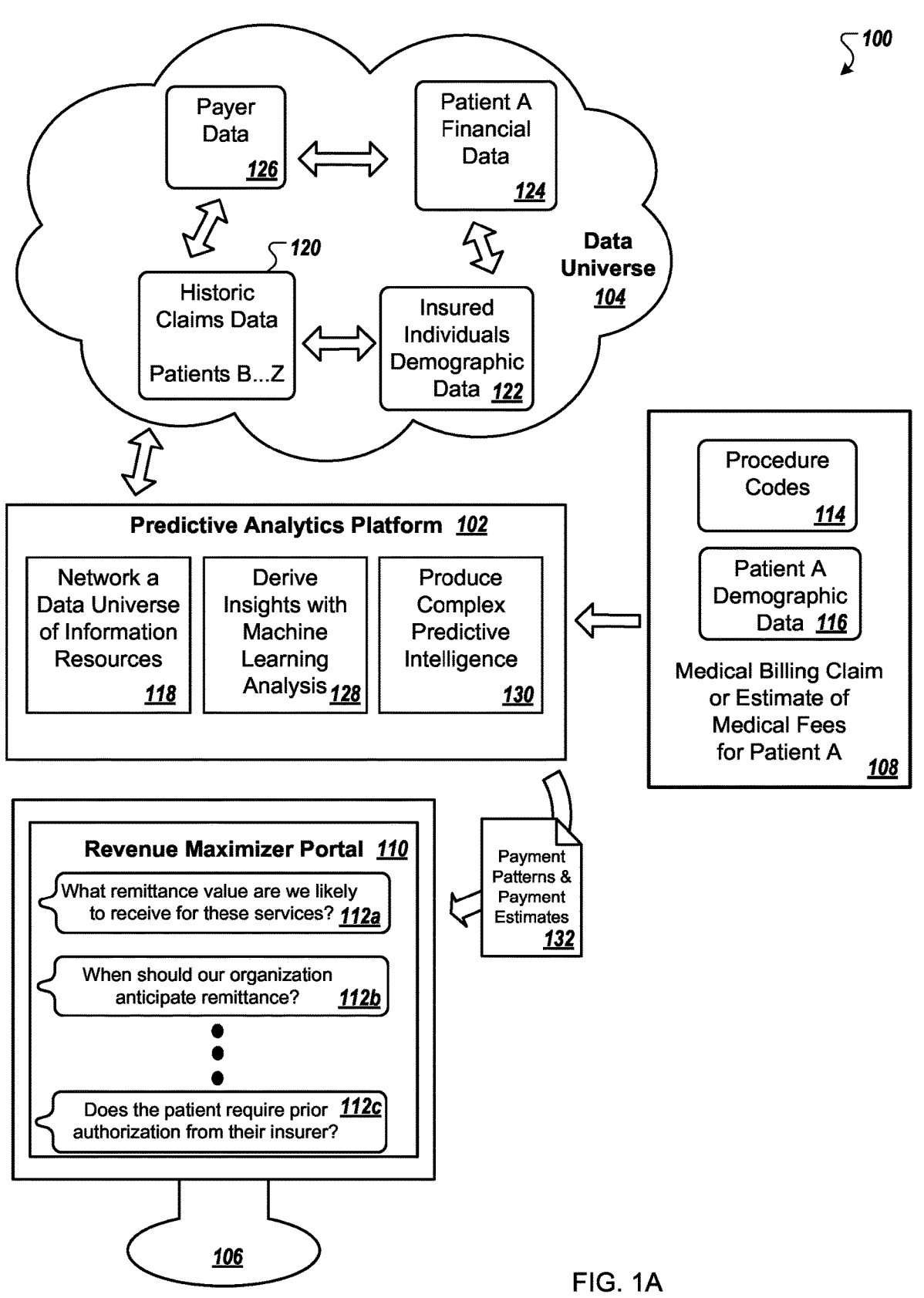
FIG. 1A is a process flow diagram of an example process for using a predictive analytics platform to perform machine learning analysis on a data universe of information resources to produce complex predictive intelligence.

The description set forth below in connection with the appended drawings is intended to be a description of various, illustrative embodiments of the disclosed subject matter. Specific features and functionalities are described in connection with each illustrative embodiment; however, it will be apparent to those skilled in the art that the disclosed embodiments may be practiced without each of those specific features and functionalities.

Reference throughout the specification to "one embodiment" or "an embodiment" means that a particular feature, structure, or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments. Further, it is intended that embodiments of the disclosed subject matter cover modifications and variations thereof.

It must be noted that, as used in the specification and the appended claims, the singular forms "a," "an," and "the" include plural referents unless the context expressly dictates otherwise. That is, unless expressly specified otherwise, as used herein the words "a," "an," "the," and the like carry the meaning of "one or more." Additionally, it is to be understood that terms such as "left," "right," "top," "bottom," "front," "rear," "side," "height," "length," "width," "upper," "lower," "interior," "exterior," "inner," "outer," and the like that may be used herein merely describe points of reference and do not necessarily limit embodiments of the present disclosure to any particular orientation or configuration. Furthermore, terms such as "first," "second," "third," etc., merely identify one of a number of portions, components, steps, operations, functions, and/or points of reference as disclosed herein, and likewise do not necessarily limit embodiments of the present disclosure to any particular configuration or orientation.

Furthermore, the terms "approximately," "about," "proximate," "minor variation," and similar terms generally refer to ranges that include the identified value within a margin of 20%, 10% or preferably 5% in certain embodiments, and any values therebetween.

All of the functionalities described in connection with one embodiment are intended to be applicable to the additional embodiments described below except where expressly stated or where the feature or function is incompatible with the additional embodiments. For example, where a given feature or function is expressly described in connection with one embodiment but not expressly mentioned in connection with an alternative embodiment, it should be understood that the inventors intend that that feature or function may be deployed, utilized or implemented in connection with the alternative embodiment unless the feature or function is incompatible with the alternative embodiment.

Aggregation and analysis of the data maintained by a wide range of distributed data sources enables a prediction and estimation of medical claims payments. These data sources include, but are not limited to, medical providers, billing companies, medical provider administration platforms, medical and liability insurance companies, credit and banking institutions, and employment databases and are referenced herein as part of a "data universe" of information. When aggregated and analyzed by a predictive analytics platform as described herein, historic trends and patterns within the data available from the data universe enables the prediction and estimation of future medical claims payments.

The systems and methods described herein provide at least several benefits for patient care. As one example, these systems and methods enable a fast and accurate prediction and estimation of future medical claims payments. This enables patients to receive accurate information about their insurance coverage and benefits early in the process of their medical care. For example, the system may be able to provide this information at the point of care by EMS resulting in immediate transport to a preferred medical provider and avoid the health risks of later stage transfers. Also, the system provides coverage and benefits information to patients that may include sources of coverage and benefits of which the patient was unaware. For example, the patient may have not realized their eligibility for Medicaid or another government benefit. For non-emergency medical care, these systems and methods enable the patient to better plan their treatments with evaluations of care providers, treatment options, and associated costs. Thus, the patient is empowered by informed medical decisions and is not surprised and disadvantaged by unexpected bills after the fact. The systems and methods herein also enable health care providers to devote more of their staff and financial resources to patient care than to billing and collections. Further, more accurate revenue predictions for health care providers enables these providers to make informed decisions on the staffing and medical equipment purchases to better serve the needs of their patients.

The platform as described herein creates a predictive model based on a hybrid of data for a particular patient with data for payers associated with the particular patient to provide a prediction and estimation for a medical claim for the particular patient. The platform may utilize demographic and insurance coverage discovery to further improve the accuracy and timeliness of the predictions and estimations. "Discovery" refers to a process of finding and identifying information relevant to a medical claim that may be unknown and/or unavailable to a patient, payer, and/or provider prior to the discovery process or information of which the patient, payer, and/or provider was unaware of prior to the discovery process. The data hybrid and the predictive analytics applied to this hybrid data, as described herein, enables accurate, real-time, and interactive payment estimations. As described in examples provided herein, these real-time estimations may enable medical transport dispatch and scheduling decisions, enable prescription selections, enable interactive claims preparation that maximize remittances and minimize collection times, enable interactive claims submissions that maximize remittances, and enable real-time pre-payment calculations. Additionally, the real-time estimations enable medical provider decisions that improve the efficacy and efficiency of that care. For example, the billing, demographic, and coverage information provided by the predictive analytics platform may enable immediate transport to preferred providers within a patient's insurance coverage. The predictive analytics platform enables all of these real-time services at high confidence levels and with financial accuracy because of the hybrid nature of the data universe accessed by this platform. As an additionally benefit, the systems and methods described herein improve billing accuracy, completeness, and timeliness of collections, thereby enabling medical providers to capture revenue that has heretofore been missed and to reduce the time and expense spent on performing transactions to obtain information.

The trends uncovered through analysis of historic information in the data universe enable accurate predictions of the likelihood of a patient and a payer to remit medical claims payments. The historic information, in some examples, may include services rendered, products sold, patient demographic information, patient insurance information, and remittance received from various payers to reimburse provision of medical services and products. The data universe may further include information regarding the various payers and the payer plans, such as copayment levels, deductible amounts, reimbursement eligibility requirements, and reimbursement amounts.

The inventors recognized that, by applying machine learning algorithms and data analytics to historic information, medical providers may be supplied with complex predictive intelligence, such as dependable revenue stream estimates and revenue forecasting. Thus, systems and methods described herein provide a technical solution to the technical problem of reliably predicting revenue streams from an abundance of payer sources each having different reimbursement levels and requirements for coverage eligibility. Further, the inventors recognized that in combining data sources and applying machine learning analysis, the resultant data analytics may support real-time or near-real-time decision making that had not previously been possible, such as rapid patient pre-approval for medical procedures and prescription products as well as complex dynamic scheduling of mobile medical services. Thus, systems and methods described herein additionally provide a technical solution to the technical problem of overcoming resource availability obstacles and reimbursement obstacles to automatically deploy resources to patients in need in a timely manner, thereby improving patient outcomes while improving the bottom line.

In one aspect, the present disclosure relates to a predictive analytics platform developed to harness the intelligence of data records compiled in a data universe to supply revenue maximizing predictive intelligence to medical providers. Turning to FIG. 1A, a process flow diagram of an example process 100 includes a predictive analytics platform 102 for performing machine learning analysis on a data universe 104 of information resources to produce complex predictive intelligence. A representative of a medical provider may interact with the predictive analytics platform 102 via a revenue maximizer applications portal 110 accessible via a computing device 106.

The revenue maximizer application portal 110, in some embodiments, is designed to submit requests to the predictive analytics platform 102 via input provided by the representative through a graphical user interface to obtain answers to revenue inquiries 112. The revenue inquiries 112, in some examples, may relate to medical provider questions such as, in some examples, "what remittance value are we likely to receive for these services?" 112a, "when should our organization anticipate remittance?" 112b, and "does the patient require prior authorization from their insurer?" 112c. The requests may include or reference medical claim information 108 such as one or more procedure codes 114 and patient demographic data 116. As illustrated, the medical claim information 108 presented relates to a medical billing claim or estimate of medical fees regarding a particular patient ("Patient A"). The medical claim information 108 may vary based on the request presented to the revenue maximizer portal 110. Additionally, in some embodiments, claims information 108 regarding a set of medical claims may be presented to the predictive analytics platform 102 for revenue forecasting purposes.

In an implementation, in addition to or as an alternative to receiving input via the revenue maximizer portal 110, the predictive analytics platform 102 may receive all or a portion of input through an application programming interface (API) accessed by and/or batch files provided by the source of the input data (e.g., provider or billing service for provider). In an implementation, the revenue maximizer portal 110 may include a selectable control in the form of a displayed icon or tab. Activation of this control by the user of the portal 110 may enable the platform 102 to pull data in through the API and/or the batch files.

In some embodiments, the predictive analytics platform 102 applies the claim information 108 in accessing 118 the data universe 104. Data fields contained in the claim information 108, for example, may be used to cross-reference or link with various data records in the data universe 104. The claim information 108 may be obtained, for example, from a claims processing system (e.g., a newly generated claim, in-process claim, or a claim recently submitted for reimbursement). In some implementations, the claim information 108 may represent data collected prior to claim generation, such as a portion of a patient's electronic chart.

The claim information 108, for example, may be obtained from an electronic patient charting file, i.e., an electronic patient care record (ePCR) populated in real-time by emergency medical services (EMS) during an emergency medical event. In an implementation, a mobile device may include an application configured to populate the ePCR. The mobile device may communicatively couple to the predictive analytics platform 102, for example, via a shared cloud-based platform encompassing both a patient charting service and the predictive analytics platform and providing these as Software-as-a-Service (SaaS). The shared cloud-based platform may also include service such as computer aided dispatch and medical transport dispatch and scheduling. Alternatively, servers from separate providers or clouds may service the patient charting service and the predictive analytics platform and these servers may communicatively couple via a long-range network such as the Internet.

As another example, the claim information 108 may originate from an electronic health record (EHR) generated by a physician, hospital caregiver, or other non-EMS service provider. The EHR may be stored on-premises and/or in a cloud database and the predictive analytics platform may access the EHR via a communicative coupling (e.g., Internet, cellular network, etc.) with the appropriate database.

The procedure codes 114 of the claim information 108, for example, may include Current Procedural Terminology (CPT®) codes and/or Healthcare Common Procedure Coding System (HCPCS) codes. Rather than or in addition to procedure codes 114, in some implementations, the claim information 108 includes reference codes or identifiers not included in the CPT and/or HCPCS listings such as, in some examples, medical equipment and/or supply identifiers, prosthetics and/or orthotics devices and supplies identifiers, home health services identifiers, and/or prescription drug identifiers. The patient demographic data 116, in some examples, may include the patient's name, identification number, address, social security number, height, weight, gender, date of birth, and/or medical history.

The accessing 118, in some embodiments, includes accessing a set of records maintained by or related to historic claims made by the provider, such as historic claims data 120 and insured individuals' demographic data 122. The historic claims data 120, in some examples, may include reference codes as discussed in relation to the procedure codes 114 above, as well as, in some examples, dates of medical services, location(s) of medical services, patient identifiers, payer identifiers, payer plan and/or group identifiers, payer pre-approval references, invoice amounts, reimbursement amounts, identifiers of responsible parties if not the patient, a portion of patient demographic information such as name, address, date of birth, gender, and/or relationship to responsible party, and/or accident information (e.g., regarding an indemnity claim). The insured individuals' demographic data 122, in some examples, may include patient identifiers, geographic regions or address portions (e.g., city, state, and/or zip code), age or age ranges, medical history identifiers (e.g., co-morbidities, prescription data, prior major medical services such as surgeries, etc.), payer identifiers, payer plan identifiers, and/or payer group identifiers.

In some embodiments, the accessing 118 includes accessing a set of records maintained by or provided by a third party, such as patient financial data 124 and/or payer data 126. The patient financial data 124, for example, may be accessed by obtaining a credit score or credit report from a credit reporting agency or financial institution. In particular, the patient financial data 124 may be obtained through requesting a patient financial clearance or risk analysis related to medical debt from a credit reporting agency specializing in healthcare reimbursement data, such as TransUnion LLC of Chicago, Ill. or Experian Health by Experian Information Solutions, Inc. of Costa Mesa, Calif. The patient financial data 124, in some embodiments, includes financial data related to a responsible party, such as a parent or spouse of the patient. The payer data 126, in some implementations, includes coverage details for insurance plans for each of a collection of payers. The payers may include health insurance payers, medical insurance payers, dental insurance payers, vision insurance payers, and/or indemnity insurance payers. The coverage details, for example, may be collected from computer systems of each payer on an as-needed basis (if not already accessed) or on a scheduled basis (e.g., annually or another periodic timeframe when updates are applied to various plans offered by the payer(s)).

In some embodiments, a portion of the data records in the data universe 104 contain de-identified data. The de-identified data may remove information that can be used to link (e.g., "reverse engineer") the data to match the data to a certain individual or small number of individuals. De-identification, in some examples, may include removing patient name, social security number, exact birth date, street address, and phone number from records such as the historic claims data 120 and the insured individuals' demographic data 122.

In some embodiments, the predictive analytics platform 102 derives insights 128 from the data accessed from the data universe 104, for example using machine learning analysis and or other statistic data analysis techniques. The predictive analytics platform 102, for example, may include machine learning classifiers trained using historic data records to identify patterns in the data records of the data universe 104 based upon claims information such as the information supplied in the medical claim information 108. In another example, the predictive analytics platform 102 may derive insights 128 from the data universe 104 through cluster analysis of data records by applying techniques such as, in some examples, centroid-based clustering, density-based clustering, and/or multi-dimensional clustering. The information accessed from the data universe 104 may be arranged in a variety of manners to apply the machine learning analysis and/or cluster analysis such as, in some examples, a convolutional neural network (CNN), deep neural network (DNN), clustering tree, and/or synaptic learning network. The arrangement of data and/or type of learning analysis applied may be based in part upon the type and depth of information accessed, the desired insights to draw from the data, storage limitations, and/or underlying hardware functionality of the predictive analytics platform 102.

The predictive analytics platform 102, in some embodiments, produces complex predictive intelligence 130, for example by deriving metrics and/or calculating estimates using the derived insights 128. For example, the predictive analytics platform 102, in response to the revenue inquiry 112a regarding remittance value related to services, may calculate, from derived insights 128 related to reimbursement from each of a set of payers represented in the payer data 126, predictive intelligence 130 including a combined estimated remittance value for one or more services covered by one or more payers (e.g., primary insurance plus secondary insurance, primary insurance plus patient deductible value, etc.). In another example, responsive to the revenue inquiry 112b regarding remittance timing, the predictive intelligence 130 include calculating amounts per revenue period for each of the one or more services, depending upon typical payment timing of each payer. In a third example, responsive to the revenue inquiry 112c regarding prior authorization, the predictive intelligence 130 may include, based on an indication from the machine learning analysis 128 that prior authorization is likely needed. In various implementations, the platform 102 may automatically issue a request for authorization from the payer, may automatically notify a third party to request authorization from the payer, or may provide a notice to the user of the platform 102 that the prior authorization is required. The notice to the user may include an identification of the third party to request this authorization.

In some embodiments, the predictive analytics platform 102 provides the complex predictive intelligence 130 to the revenue maximizer portal 110, for example in the form of payment patterns and payment estimates 132 as illustrated. The complex predictive intelligence may be rendered in a graphical user interface in the form of short textual and/or numerical answers, charts, graphs, interactive spreadsheets, and/or interactive reports, in some examples.

FIG. 1B is a flowchart of an example method 150 for performing machine learning analysis on a data universe of information resources to calculate a payment estimation by applying historic payment patterns to a present medical claim. The payment estimation may include contributions from one or more sources and may be based upon historic reimbursement amounts for the same or similar billing codes found in the present medical claim. The method 150, for example, may be performed by the predictive analytics platform 102 of FIG. 1A interfacing with various data records 120, 122, 124 and/or 126 of the data universe 104. The method may be performed by or on behalf of a medical service provider, such as the providers described in relation to FIG. 1A. For example, the method 150 may be performed responsive to the revenue inquiry 112a being submitted at the revenue maximizer portal 110 of FIG. 1A.

In some implementations, the method 150 begins with receiving a medical claim for a first patient including at least one billing code and demographic data related to the first patient (152). The medical claim, for example, may be a new medical claim entered into a billing system by hand and/or at least partially automated through entry from an electronic chart system (e.g., including information submitted by medical personnel and/or automatically captured through interfacing with medical equipment). The at least one billing code, for example, may be a type of code discussed in relation to the procedure codes 114 of FIG. 1A.

Figure 3A:
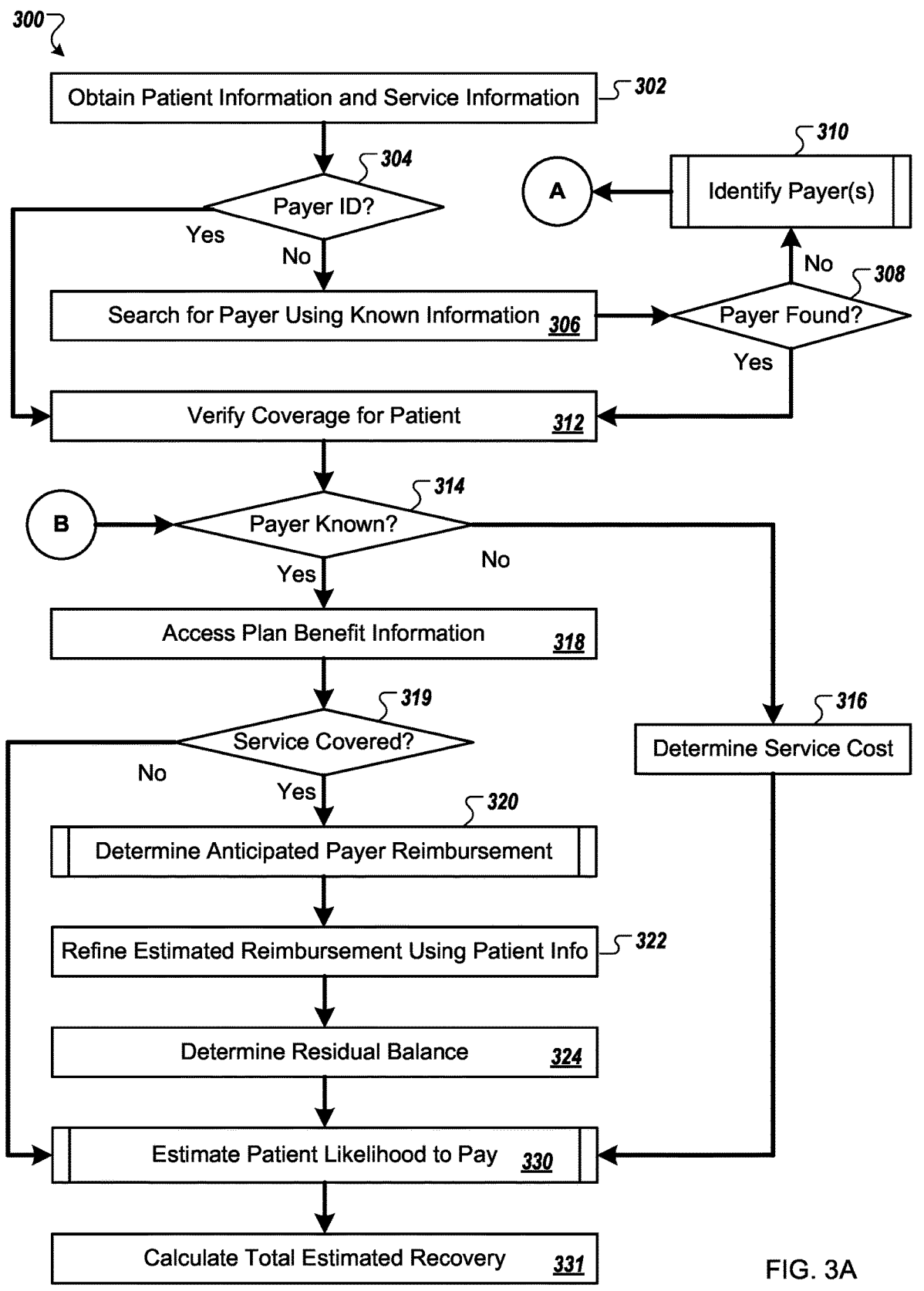
Figure 3B:
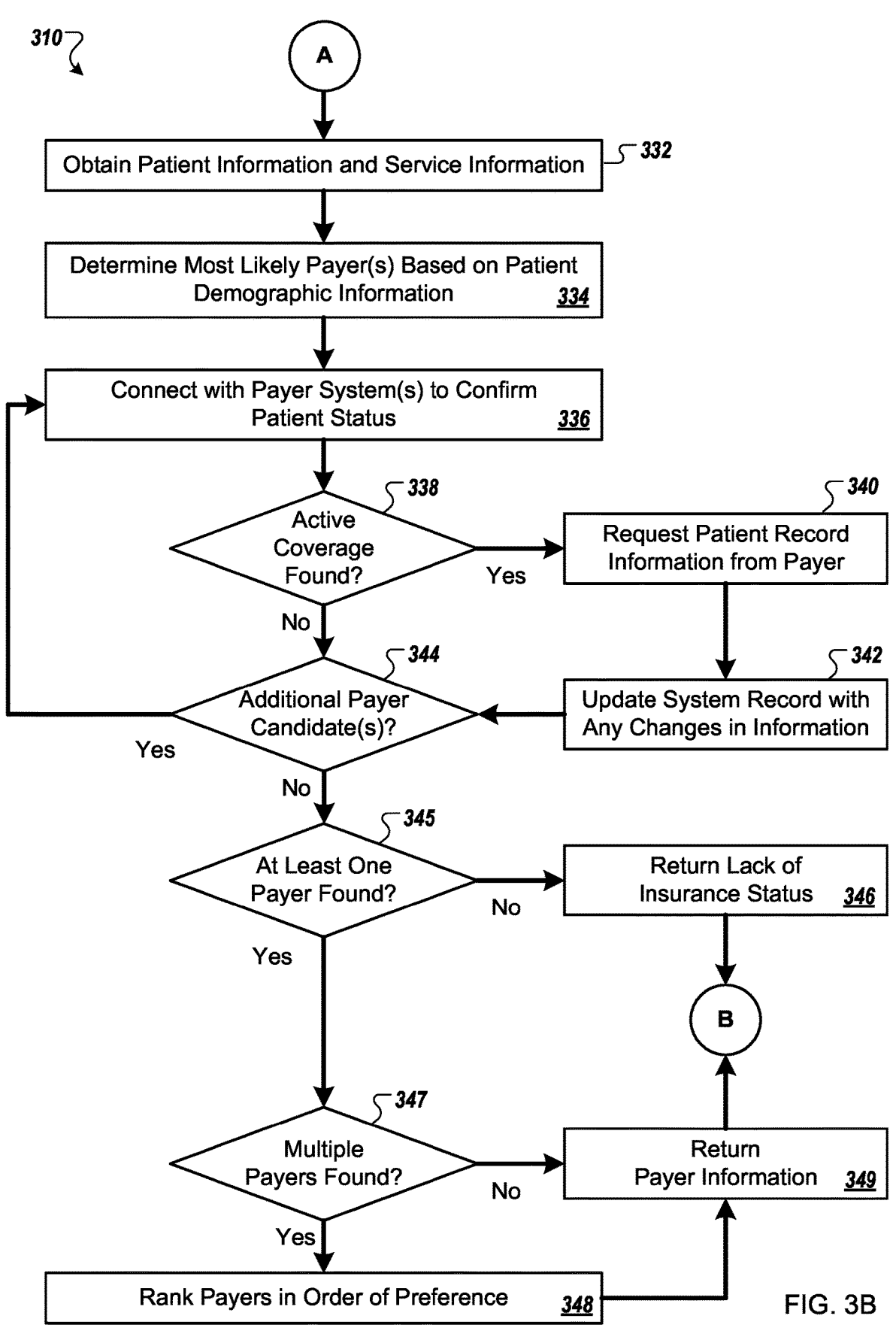

In some implementations, one or more payers for the medical claim are identified using the demographic data (154). The demographic data, for example, may include similar aspects to the demographic data 116 described in relation to FIG. 1A. In one example, local records of a known patient may be automatically queried to match the patient to payer(s). In another example, partial demographic data may be used to match to an existing patient and, using that patient information, the patient may be matched to one or more payers. In a further example, the demographic data may be used to query likely payers to identify an active insurance plan associated with the patient. In addition to identifying payers, the billing code(s) may be cross-referenced to confirm the appropriate payer has been located (e.g., a payer that covers the billing code(s)). FIG. 3B, below, provides an example method for identifying payers based on patient demographic information.

In some implementations, a patient data collection housing historic patient data records for a population of second patients is accessed (156). The patient data collection, for example, may be the insured individuals' demographic data 122 described in relation to FIG. 1A. The patient data collection may be accessed from one or more local and/or third-party data sources. Accessing the patient data collection may include, for example, accessing patient records based upon relevance to the billing code(s). Accessing the patient data collection may include, in another example, accessing patient records based on similarity between patient demographics and the demographic data of the first patient.

In some implementations, a payer data collection housing payer data records for a first identified payer is accessed (158). The payer data collection, for example, may be a portion of the payer data 126 as described in relation to FIG. 1A.

In some implementations, for each billing code, a payer payment pattern is identified using one or more patient data records and one or more payer data records for the billing code (160). The predictive analytics platform 102 of FIG. 1A, for example, may analyze the patient data records (historic claims data 120) to identify claims reimbursement records corresponding to the same billing code(s) and the same payer. In some embodiments, the predictive analytics platform 102 identifies patient data records corresponding to a same payer plan as the first patient's plan to forecast reimbursement based upon identical plan information, as matched by the payer data collection. In some embodiments, since plan coverage can change over time, the patient data record(s) and payer data record(s) may represent recent records (e.g., within one year, within a same calendar year, etc.). In some embodiments, where direct comparison is unavailable (e.g., the same billing code and/or the same plan) or includes very limited data points, records corresponding to similar billing codes and/or similar plans may be identified and analyzed by the predictive analytics platform. Similar plans, for example, may be identified by performing machine learning analysis on the payer data collection. Similar billing codes may be identified through reference to a billing code repository. The similar billing codes, for example, may include a closeness in number identified through applying a filter to the billing codes. In illustration, HCPS codes B408X describe different styles of feeding tubes. Similar billing codes may be identifying through natural language processing of a brief description associated with each code. For example, the HCPS codes for non-emergency ground transportation include A0100 (taxi), A0110 (bus), A0120 (mini-bus), and A0130 (wheelchair van). Through natural language processing, each of these codes may be identified as "non-emergency transportation: [ground vehicle]" as opposed to air travel (e.g., A0140) or other ancillary service codes associated with transporting a patient. As demonstrated above, in some embodiments, filtering by a portion of the code followed by natural language processing, in some embodiments, may be used to identify the closest codes in similarity, as well as, in some examples, proximity in code numbering (e.g., A110 is more similar to A120 than A0428: ambulance service, basic life support, non-emergency transport). The payer patient pattern may include one or more remittance values, such as a first (most recent) remittance value related to the same payer plan and a different geographic region, but a second (less recent) remittance value related to the same payer plan and a same geographic region. Other combinations are possible, as would be understood from the preceding examples of similarities in billing codes and payer plans. Even with the same billing code, same payment plan, same service provider, and same month, the reimbursement may differ based upon patient circumstances, for example whether a deductible was met. Thus, in accumulating multiple remittance examples a better assessment may be made regarding anticipated reimbursement related to a particular service or product.

In some implementations, if any additional payers were identified (162), steps 158 and 160 are repeated for each additional payer.

In some implementations, a financial history data collection housing one or more financial data records for the first patient is accessed (164). For example, the predictive analytics platform may access the financial history data collection (patient A financial data 124) from the data universe 104. The financial history data collection, for example, may include past payment history to the medical service provider for historic services. In another example, the financial history data collection may include personal or family income and credit history information. The credit history may include medical credit history. Further, the financial history data collection may include information regarding a medical spending plan available to the first patient or a deductible amount remaining for the first patient in relation to the one of the payer(s).

In some implementations, a patient payment pattern is identified based on the financial records (166). The patient payment pattern, for example, may be identified by matching the patient demographic data to one or more of the second patients similar to the first patient and analyzing likelihood to pay among the similar patients. Similarities, in some examples, may include similarities in age range, gender, employment status, disability status, geographic region, and/or responsible party status. Further, in some embodiments, a type of medical service (e.g., a life-changing service such as cancer treatment, limb amputation, etc. versus a non-life-changing service such as tonsil removal) and/or a cost to patient range (e.g., hundreds, thousands, over ten thousand, etc.) may be considered in matching the first patient to the one or more second patients. The patient payment pattern, for example, may include one or more likelihoods (e.g., percentage likelihood, likelihood on a scale of one to ten), such as a first likelihood related to a patient most demographically similar but with a more dissimilar cost to patient range and a second likelihood related to a patient less demographically similar but within a same cost to patient range as the medical claim for the first patient.

In some implementations, the payer payment pattern(s) and patient payer pattern are applied to the medical claim to calculate a payment estimation (168). The predictive analytics platform 102 and/or a revenue maximizer portal 110 application, for example, may perform calculations to determine payment estimates based upon the values and likelihoods contained within the payer payment pattern(s) and patient payer pattern (e.g., the payment patterns & payment estimates 132 of FIG. 1A). The calculations may include statistically combining costs and likelihoods to produce a final estimate.

Although described as a particular series of operations, in some embodiments, more or fewer steps may be included in the method 150. For example, in identifying similar plans, the method 150 may include accessing payer data records corresponding to another payer with similar plan coverage to the first payer. In another example, in identifying similar billing codes, the method 150 may include accessing a data collection of billing codes and analyzing billing codes to identify corresponding billing codes. In a further example, rather than accessing a financial history data collection (162), the method 150 may include obtaining medical credit information for the first patient in real-time or near real-time. In further embodiments, certain steps of the method 150 may be performed in a different order or in parallel. For example, the payer payment pattern(s) may be identified (operations 158 through 162) at least partially in parallel with identifying the patient payment pattern (operations 164 and 166). Other modifications of the method 150 are possible.

Figure 2:
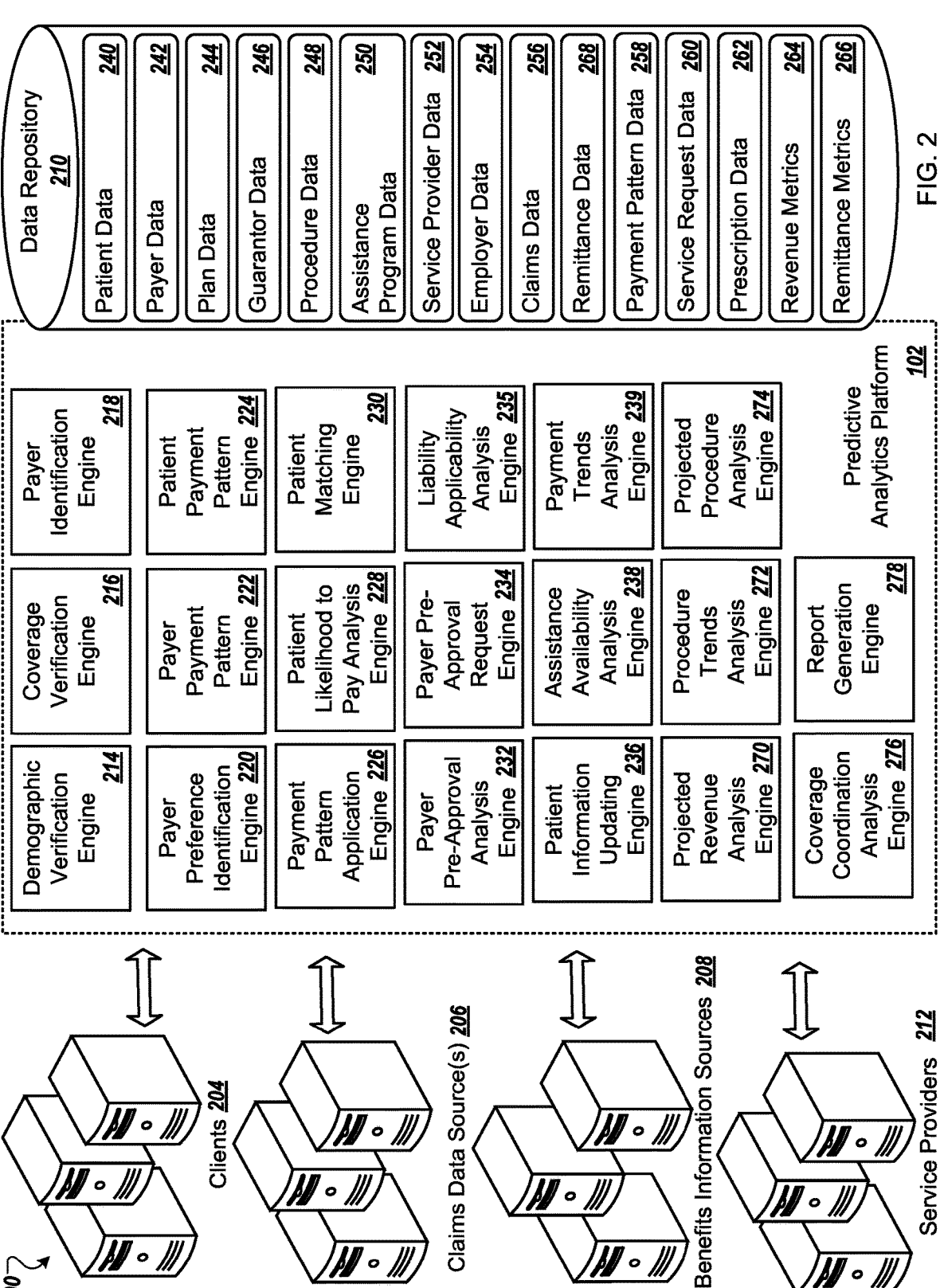
FIG. 2 is a block diagram of an example system including a platform and environment for performing machine learning analysis on a data universe of information resources to produce complex predictive intelligence.

FIG. 2 is a block diagram of an example system including the predictive analytics platform 102 and environment 200 for performing machine learning analysis on portions of a data universe of information resources gathered and/or networked by the predictive analytics platform 102 (e.g., represented by a data repository 210) to produce complex predictive intelligence. The predictive analytics platform 102, for example, may gather and/or network the various information sources, in some examples, from one or more claims data sources 206, benefits information sources 208, and/or service providers 212. The predictive analytics platform 102 may generate, through analyzing the gathered and/or networked information using machine learning classifiers and/or other clustering and pattern identification algorithms, complex predictive intelligence for a set of clients 204. The clients 204 may access the predictive analytics platform 102 via a networked connection. For example, the clients may access the predictive analytics platform 102 through the revenue maximizer portal 110 described in relation to FIG. 1A.

In some implementations, the predictive analytics platform 102 includes a set of engines (e.g., programs, algorithms, or applications) for performing, alone or in combination, predictive analytics on behalf of the clients 204. The engines may include software and/or hardware logic for performing the operations of each program, algorithm, or application. For example, in some embodiments, one or more engines include at least a portion of its functionality as hardware logic encoded into a programmable logic chip or reprogrammable processor. Each engine may access various sets of data as illustrated in the data repository 210. Although represented as a single repository, the data repository 210 represents a networked or otherwise linked collection of data sources including, in some examples, one or more databases, one or more data warehouses, one or more neural data networks, one or more synaptic data networks, and/or other arrangements of interconnected and stored data. Further various engines of the predictive analytics platform 102 may be designed to query or otherwise access information in real-time from one or more external data sources.

The predictive analytics platform 102, in some implementations, includes a demographic verification engine 214 for verifying and/or supplementing patient information with demographic information or other patient record information obtained from an external source. The demographic verification engine 214, for example, may compare external information with patient data 240 maintained by the medical provider and update or supplement the information where appropriate.

In some implementations, the predictive analytics platform 102 includes a coverage verification engine 216 configured to automatically submit patient information to a payer system to confirm active coverage of the patient by the payer. The coverage verification engine 216, for example, may be invoked where the coverage for the patient is uncertain or where the most recent coverage verification for the patient was obtained outside a threshold window of time such as, in some examples, over one month, over three months, or longer than six months. To verify coverage, in some embodiments, the coverage verification engine 216 automatically submits identifying demographic information such as, in some examples, name, date of birth, social security number, patient residence, work, or billing address, insurance subscriber number, and/or insurance plan member number to each payer system through an application programming interface (API) or other automated communication means to confirm status of coverage, the goal being to receive a response from at least one payer system confirming active coverage and, thus, positively identifying the payer as a potential medical claim recipient for the service. Some payers will additionally supply patient record information in response to identifying active coverage and/or upon subsequent request, thereby allowing the medical provider to supplement patient information in local records and/or update outdated patient information within local records. In some embodiments, the coverage verification engine 216 coordinates with the demographic verification engine 214 to update and/or supplement demographic information related to a patient.

In some implementations, the predictive analytics platform 102 includes a payer identification engine 218 for automatically matching one or more payers with a patient based on demographic and/or other known information regarding the patient. The payers, for example, may include primary insurance providers, Medicare, and Medicaid. Further, the payers may include liability payers such as automotive liability insurance, homeowner insurance, worker compensation insurance, and/or business liability insurance. In some embodiments, a call to the payer identification engine 218 includes an indication of type of insurance to identify (e.g., primary, liability, all, etc.). The payer identification engine 218 may analyze patient data 240 and payer data 242 to determine trends in payer coverage per demographic grouping (e.g., geographic region, age group, etc.). Further, the payer identification engine 218, in some embodiments, analyzes employer data 254 and/or guarantor data 246 to identify trends in employer-provided payer coverage per demographic grouping (e.g., employees of a national organization residing in a particular state or a particular region of the United States). The payer identification engine 218 may return identification of one or more payers. In some embodiments, the payer identification engine 218 further includes a default set of payers (e.g., the top N payers nationally) to suggest as likely payers covering the patient. In some implementations, the payer identification engine 218 automatically confirms coverage by calling the coverage verification engine 216 for each likely payer candidate. Upon confirming, in some implementations, the response from a particular payer may identify one or more secondary payers. For example, when verifying coverage of a primary payer, the primary payer may confirm active coverage and further identify one or more secondary insurance sources on record as being available to the patient.

In some implementations, the predictive analytics platform 102 includes a payer preference identification engine 220 for analyzing available payers in view of services and/or products that will be submitted for reimbursement to identify the most appropriate and/or most desirable payers for claim submission. The payer preference identification engine 220 may prioritize primary insurance sources over secondary insurance sources based on plan type, prioritize liability coverage sources over primary insurance sources based on claim type, prioritize travel or employer liability coverage sources over primary insurance sources based on location of service being outside of the patient's home region, and/or prioritize sources based upon analyzing plan information and identifying available coverage based on billing codes (e.g., service and/or product types). The available payers may be ranked by the payer preference identification engine 220 in order of preference for claim submission for reimbursement.

The predictive analytics platform 102, in some implementations, includes a payer payment pattern engine 222 configured to analyze historic reimbursement data for a payer to identify trends or patterns in amounts, timing, and/or denials. The payer payment pattern engine 222, for example, may access payer data 242, plan data 244, and/or claims data 256. Further, the payer payment pattern engine 222, in some embodiments, accesses patient data 240 to identify trends across groups of insured individuals, such as regional trends. The pattern analysis, in some examples, may be performed using machine learning analysis, cluster analysis, and/or statistical data analysis to identify data patterns within the accessed records. The payer payment pattern engine 222 may return payment pattern data such as the payment pattern data 132 described in relation to FIG. 1A. Further, the payment pattern engine 222, in some embodiments, stores payment pattern data 258 in the data repository 210 for future use.

In some implementations, the predictive analytics platform 102 includes a patient payment pattern engine 224 to identify patient payment trends from historic claims (e.g., claims data 256 cross referenced with patient data 240) based upon a patient medical debt score or rating. In some embodiments, the patient payment pattern engine 224 further uses patient demographic data or other information to refine analysis of similar patients. The demographic data, in some examples, can include geographic region, age range, gender, employment status, and/or income level. The patient payment pattern engine 224 identifies patient payment outcomes related to patients similar to the payer at least in medical credit score or rating. In some embodiments, the patient payment pattern engine 224 identifies the claims data records by first identifying similar patients to the present patient using a patient matching engine 230. Pattern analysis may be applied to the identified claims data records. The pattern analysis, in some examples, may be performed using machine learning analysis, cluster analysis, and/or statistical data analysis to identify data patterns within the accessed records. The payer payment pattern engine 222 may return patient payment pattern data.

In some implementations, the predictive analytics platform 102 includes a payment pattern application engine 226 configured to apply payer payment patterns produced by the payer payment pattern engine 222 and/or patient payer patterns produced by the patient payment pattern engine 224 to calculate payment estimations. Further, in some embodiments, the payment pattern application engine 226 determines a confidence level or rating associated with the payment estimate. The confidence level or rating, in some examples, can include a percentage confidence, a ranked confidence (e.g., on a scale of 1 to X), and/or a ratings confidence (e.g., low, medium, high).

The predictive analytics platform 102, in some implementations, includes a patient likelihood to pay analysis engine 228 for determining whether a remaining balance is likely to be repaid by the patient. The patient likelihood to pay analysis engine 228, in some embodiments, requests a patient financial clearance or risk analysis related to medical debt from a credit reporting agency specializing in healthcare reimbursement data, such as TransUnion LLC of Chicago, Ill. or Experian Health by Experian Information Solutions, Inc. of Costa Mesa, Calif. Further, the predictive analytics platform 102, in circumstances where a responsible party holds the payer coverage (e.g., parent, spouse, guardian, etc.), may identify information regarding the responsible party, for example using the guarantor data 246, and request the patient financial clearance or risk analysis related to medical debt regarding the responsible party. In some implementations, the patient likelihood to pay analysis engine 228 analyzes historic patient payment trends identified by the patient payment patterns engine. The predictive analytics platform 102 determines a likelihood of the remaining balance being repaid by the patient based on the patient financial clearance or risk analysis and, in some embodiments, the historic payment trends.

The predictive analytics platform 102, in some implementations, includes a patient matching engine 230 for identifying similar patients based upon patient demographic data and/or other information relevant to a patient, such as, in some examples, a medical debt score or rating, one or more services provided to the patient, and/or provider plan coverage. The patient matching engine 230 may access the patient data 240 to match features to insured persons in the data repository 210. The patient matching engine 230, in some embodiments, returns exact matches. The patient matching engine 230, in other embodiments, returns both exact matches and similar matches. Similar matches may be qualified with a closeness rating or percentage similarity to the patient. The patient matching engine 230, for example, may return a set of patient identifiers for referencing the de-identified patient data 240.

The predictive analytics platform 102, in some implementations, includes a payer pre-approval analysis engine 232 for determining likelihood of the payer requiring pre-approval for one or more services and/or products recommended by or scheduled for performance by a medical provider. The payer pre-approval analysis engine, for example, may analyze, for example using the payer payment pattern engine 222, trends in historic claims data 256 corresponding to a payer of the patient's coverage to identify claims rejections related to one or more products and/or services identified to the payer pre-approval analysis engine 232. For example, if a claim for a product or service is commonly rejected, this may be due to the product or service only being covered when pre-approval has been obtained. Further, the payer pre-approval analysis engine 232 may analyze the claims data 256 (e.g., via the payer payment pattern engine) to identify indicators of pre-approval within the claims data records 256 corresponding to approved (e.g., reimbursed) claims by the payer. In some embodiments, the payer pre-approval analysis engine 232 analyzes service request data 260 to identify historic requests for authorization. The payer pre-approval analysis engine 232, for example, may apply pattern analysis to the identified claims data records and/or service request data records. The pattern analysis, in some examples, may be performed using machine learning analysis, cluster analysis, and/or statistical data analysis to identify data patterns within the accessed records. The payer pre-approval analysis engine 232 may return an indication of whether there is evidence that authorization is required (e.g., yes or no). The payer pre-approval analysis engine 232 may return, instead of or in addition to a positive or negative answer, a confidence level and/or confidence rating regarding this assessment.

The predictive analytics platform 102, in some implementations, includes a payer pre-approval request engine 234 for automatically submitting a pre-authorization request in relation to a scheduled service or recommended product. The payer pre-approval request engine 234, for example, may receive indication of a payer, a billing code, and a patient, for example a payer identifier and a patient identifier. Further, the payer pre-approval request engine 234 may receive identification of a payer plan. The payer pre-approval request engine 234 may prepare a pre-authorization request based on this information and, using the payer identification, determine automated contact information, such as an API, for submitting the pre-approval request. The payer pre-approval request engine 234 may also receive indication of a requestor such that, after receiving a response from the payer system, the payer pre-approval request engine 234 may automatically alert the requestor of the outcome of the request (e.g., approved, denied). In various implementations, the platform 102 may automatically issue a request for authorization from the payer, may automatically notify a third party to request authorization from the payer, or may provide a notice to the user of the platform 102 that the prior authorization is required. The notice to the user may include an identification of the third party to request this authorization.

In some implementations, the predictive analytics platform 102 includes a liability applicability analysis engine 235 configured to analyze information related to a medical claim to identify whether liability insurance is likely to apply. The applicability analysis engine 235, for example, may access claims data 256 regarding a new claim for a given patient, service request data 260 and/or service provider data 252 regarding scheduled service(s) and/or performed service(s), and/or patient data 240 for the patient including intake data regarding reason for pursuing products and/or services from the medical provider. The applicability analysis engine 235, in some embodiments, performs natural language processing (NLP) of a portion of the claims data, service request data, and/or service provider data to identify terms and/or phrases indicative of a claim qualifying for liability coverage. For example, an ambulance service record by the service provider may indicate that the pick-up location was at an "auto accident", "crash scene", or other phrasing indicative of a car crash, indicating that automotive liability insurance may cover at least a portion of the expense. In some embodiments, the applicability analysis engine 235 identifies selection of codes, check boxes, or other user-selectable or fillable information potentially indicative of applicability of liability coverage from standardized forms, such as medical provider forms or claim submission forms. The applicability analysis engine 235, in some embodiments, analyzes address information associated with one or more services. For example, if the address of provision of emergency medical services matches the address of the patient's employer, worker liability coverage may be indicated. Further, if the address of provision of services (or pick-up by emergency transport) matches a business such as a gym or amusement park, the business liability insurance may be indicated. The applicability analysis engine 235, in some embodiments, accesses historic claims data for the same service(s) to identify trends across the service(s) for submission to liability payers. The pattern analysis, in some examples, may be performed on claims reimbursed by liability payers using machine learning analysis, cluster analysis, and/or statistical data analysis to identify data patterns within the accessed records. The data patterns, for example, may include terms and/or phrases, selection of fields or code entry in fields of standardized forms, and/or groupings of services indicative of applicability to liability coverage. The applicability analysis engine 235 may return indication of applicability is likely (e.g., yes or no). Further, the applicability analysis engine 235, in some embodiments, returns a confidence score or confidence level corresponding to the strength of evidence of applicability to liability coverage identified.

The predictive analytics platform 102, in some implementations, includes a patient information updating engine 236 for expanding upon patient demographic data that may be insufficient for uniquely identifying the patient and/or that contains ambiguous or contradictory information on comparison to another trustworthy source of patient information. The patient information updating engine 236, for example, may receive patient information obtained from an intake process, such as a manual data entry process by service provider personnel into the predictive analytics platform 102 or electronic chart data automatically transferred into the predictive analytics platform 102 by one of the service providers 212. The patient information updating engine 236, in some embodiments, analyzes the patient information in view of identification criteria to determine whether the supplied information is sufficient for positive identification of the patient. For example, a relatively common name and a significant geographic region (e.g., Paul Jacobs of New York) may be insufficient for positive identification of an individual, while a full name plus social security number may be adequate. The rules in determining sufficient information, for example, may analyze the patient information in view of key demographic information such as, in some examples, a full name, at least a partial address (e.g., at least city plus state, a zip code, etc.), a social security number, and/or a date of birth to determine at least one combination of the key demographic information identified in the rules as being sufficient for matching purposes has been supplied. The patient information updating engine 236, in some embodiments, cross-references the received patient information with one or more local records, such as patient data 240 maintained by the predictive analytics platform 102 (e.g., a subset of the patient data 240 belonging to a particular service provider or other non-de-identified patient data) to determine if there are any inconsistencies or ambiguities between the information. For example, the provided information may differ in one or more elements from the stored patient information, such as, in some examples, current address, spelling of the first name, spelling of the last name, and/or date of birth. The patient information updating engine 236, for example, may apply fuzzy logic to identify close to but unmatched spellings in certain fields of demographic data (e.g., patient name, street name, city name, etc.). If the patient information is insufficient and/or the patient information differs in one or more fields from a stored patient data record, in some embodiments, the patient information updating engine 236 contacts additional information sources, the payer providing the patient's active coverage, to obtain recent data. The patient information updating engine 236 then may supplement or update the patient information based upon the contents of the recent data. The patient information updating engine 236, for example, may update both the patient data 240 and the claims data 256 (for a new claim) with the most recent patient information. In another example, the patient information updating engine 236 may present the corrected information for acceptance by a user. Further to the example, the corrected information may be presented along with the present information for acceptance by a representative of the service provider. In some embodiments, the patient information updating engine 236 also provides a confidence level or confidence rating in the newly acquired patient information for review by the representative.

In some implementations, the predictive analytics platform 102 includes an assistance availability analysis engine 238 configured to automatically investigate potential additional sources of medical debt coverage for uninsured or underinsured patients. The assistance availability analysis engine 238, for example, may analyze patient demographic data to identify additional funding sources such as, in some examples, any federal programs, state programs, charitable foundation programs, and/or foundation discount programs. The additional funding sources may vary by location, type of service provider, income level, age, and/or employment status of the patient. Upon identifying eligibility for at least certain programs, such as the federal Medicare and Medicaid programs, the assistance availability analysis engine 238 may automatically initiate enrollment in the programs by filling out online form(s) or other eligibility paperwork using the demographic data stored by the predictive analytics platform 102 in the patient data 240. Further, the assistance availability analysis engine 238, in some embodiments, accesses additional information regarding the payer, such as credit history or debt information, from third party sources to determine eligibility and/or to provide a larger percentage of required information to the eligibility form(s)/paperwork.

The predictive analytics platform 102, in some implementations, includes a payment trends analysis engine 239 configured to analyze remittance received from payers and/or patients to identify patterns within the payments. The patterns, in some examples, may include a length of time between claim submission and reimbursement, a relative amount paid compared to amount billed, patterns of payer rejections, and patterns of claims re-filings directed to other sources of payments, such as liability payers. Further, the patterns may be broken down into subsets, such as billing code categories, payer types (e.g., liability, primary insurance, federal medical coverage programs, etc.), and/or locations (e.g., for a service provider with multiple physical locations). In some embodiments, the payment trends analysis engine 239 applies machine learning analysis, cluster analysis, and/or statistical data analysis to the remittance data 268 to identify data patterns within the accessed records. For example, the payment trends analysis engine 239 may include different machine learning classifiers trained to identify patterns related to the various sets and subsets of payment types. The machine learning classifiers, for example, may be trained using de-identified data collected over a period of time (e.g., at least 3 months, from 3 to 6 months, up to 1 year, 2 years, etc.). The scope of the training data, for example, may depend upon an amount of data available related to the different variables (e.g., an amount of data per payer, an amount of data per service type, etc.). The payment trends analysis engine 239 may return one or more sets of data patterns for analysis, for example by a projected revenue analysis engine 270.

In some implementations, the predictive analytics platform 102 includes the projected revenue analysis engine 270 configured to analyze historical payment patterns, for example obtained from the payment trends analysis engine 239, in view of recent claims to estimate revenue metrics. The revenue metrics, in some examples, may include remittance by payer, remittance by upcoming revenue cycle, remittance by service type (e.g., billing codes category), and/or remittance by location. The revenue metrics may be refined, in another example, to provide more detailed metrics such as, in some examples, remittance by payer by location and/or remittance by service type by revenue cycle. The metrics derived by the projected revenue analysis engine 270, in some embodiments, depend upon content requested by an end user (e.g., representative of a medical provider) for organization in a spreadsheet, a table, or a report. In some embodiments, the metrics derived by the projected revenue analysis engine 270 depend in part on a type of end user. For example, an emergency medical transportation service provider may desire different metrics than a surgical center service provider. In some embodiments, the projected revenue analysis engine 270 supplies requested metrics to a report generation engine 278 for further processing.

In some implementations, the predictive analytics platform 102 includes a procedure trends analysis engine 272 configured to analyze historic claims data for patients who underwent major procedures, such as surgical procedures, to identify patterns within the claims data near the time of the procedure and shortly thereafter (e.g., days, 1 week, weeks, 1 month, or up to multiple months) that may be indicative of follow-on services and/or prescription products commonly associated with the major procedure. The patterns, in some examples, may include services commonly paired with each major procedure, common follow-on services to each major procedure, and/or prescriptions commonly paired with each major procedure. Further, the patterns may be broken down into subsets, such as services commonly paired with each major procedure by demographic group (e.g., age range, gender, race), services commonly paired with each major procedure by patient prescription (e.g., certain prescriptions may be indicative of a more serious condition, such as more serious chronic heart failure), common follow-on services to each major procedure by demographic group, services commonly paired with each major procedure by patient co-morbidity (e.g., high blood pressure, diabetes, cancer, congestive heart failure, obesity, etc.), and/or common follow-on services to each major procedure by co-morbidity. In some embodiments, the procedure trends analysis engine 272 applies machine learning analysis, cluster analysis, and/or statistical data analysis to historic claims data (e.g., the historic claims data 256) to identify data patterns within the accessed records. For example, the procedure trends analysis engine 272 may include different machine learning classifiers trained to identify patterns related to the various sets and subsets of procedures and patient demographics and/or medical history. The machine learning classifiers, for example, may be trained using de-identified data collected over a period of time (e.g., at least 3 months, from 3 to 6 months, up to 1 year, 2 years, etc.). The scope of the training data, for example, may depend upon an amount of data available related to the different variables (e.g., an amount of data per major procedure, an amount of data per age range, etc.). The procedure trends analysis engine 272 may return one or more sets of data patterns for analysis, for example by a projected procedure analysis engine 274.

In some implementations, the predictive analytics platform 102 includes the projected procedure analysis engine 274 configured to analyze historical major procedure service pairing patterns, for example obtained from the procedure trends analysis engine 272, in view of recent claims to estimate projected additional claims. The projected additional claims, in some examples, may include estimated incoming claims by time period, estimated incoming claims by revenue cycle, estimated incoming claims by service type (e.g., billing codes category), and/or estimated incoming claims by location. The projected additional claims may be refined, in another example, to provide more detailed metrics such as, in some examples, incoming claims by service type by location and/or incoming claims by service type by revenue cycle. The claims projections derived by the projected procedure analysis engine 274, in some embodiments, are provided to the payment pattern application engine to determine projected revenue based upon anticipated future claims. In some embodiments, the claims projections are automatically analyzed to better anticipate ordering needs for medical equipment and other products associated with the projected services, staffing needs for the projected services, and/or potential mitigation options to better support the patient in avoiding certain follow-on claims, such as sepsis.

In some implementations, the predictive analytics platform 102 includes the report generation engine 278 configured to organize historic and/or forecast metrics such as revenue metrics 264 and remittance metrics 266 and prepare presentations related to the metrics. The report generation engine 278, for example, may combine forecast metrics with historic metrics (e.g., past revenue quarters plus one or more future revenue quarters) to visually present revenue trends over time. Further, the report generation engine 278 may generate tables, charts, bar graphs, line graphs, and/or other graphical displays to visually represent comparisons in the forecast metrics and/or between the historic metrics and the forecast metrics.

In some implementations, the predictive analytics platform 102 includes a coverage coordination analysis engine 276 for coordinating benefits coverage between multiple payers available to the patient. The coverage coordination analysis engine 276, for example, may coordinate benefits based on a legal or administrative hierarchy, such as the coordination of benefits (COB) responsibilities published by the United States Centers for Medicare & Medicaid Services (CMS), the Coordination of Benefits Model Regulation by the National Association of Insurance Commissioners (NAIC), and/or U.S. statutes directed to federal employees' health benefits regulations. For example, the coverage coordination analysis engine 276 may apply rules to determine an order of benefits application (e.g., coordination of benefits rules) based upon a well-known hierarchy. Further, the coverage coordination analysis engine 276 may apply rules regarding if and when different types of coverage go into effect, such as liability coverage. The coverage coordination analysis engine 276, based upon the rules, in some embodiments, provides a percentage of each service covered by each of the available payers, an estimated amount to invoice to each of the available payers, and/or a hierarchical order in which to approach the available payers for reimbursement. Further, in some embodiments, the coverage coordination analysis engine 276 determines a confidence rating or confidence level associated with the coverage coordination determination.

FIGS. 3A through 3D are flow charts of an example method 300 and sub-methods 310, 320, and 330 for calculating a combined payment estimate by applying historic patient payment patterns and historic payer payment patterns to a present medical claim. The payment estimation may include contributions from one or more payer sources. Portions of the method 300 and/or sub-methods 310, 320, and 330 may be performed by the predictive analytics platform 102 of FIG. 1A interfacing with various data records 120, 122, 124 and/or 126 of the data universe 104. The method 300 and sub-methods 310, 320, and 330 may be performed by or on behalf of a medical service provider, such as the providers described in relation to FIG. 1A. For example, the method 300 and sub-methods 310, 320, and 330 may be performed responsive to the revenue inquiry 112*a* submitted at the revenue maximizer portal 110 of FIG. 1A.

In some implementations, the method 300 begins with obtaining patient information and service information (302). The patient information and service information may be obtained and may include similar information, for example, as described in relation to the patient demographic data 116 and the procedure codes 114 of FIG. 1A. In another example, the patient information and service information may be received as part of a medical claim as described in relation to operation 152 of the method 150 of FIG. 1B.

In some implementations, if no payer has been identified within the incoming information (304), known information is used to search for one or more payers within patient records (306). For example, the patient information may be applied to looking up patient records maintained by the service provider to identify previously applied coverage.

If a payer is not found within the patient information or the medical provider system (308), in some implementations, a payer identification process is conducted (310) to identify one or more payers providing active coverage to the patient.

FIG. 3B illustrates a method 310 (e.g., a sub-method of method 300) for identifying one or more payers providing active coverage to a patient. The method 310, for example, may correspond to the payer identification engine 218 of the predictive analytics platform 102 as described in relation to FIG. 2.

Turning to FIG. 3B, in some implementations, the method 310 begins with obtaining the patient information and the service information (332). At least a portion of the information provided at operation 302 of FIG. 3A, for example, may be passed to the sub-method 310.

In some implementations, using patient demographic information, one or more most likely payers are determined (334). The geographic region, employment status, disability status, and/or age range of the patient, in some examples, may be indicative of one or more most likely payers. For example, a retired or elderly patient may be more likely covered by a federal payer program, while an employed adult (or child thereof) may be more likely covered by a private insurance company popular within the region (e.g., state, zip code, etc.). In some embodiments, most likely payers are identified based on performing machine learning or other probability analysis of patient demographic data cross-referenced with payer identifications for the patients (and guarantors thereof) to identify most likely payers per demographic grouping. The analysis, for example, may be performed on a periodic basis, such as annually, and the resultant matches of payers to demographic groupings may be maintained by the predictive analytics platform 102 for future reference. The most likely payer(s), additionally, may be identified based on the service information, because those payers providing coverage for the medical service may be the only payers relevant to the payer search.

In some implementations, for each of the most likely payers, patient status is confirmed through connecting with the payer system (336). The coverage verification engine 216 of FIG. 2, for example, may perform confirmations for each of the most likely payers.

If active coverage is confirmed for a payer (338), in some implementations, patient record information is requested from the payer (340). For example, the coverage verification engine 216 requests patient record information from the payer or receives patient record information automatically with the affirmative response from the payer system.

In some implementations, the system record is updated with any changes in or addition to patient information (342). For example, the demographic verification engine 214 may update patient data 240 in local records of the medical provider.

In some implementations, while additional payer candidates have not yet been confirmed (344), the operations 336 through 342 are repeated.

In some implementations, if no payer has been located (345), a lack of insurance status is returned (346). If, instead, at least one payer has been located (345), in some implementations, the method 310 determines whether multiple payers have been located (347). If only one payer has been located, the payer information is returned (349). For example, the payer information may be returned to the method 300.

If multiple payers are available (347), in some implementations, the payers are ranked in an order of preference (348). For example, the payer preference identification engine 220 of FIG. 2 may rank the payers in order of preference. Preference may be based at least in part on the service information and/or the coordination of benefits rules discussed above.

In some implementations, the ranked payer information is returned (349).

Although described as a particular series of operations, in some embodiments, more or fewer steps may be included in the method 310. For example, ranking payers in order of preference (348) may be performed at a later time, once plan information has been identified (e.g., FIG. 3A step 318) such that plan information may be analyzed in view of the service information or other claim features. In another example, rather than or prior to connecting with individual payer system(s) (336), an insurance information clearinghouse may be contacted to identify whether the patient is covered under a number of different coverage programs. In further embodiments, certain steps of the sub-method 310 may be performed in a different order or in parallel. For example, multiple payer systems may be contacted in parallel to confirm active coverage. Other modifications of the sub-method 310 are possible.

Returning to FIG. 3A, in some implementations, if at least one payer has been identified (314), payer plan benefit information is accessed (318). The payer plan benefit information may be accessed, for example, from the payer data 126 of FIG. 1A or the plan data 244 of FIG. 2. If not immediately accessible, in some embodiments, one of the benefits information sources 208 of FIG. 2 may be automatically contacted to obtain up-to-date plan information related to the payer benefits plan.

In some implementations, if the service is covered by at least one of the payers (319) a payer reimbursement estimation process is conducted (320) to anticipated payer reimbursement.

Figure 3C:
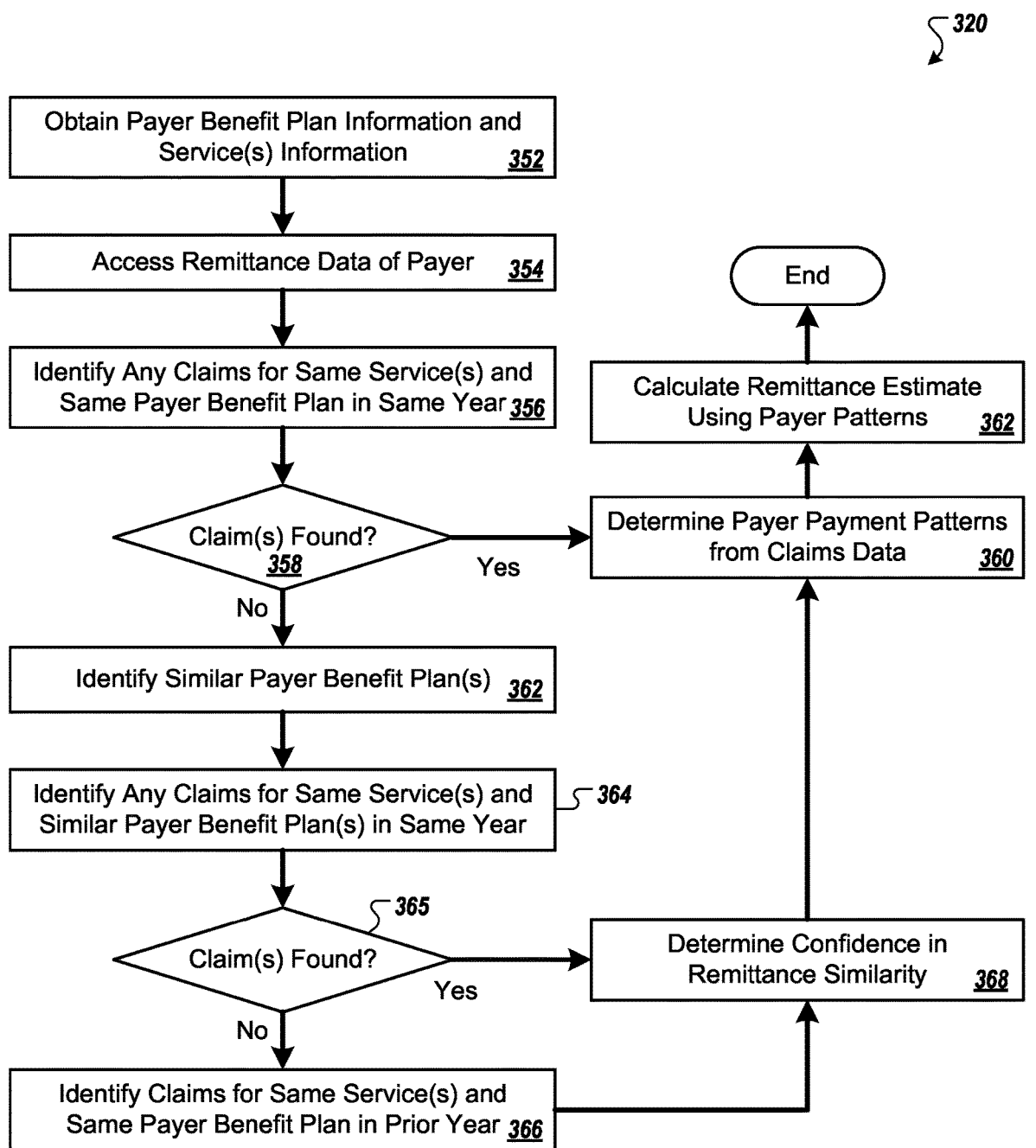

FIG. 3C illustrates a method 320 (e.g., a sub-method of method 300) for estimating payer reimbursement one or more payers providing active coverage to a patient. The method 320, for example, may correspond to the payer payment pattern engine 222 of the predictive analytics platform 102 as described in relation to FIG. 2.

Turning to FIG. 3C, in some implementations, the method 320 begins with obtaining payer benefit plan information and services information (352). At least a portion of the services information provided at operation 302 of FIG. 3A, for example, may be passed to the sub-method 310. Further, the payer benefit plan information identified at operation 318 of FIG. 3A may be provided to the sub-method 310 from the method 300.

In some implementations, remittance data of the payer is accessed (354). The remittance data, for example, may include reimbursements from payers related to historic claims and may be included in the claims data (e.g., as one or more fields of a database of claims records identifying remittance received) or maintained separate from the claims data. For example, the historic claims data 120 may be accessed by the predictive analytics platform 102 as described in relation to FIG. 1A. In another example, the payer payment pattern engine 222 may access the remittance data 268 from the data repository 210.

In some implementations, any historic claims for the same service(s) as those identified in the service(s) information and for the same plan as identified in the payer benefit plan for the same year (e.g., calendar year or payer plan year) are identified (356). The historic claims, for example, may include claims having same sets of overlapping product and/or service codes. In another example, the historic claims may include individual sets of claims, each identified as being related to one of a set of produce and/or service codes provided in the service(s) information. In some embodiments, the historic claims include claims already reimbursed (e.g., including remittance amounts from the payer under the payer plan). In some embodiments, the historic claims additionally include rejected claims (e.g., claims in which the payer, rather than responding with reimbursement funds, responded with a refusal to pay). Rejected claims, in some examples, may include billing codes not covered by the payer plan and/or billing codes requiring prior authorization to qualify for coverage under the payer plan.

In some implementations, if historic claims are identified (358), payer payment patterns are determined using the claims data for the historic claims 360). The payer payment pattern engine 222, for example, may analyze the historic claims data to derive one or more payer payment patterns related to claims reimbursement for the products and/or services. For example, a separate payment pattern may be determined for each product and/or service within the service(s) information.

In some implementations, a remittance estimate is calculated using the payer payment patterns (360). The payer payment pattern(s), for example, may be provided to the payment pattern application engine 226 of FIG. 2 to calculate an estimated payment in the present circumstance based upon the payer payment pattern(s) determined for past medical claims including the service(s). The remittance estimate may be provided to the method 300 of FIG. 3A.

Although described as a particular series of operations, in some embodiments, more or fewer steps may be included in the method 320. For example, a confidence in remittance similarity may be calculated for claims even when they include the same benefit plan and the same year, for example based upon a range of values within the historic data, a number of historic claims identified, and/or at least one refused claim within the historic data. In further embodiments, calculating the remittance estimate may include calculating a confidence level in the estimate (368). The confidence level in the estimate, for example, may replace or refine the calculated confidence level in remittance similarity. In further embodiments, certain steps of the method 320 may be performed in a different order or in parallel. For example, claims for the same services and similar payer benefits plans (364) may be identified in parallel with, or after, identifying claims for the same services and same payer benefit plan in the prior year (366), depending upon confidence levels associated with each type of data (e.g., in view of the service/product, the plan type, etc.). Other modifications of the method 320 are possible.

Returning to FIG. 3A, in some embodiments, the estimated reimbursement is refined using patient information (322). For example, the plan benefit information accessed at operation 318 may include copay and/or deductible information which may be deducted from a total funds attributed to payer reimbursement. In another example, the estimated reimbursement may be refined based on funds remaining in the patient's deductible, for example using information returned upon verifying coverage for the patient (312).

In some implementations, a residual balance is determined (324). The residual balance 324, for example, may include the copay and/or deductible owed by the patient. For example, the residual balance 324 may include any portion of the services not covered by the payer. For example, out of multiple services provided, one or more services may not be covered by the payer.

If a residual balance exists, in some implementations, a patient likelihood to pay estimation process is conducted (330) to anticipated payer reimbursement.

FIG. 3D illustrates a method 330 (e.g., a sub-method of method 300) for estimating a likelihood of receiving remittance from the patient for the residual balance. Portions of the method 330, for example, may be performed by the patient likelihood to pay analysis engine 228, the payment pattern application engine, and/or the patient payment pattern engine 224 of the predictive analytics platform 102 as described in relation to FIG. 2.

In some implementations, the method 330 begins with obtaining patient information and the estimated cost to the patient (372). The method 300, for example, may provide the patient information and the residual balance to the method 330.

In some implementations, a medical debt credit score of the patient is accessed (374). The medical debt credit score, for example, may be automatically obtained by the patient likelihood to pay analysis engine 228 of FIG. 2 from an external credit rating organization. The medical debt credit score may be a score, rating, or relative likelihood to pay based upon a current level of medical debt.

In some implementations, payment trends are identified using the debt score and historic claims information (376). For example, the patient payment pattern engine 224 of FIG. 2 may identify payment trends corresponding to remittance outcomes related to claims of insured persons similar to the patient. The similar insured persons, for example, may be identified by the patient matching engine 230 of FIG. 2. The similar insured persons may match based on debt score or debt score range. Further, in some embodiments, the similar insured persons may match based on demographic information or other information related to the patient, as described in relation to the patient payment pattern engine 224 of FIG. 2. In a particular example, the similar insured persons may match based in part on an expense range of the estimated cost. In illustration, a smaller amount (e.g., hundreds of dollars) may be more likely to be reimbursed, all other information being substantially equal, than a very large medical expense (e.g., tens of thousands of dollars).

In some implementations, the payment trends are analyzed to determine a likelihood of the patient to pay the estimated cost (378). For example, the actual outcomes may be statistically combined to reach an estimated payment level corresponding to the estimated cost. The payment pattern application engine 226 of FIG. 2, for example, may apply the patient payment pattern to determining the estimated payment level.

Although described as a particular series of operations, in some embodiments, more or fewer steps may be included in the method 330. For example, payment trends may be analyzed in view of each service or product where there is a collection of services and/or products which may not identically match historical claims data. In another example, a confidence level in the likelihood of the patient to pay the estimated cost may be determined. The confidence level, in some examples, may consider the similarity between the patient and the insured individuals' information used in determining the patient payment pattern, a diversity in payments across the insured individuals included in the patient payment pattern, and/or additional financial data regarding the individual. The additional financial data, in some examples, can include a level of funding of a health savings account or other flexible spending account, a federal poverty level (FPA) percentage, and/or other liens or financial obligations of the patient (or guarantor thereof). In further embodiments, certain steps of the method 330 may be performed in a different order or in parallel. For example, the medical debt credit score may already be available. Other modifications of the method 330 are possible.

Returning to FIG. 3A, in some implementations, a total estimated recovery is calculated (331). A portion of the residual balance likely to be paid by the patient based upon the estimated likelihood to pay may be calculated. If the likelihood is presented as a percentage, for example, the percentage may be directly applied to the residual balance. The refined estimated payer reimbursement may be added to the portion of the residual balance to obtain the total estimated recovery.

Returning to operation 314, if no payer information is identified, a service cost to the patient may be determined (316). For example, although the service coverage often includes an amount negotiated for reimbursement by the payer, a basic cost to the patient may differ from that value. Thus, the service cost may be calculated to determine an amount charged to the patient in the event no insurance is available.

The patient likelihood to pay the service cost may be estimated (330). In this branch of calculations, the likelihood estimation may be provided to calculating the total estimated recovery based on patient payment alone (331).

Although described as a particular series of operations, in some embodiments, more or fewer steps may be included in the method 300. For example, in addition to calculating the total estimated recovery (331), a total confidence in the estimate may be determined (e.g., based upon a patient portion confidence level and a payer portion confidence level). In another example, the service cost may be determined (316) prior to identifying the payer in circumstances where a same cost is applied regardless of payment source. In further embodiments, certain steps of the method 300 may be performed in a different order or in parallel. Other modifications of the method 300 are possible.

Figure 4A:
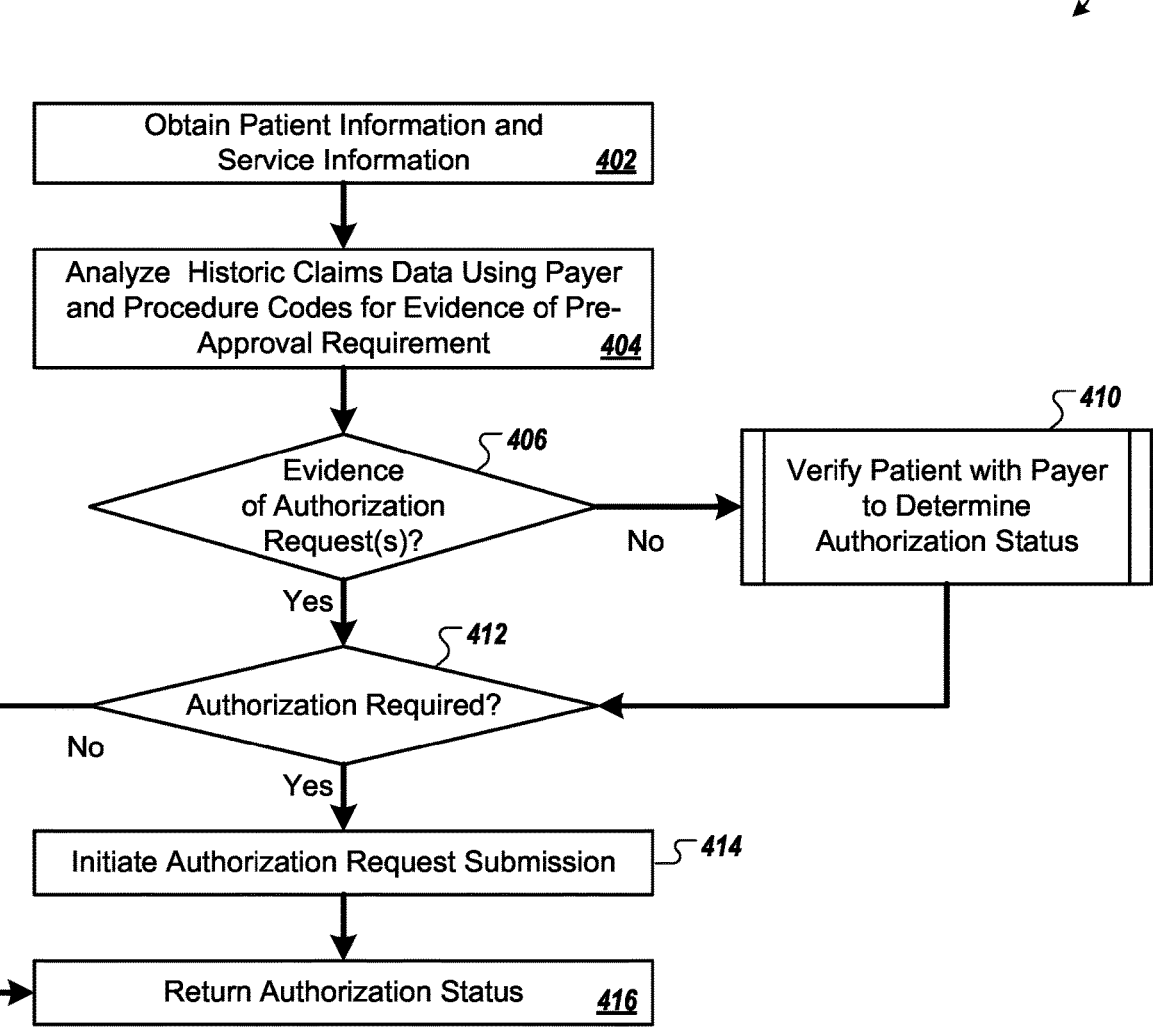
FIG. 4A and FIG. 4B are flow charts of an example method and sub-method for anticipating necessity of medical procedure prior authorization through performing machine learning analysis.
Figure 4B:
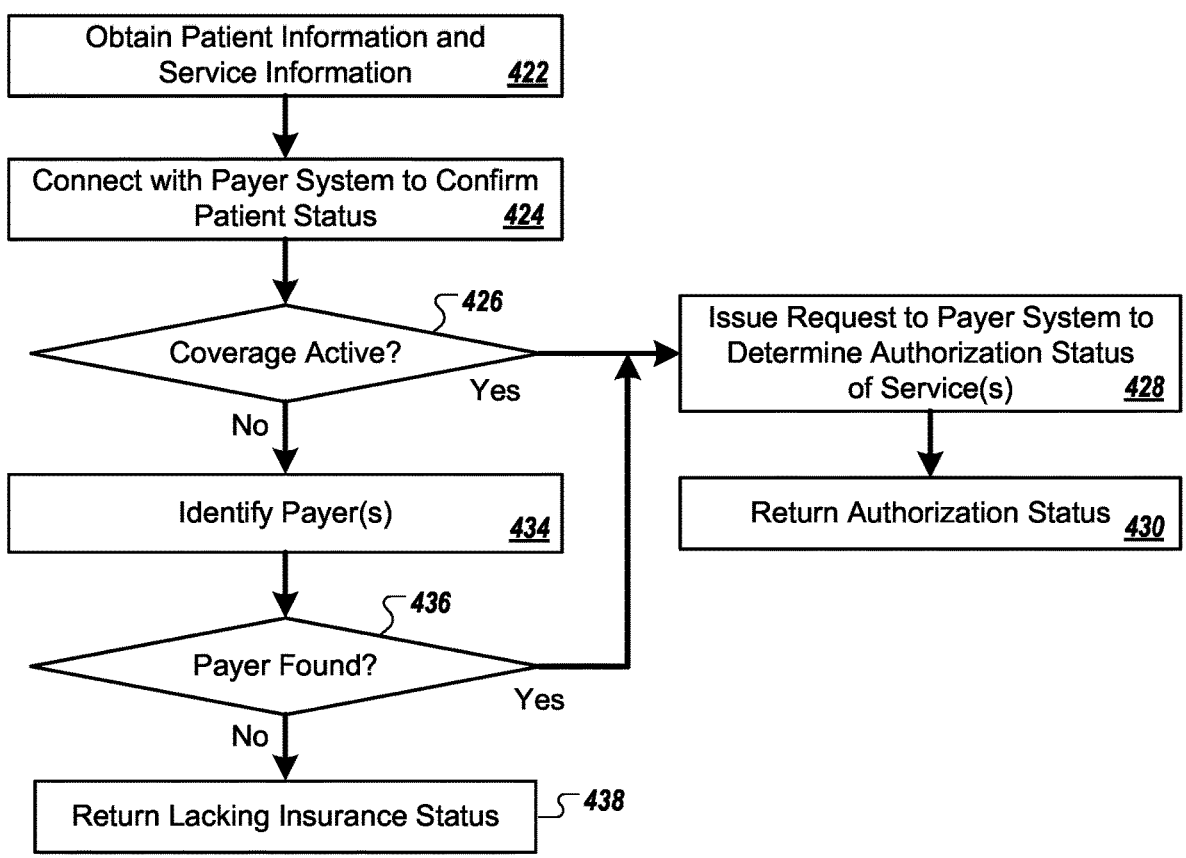

FIGS. 4A and 4B are flow charts of an example method 400 and sub-method 410 for anticipating necessity of medical procedure prior authorization through performing machine learning analysis on historic claims data. Portions of the method 400 and/or the sub-method 410 may be performed by the predictive analytics platform 102 of FIG. 1A interfacing with various data records 120, 122, 124 and/or 126 of the data universe 104. The method 400 and sub-method 410 may be performed by or on behalf of a medical service provider, such as the providers described in relation to FIG. 1A. For example, the method 400 and sub-method 410 may be performed responsive to the prior authorization inquiry 112c submitted at the revenue maximizer portal 110 of FIG. 1A. In another example, the method 400 and sub-method 410 may be performed at least in part by the payer pre-approval analysis engine 232 of FIG. 2.

In some implementations, the method 400 begins with obtaining patient information and service information (402). The patient information and service information may be obtained and may include similar information, for example, as described in relation to the patient demographic data 116 and the procedure codes 114 of FIG. 1A. In another example, the patient information and service information may be received as part of a medical claim as described in relation to operation 152 of the method 150 of FIG. 1B.

In some implementations, historic claims data is analyzed using payer and procedure codes for evidence of a pre-approval requirement (404). The historic claims data, for example, may be analyzed by the payer pre-approval analysis engine 232 of FIG. 2.

In some implementations, if, based on the analysis, evidence is identified that authorization requests are needed (406), a patient verification process is conducted (410) to determine authorization status.

FIG. 4B illustrates a method 410 (e.g., a sub-method of the method 400) for determining authorization status of a patient based on active payer coverage. Portions of the method 410, for example, may be performed by the payer pre-approval analysis engine 232, the payer pre-approval request engine 234, the coverage verification engine 216, and/or the payer identification engine 218 of FIG. 2.

Turning to FIG. 4B, in some implementations, patient information and service information is obtained (422). The patient information and service information, for example, may be obtained from the method 400 (e.g., as received by the method 400 in operation 402).

In some implementations, patient status is confirmed by connecting with a payer system (424). The status may be confirmed, for example, as described in relation to operation 336 of the method 310 of FIG. 3B.

In some implementations, if coverage is active (426), a request is issued to the payer system to determine authorization status of the service(s) (428). For example, the payer pre-approval analysis engine 232 and/or the payer pre-approval request engine 234 may automatically connect to the payer system to confirm that the patient requires pre-authorization for the service(s).

In some implementations, the authorization status is returned (430). The authorization status (e.g., needs pre-approval or does not need pre-approval), for example, may be returned to the method 400.

If, instead, coverage is not active (426), in some implementations, one or more payers is identified (434). The payer(s) may be identified, for example, using the method 310 of FIG. 3B.

In some implementations, if a payer is identified (436), the method 410 proceeds with issuing a request to the payer system to determine authorization status of the service(s) (428) and returning authorization status (430), as described above.

If, instead, no payer is identified (436), in some implementations, a status of patient lacking payer coverage is returned (438). The status, for example, may be returned to the method 400.

Although described as a particular series of operations, in some embodiments, more or fewer steps may be included in the method 410. For example, the patient status with the payer may be confirmed prior to executing the method 410 (e.g., before analyzing the historic claims data in the method 400 of FIG. 4A). In another example, authorization status and patient confirmation status (operations 424 and 428), for at least some payers, may be accomplished through a single contact to the payer system. In further embodiments, certain steps of the method 410 may be performed in a different order or in parallel. Other modifications of the method 410 are possible.

Returning to FIG. 4A, in some implementations, if authorization is required (412) an authorization request submission is initiated (414). The payer pre-approval request engine 234 of FIG. 2, for example, may submit the authorization request.

In some implementations, whether or not authorization was determined to be required (412), the authorization status (or lack of payer coverage status as described in relation to operation 438 of FIG. 4B) is returned (416).

Although described as a particular series of operations, in some embodiments, more or fewer steps may be included in the method 400. For example, instead of or in addition to analyzing historic claims data (404), historic service request data may be analyzed to identify evidence of pre-authorization requests. In some embodiments, rather than automatically initiating the authorization request submission (414), the method provides the authorization status to a user for review. For example, the user may review the authorization status and confidence level/confidence rating to decide whether to pursue pre-authorization. In further embodiments, certain steps of the method 400 may be performed in a different order or in parallel. Other modifications of the method 400 are possible.

Figure 5A:
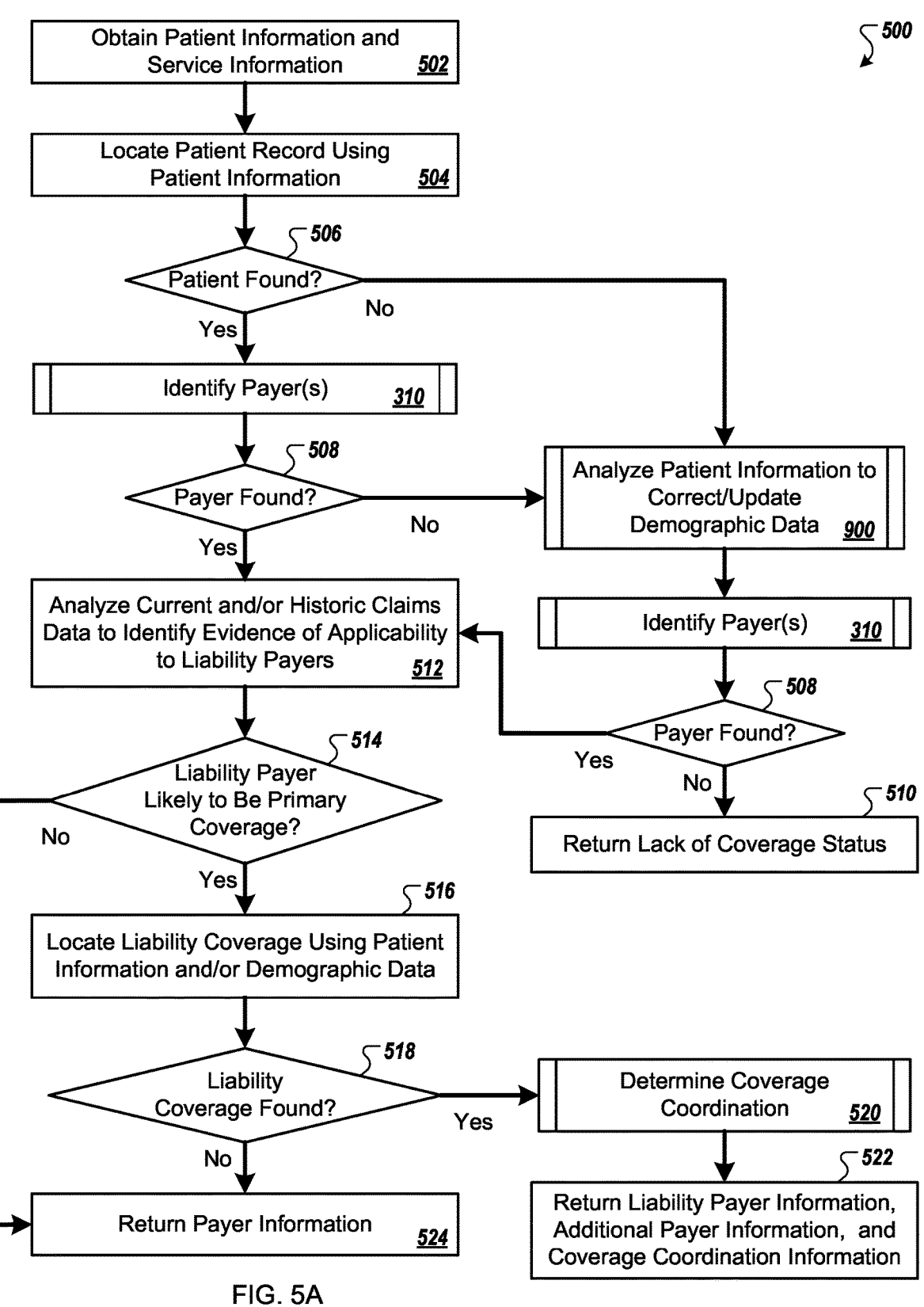
FIG. 5A and FIG. 5B are flow charts of an example method and sub-method for identifying applicability of liability insurance to a medical claim and identifying appropriate payer(s) thereof.
Figure 5B:
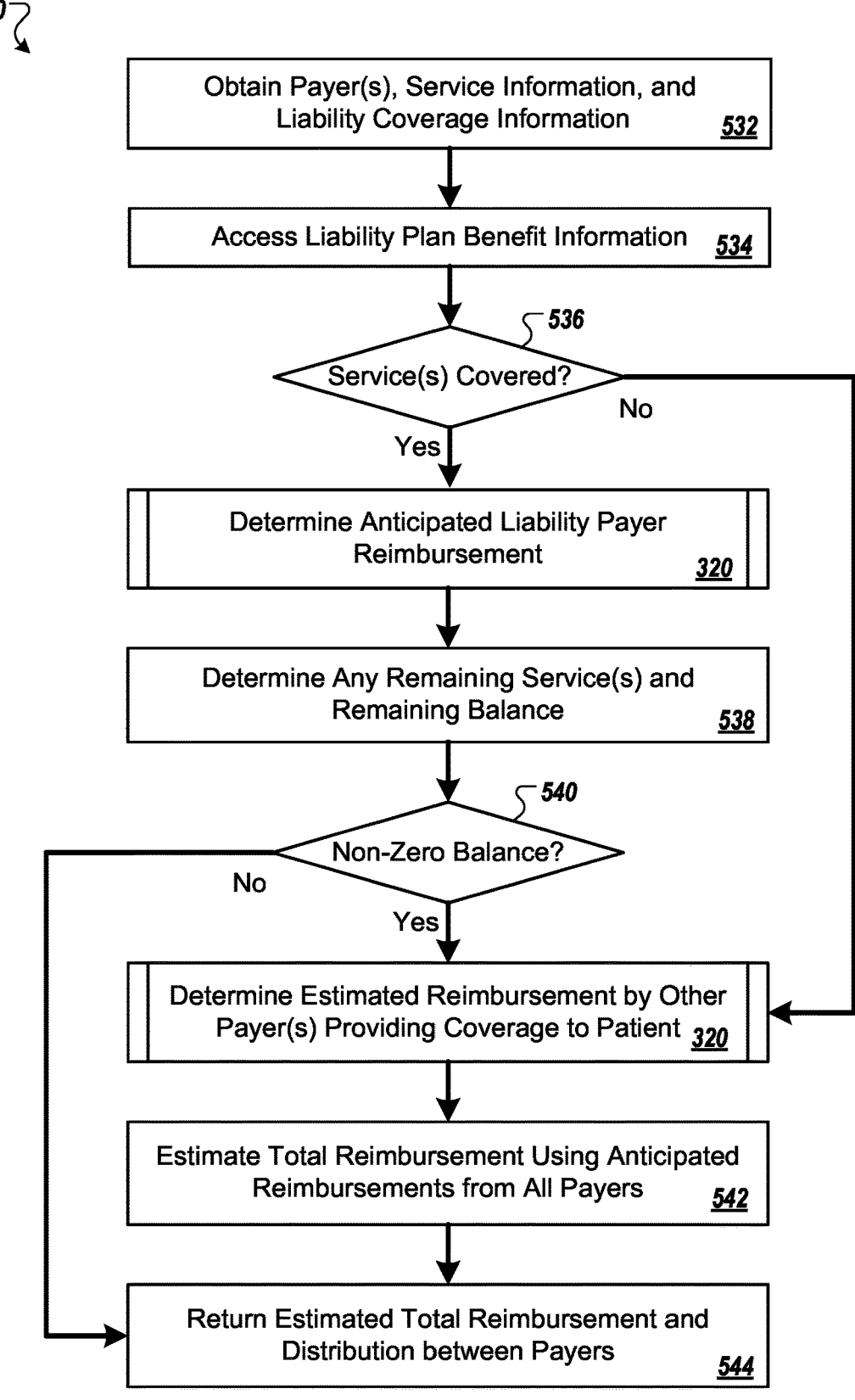

FIGS. 5A and 5B are flow charts of an example method 500 and sub-method 520 for identifying applicability of liability insurance to a medical claim and identifying appropriate payer(s) thereof. Portions of the method 500 and/or the sub-method 520 may be performed by the predictive analytics platform 102 of FIG. 1A interfacing with various data records 120, 122, 124 and/or 126 of the data universe 104. The method 500 and sub-method 520 may be performed by or on behalf of a medical service provider, such as the providers described in relation to FIG. 1A. For example, the method 500 and sub-method 520 may be performed responsive an inquiry submitted at the revenue maximizer portal 110 of FIG. 1A. In another example, the method 500 and sub-method 520 may be performed at least in part by the liability applicability analysis engine 235 of FIG. 2.

In some implementations, the method 500 begins with obtaining patient information and service information (502). The patient information and service information may be obtained and may include similar information, for example, as described in relation to the patient demographic data 116 and the procedure codes 114 of FIG. 1A. In another example, the patient information and service information may be received as part of a medical claim as described in relation to operation 152 of the method 150 of FIG. 1B.

In some implementations, a patient record is located using the patient information (504). The patient record, for example, may be part of the service provider data 252 (e.g., locally stored records regarding current patients). Further, the patient record may be located via patient data 240 of FIG. 2, including, for example, data networked to the service provider (e.g., via a release form from a different service provider).

If the patient is identified (506), in some implementations, a payer identification process is executed (310) to identify one or more payers providing active coverage to the patient. Payers may be identified as described in relation to the method 310 of FIG. 3B.

In some implementations, if no payer is identified (508), a patient information analysis process is executed to correct and/or update patient demographic data (900).

FIG. 9 illustrates a method 900 (e.g., a sub-method of the method 500) for correcting and/or updating patient demographic data provided to the system (e.g., a service provider or the predictive analytics platform 102 of FIG. 1A). Portions of the method 900, for example, may be performed by the patient information updating engine 236 of FIG. 2.

Turning to FIG. 9, in some implementations, initial patient demographic data is obtained from a first data source (902). For example, the method 500 may provide the patient information obtained at operation 502 of FIG. 5A. The initial patient demographic data may be obtained, for example, as part of patient intake or an electronic medical chart. While during a typical office visit, office personnel may have the opportunity to obtain a full set of demographic information from the patient and compare that information to patient information on record to determine whether the patient is already entered in the system. However, in the circumstance of an emergency, few details may be known regarding the patient. For example, for a patient experiencing shock or other trauma, few details may be gleaned from the patient. Further, the information provided may have been misunderstood by service provider personnel or misspelled.

In some implementations, the initial patient demographic data is analyzed in view of identification criteria to determine whether the initial patient demographic data is sufficient for uniquely identifying the patient (904). The initial patient demographic data may include at least a portion of basic demographic information such as, in some examples, first and last name, at least a portion of an address, birth date, phone number, and gender. The criteria, for example, may involve a set of rules, each rule corresponding to one or more demographic fields that, alone or in combination, may be sufficient for uniquely identifying a patient. For example, social security number alone is a uniquely identifying data element, but first and last name alone are rarely a unique combination. In the circumstance of fairly common names, a name plus a birth date may also be insufficient. However, a name, birth date, and zip code may be deemed sufficient information for uniquely identifying the patient.

In some implementations, the initial patient demographic data is compared to known patient demographic data (906). For example, the initial patient demographic data may be compared to one or more local records, such as patient data 240 maintained by the predictive analytics platform 102 (e.g., a subset of the patient data 240 belonging to a particular service provider or other non-de-identified patient data) to determine if there are any inconsistencies or ambiguities between the information. For example, the provided information may differ in one or more elements from the stored patient information, such as, in some examples, current address, spelling of the first name, spelling of the last name, and/or date of birth. The patient information updating engine 236, for example, may apply fuzzy logic to identify close to but unmatched spellings in certain fields of demographic data (e.g., patient name, street name, city name, etc.).

In some implementations, if the initial patient demographic data is deemed insufficient (908) and/or there are ambiguities/contradictions in the initial patient demographic data (910), one or more portions of the initial patient demographic data are used to access at least one additional data source to supplement the initial patient demographic data (912). The additional data source(s), for example, may include the payer of the patient's primary coverage, a credit reporting agency, and/or a financial institution.

In some implementations, if the patient is located via additional sources (914) the data from the additional source(s) is used to supplement the missing information and/or to resolve any ambiguities and/or contradictions within the initial patient demographic data (916). For example, the patient information updating engine 236 of FIG. 2 may update the patient data 240 to reflect the information retrieved from the additional data source(s). The data may replace the initial patient demographic data. In other embodiments, the newly identified data may be added to the patient data record such that the initial patient demographic data is retained (e.g., for purposes for matching with additional information coming from the electronic patient chart which has not been updated, etc.).

If, instead, the patient is not located via additional source(s) (914), in some implementations, data warning(s) are flagged in the initial patient demographic data (918).

Although described as a particular series of operations, in some embodiments, more or fewer steps may be included in the method 900. For example, rather than automatically supplementing the missing information (916), the method 900 may first present the additional demographic data to a representative of the medical provider to receive manual confirmation prior to updating the patient data. In further embodiments, certain steps of the method 900 may be performed in a different order or in parallel. For example, in other embodiments, it is determined whether sufficient data is available (904) prior to comparing for ambiguities and/or contradictions (906) so that the comparison (906) can compare information from the additional data sources (912) as well. Other modifications of the method 900 are possible Returning to FIG. 5A, in some implementations, the payer identification process is executed (310) again, using the corrected and/or updated patient demographic data, to identify one or more payers providing active coverage to the patient.

If no payer is found on the second round of identification (508), in some implementations, a lack of coverage status is returned (510). The lack of coverage status, for example, may be provided to a requesting medical provider.

If, instead, a payer is found on the second round of identification (508), in some implementations, current and/or historic claims are analyzed to identify evidence of applicability to liability payers (512). For example, the liability applicability analysis engine 235 may analyze claims data 256, service request data 260, and/or service provider data 252 to identify evidence of applicability to liability payers, as described in relation to FIG. 2.

If it is determined that a liability payer is likely to be considered as primary coverage for at least one of the services (514), in some implementations, liability coverage is located using the patient information and/or updated demographic data (516). The payer identification engine 218 of FIG. 2, for example, may locate liability coverage associated with the patient. In other embodiments, an additional engine may be designed to identify liability coverage, because liability providers are not as readily identified as traditional payers, lacking automated coverage confirmation processes. For example, many liability payers supply, upon request and/or periodically, listings of active coverage holders, such as a spreadsheet with records identifying policy holders by name and other identifying information. The predictive analytics platform 102, for example, may store the liability provider files as part of the payer data 242 of FIG. 2. The predictive analytics platform 102 may periodically request updated files to ensure reliability of information. The information may be considered to be reliable, in some examples, if it is less than a month old, less than three months old, up to six months old, or no older than a year from access. The age of the file (if another file cannot be obtained in real-time), in some embodiments, is applied to determine a confidence level or confidence rating associated with the liability payer.

If liability coverage is identified (518), in some implementations, a coverage coordination determination process is executed (520).

FIG. 5B illustrates a flow chart of an example method 520 for determining coverage coordination for allocating reimbursement among multiple available payers to the patient.

Portions of the method 520, for example, may be performed by the coverage coordination analysis engine 276 of FIG. 2.

Turning to FIG. 5B, in some implementations, the method 520 begins with obtaining one or more active payers available to the patient, service information regarding services and/or products provided to the patient, and liability coverage information regarding a liability payer potentially responsible for reimbursement for at least a portion of the product(s) and/or service(s) (532). The information, for example, may be obtained from the method 500 of FIG. 5A (e.g., the service information obtained at operation 502, the payers identified by method 310 of FIG. 3B, and the liability payer located at operation 516).

In some implementations, liability plan benefit information is accessed (534). The benefit information, for example, may be obtained from the plan data 244 of the data repository 210 of FIG. 2. If the plan data 244 is not locally available, the liability provider's computer system may be automatically contacted to obtain a copy of the liability plan benefit information. Since the data request method often differs between liability coverage providers, a contact method may be looked up (e.g., in the payer data records 242 of the data repository 210 of FIG. 2) prior to contacting the liability payer's system.

In some implementations, if at least one of the services and/or products identified in the service information are covered by the liability plan (536), an anticipated liability payer reimbursement is determined (320). For example, the method 320 of FIG. 3C may be invoked to estimate coverage by the liability payer in view of historic claims data. In another example, the anticipated liability payer reimbursement is determined at least in part based upon payer plan information such as, in some examples, a patient deductible level and a maximum reimbursement value. Further, the liability payer system may be automatically contacted to determine current information regarding the patient's plan, such as a current deductible remaining.

In some implementations, remaining services and a remaining balance are determined (538). For example, the liability payer may only cover a portion of the services provided to the patient. In this circumstance, the liability reimbursement may be applied to only those products and/or services applicable to liability reimbursement. Additionally, the liability payer may not cover the entire cost of one or more services. For each of these reasons, a balance may remain after applying the estimated liability payer remittance.

In some implementations, if a remaining balance exists (540) or if it was previously determined that the service(s) are not covered by the liability plan (536), an estimated reimbursement value is determined through analyzing other payers providing active coverage to the patient (320). For example, the method 320 of FIG. 3C may be invoked to estimate coverage by the liability payer in view of historic claims data.

In some implementations, a total reimbursement is estimated using the anticipated reimbursements from all payers (542). The total reimbursement may include a total estimated dollar value determined through combining values associated with each payer (e.g., liability payer, primary insurance, Medicare, Medicaid, etc.). The total reimbursement may additionally include a confidence level or confidence rating associated with the estimate.

In some implementations, the total estimated reimbursement and the distribution of coverage between the payers is returned (544). For example, the estimate may be returned to the method 500 of FIG. 5A. In another example, the estimate may be presented or electronically communicated to a representative of the service provider.

Although described as a particular series of operations, in some embodiments, more or fewer steps may be included in the method 520. For example, a single call to a process such as the method 320 may be used to determine reimbursement by all payers, including the liability payer. In another example, rather than estimating a total reimbursement, the method may instead determine an estimated portion of reimbursement associated with each payer (e.g., Service A at X %, Service B at Y %, etc.). In further embodiments, certain steps of the method 520 may be performed in a different order or in parallel. Other modifications of the method 520 are possible.

Returning to FIG. 5A, in some implementations, liability payer information, other payer information, and coverage coordination details are returned (522). The information, for example, may be presented or electronically communicated to a representative of the service provider.

Returning to operation 506, if the patient is not found (506), in some implementations, the patient information analysis process is executed to correct and/or update patient demographic data (900), and the payer identification process is executed only once (310) prior to proceeding as described above, with operation 510 or operation 512, depending upon whether a payer has been identified (508).

Although described as a particular series of operations, in some embodiments, more or fewer steps may be included in the method 500. For example, rather than identifying payers (506), the payers may already have been identified and provided to the method 500 at operation 502. In another example, the liability coverage may be located (516) prior to determining if a liability payer is likely to be primary coverage (514). In further embodiments, certain steps of the method 500 may be performed in a different order or in parallel. Other modifications of the method 500 are possible.

Figure 6:
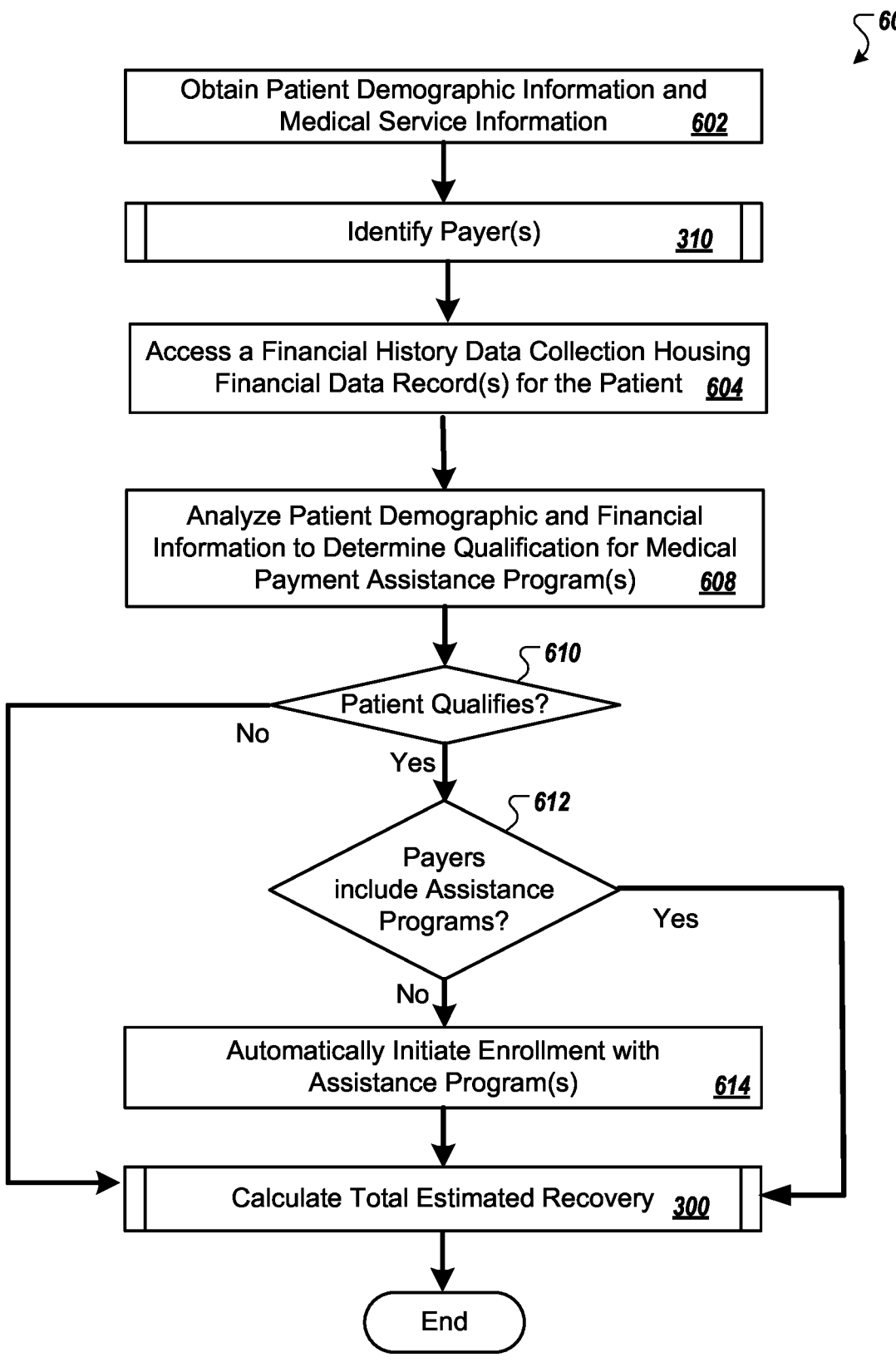
FIG. 6 is a flow chart of an example method for assisting an underinsured patient in identifying eligibility for assistance programs.

FIG. 6 is a flow chart of an example method 600 for assisting a patient in identifying eligibility for assistance programs. Portions of the method 600, for example, may be performed by the assistance availability analysis engine 238 of FIG. 2.

In some implementations, the method 600 begins with obtaining patient demographic information and medical service information (602). The patient demographic information and medical service information may be obtained and may include similar information, for example, as described in relation to the patient demographic data 116 and the procedure codes 114 of FIG. 1A. In another example, the patient demographic information and medical service information may be received as part of a medical claim as described in relation to operation 152 of the method 150 of FIG. 1B. In an implementation, the patient demographic information may include patient income information and/or a federal poverty level (FPL) qualification for the patient.

In some implementations, payers providing active coverage to the patient are identified (310). The payers may be identified, for example, using the method 310 of FIG. 3B. In some instances, the method 300 may return a result that there are no payers providing active coverage to the patient.

In some implementations, a financial history data collection housing financial data record(s) for the patient is accessed (604). Operation 604 is substantially as described above with regard to the operation 164 of the method 150 in FIG. 1B. The financial history data collection may indicate and/or include the FPL qualification of the patient. In an implementation, the operation 604 is optional. For example, operation 604 may not be implemented if the FPL qualification is included in the patient demographic information at operation 602.

In some implementations, patient demographic information is analyzed to determine qualification for one or more medical payment assistance programs (608). For example, the demographic information may be analyzed as described in relation to the assistance availability analysis engine 238 of FIG. 2. The analysis may return an indication of qualified/unqualified. In another example, the analysis may return a confidence level or confidence rating in the analysis (e.g., highly likely to qualify, 80% confident the patient qualifies, etc.). Operation 608 may further include analysis of the financial information to determine the qualification for medical payment assistance programs. For example, based on an FPL, the patient may qualify for a federal assistance program like Medicaid and/or other FPL based funding sources or programs.

In some implementations, if the patient is determined to qualify (or likely qualify) (610), the method 600 verifies that the payer(s) identified by the method 310 of FIG. 3B do not already include medical payment assistance programs for which the patient is qualified. For example, the method 600 may verify that the payer(s) identified by the method 310 do not include Medicaid.

If the patient is determined to qualify (or likely qualify) (610) and the payers do not include the assistance programs (612), then enrollment with the medical payment assistance program(s) is automatically initiated (614). For example, the automatic enrollment may be performed as described in relation to the assistance availability analysis engine 238 of FIG. 2.

If the patient does not qualify for medical payment assistance program(s) (e.g., at operation 610) or if the payer(s) identified by the method 310 include the medical payment assistance program(s) (e.g., at operation 612), then the method 600, in some implementations, moves to the method 300 to calculate a total estimated recovery based on estimates of a likelihood to pay for the payer and patient, as described above with regard to FIG. 3A.

Although described as a particular series of operations, in some embodiments, more or fewer steps may be included in the method 600. For example, identifying coverage for the patient may include evaluating the available coverage for sufficiency (e.g., applicable to the service(s), commonly used to cover the service(s) such as primary insurance rather than automobile insurance, etc.). In another example, the method 600 may terminate after initiating enrollment for medical payment assistance program (614), without calculating a total estimated recovery. In further embodiments, certain steps of the method 600 may be performed in a different order or in parallel. Other modifications of the method 600 are possible.

Figure 7:
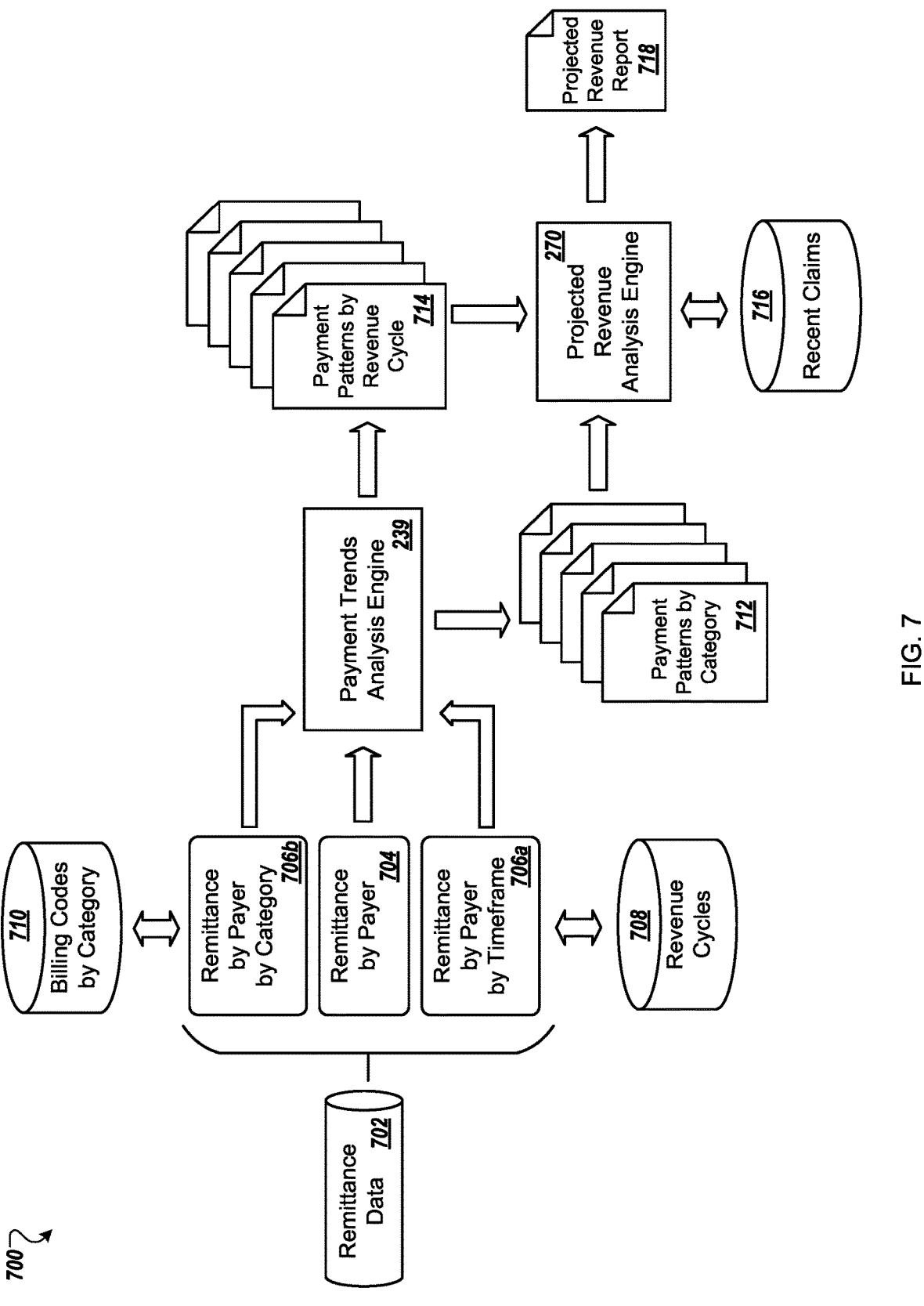
FIG. 7 is a flow diagram of an example process for estimating projected revenue for a medical services provider through performing machine learning analysis of recent claims data in view of historic remittance trends.

FIG. 7 is a flow diagram of an example process 700 for estimating projected revenue for a medical services provider through performing machine learning analysis of recent claims data in view of historic remittance trends. The analysis may provide the service providers with an idea of reimbursement amounts and timing of receipt of remittance from various payers based on the historic trends, allowing the service provider to forecast income in a much more precise manner than ever before. Therefore, service providers, through interfacing with the output of the process 700, may obtain increased confidence in budgets and future plans. At least a portion of the process 700 may be performed by the predictive analytics platform 102 of FIG. 2.

In some implementations, the process 700 begins by obtaining remittance data 702 and filtering or otherwise organizing the remittance data 702 into subsets, such as remittance by payer 704, remittance by payer by timeframe 706a, and remittance by payer by billing category 706b. The remittance by timeframe subset 706a, for example, may be divided based upon revenue cycles 708 (e.g., fiscal quarters). The remittance by payer category 706b may be divided by categories of billing codes 710. Billing code categories, in an illustrative example, may be determined by reviewing a leading portion of the code, since, at least in some coding schemes, the first portion of digits (or alpha-numeric code) may represent a category of similar products or services.

In some implementations, the payment trends analysis engine 239 of FIG. 2 analyzes the remittance data 704, 706a, and 706b to accumulate sets of payment patterns 712, 714 representing typical cycles of remittance according to various payers. Examples of various machine learning analysis and/or statistical clustering analysis that may be performed by the payment trends analysis engine 239 are discussed in relation to FIG. 2. The payment patterns, as illustrated, include the payment patterns by billing category data set 712 representing remittance levels (e.g., percentage paid) from each payer according to billing category (e.g., type or sub-type of service and/or product). The payment patterns also include the payment patterns by revenue cycle data set 714 representing a length of time between claim submission and receipt of reimbursement from each payer. Other patterns are possible, such as patterns of remittance by payer plan or patterns of remittance by patients.

In some implementations, the projected revenue analysis engine 270 applies the patterns 712, 714 to recent claims 716 as described in relation to FIG. 2. The recent claims 716, for example, may be claims pending submission and/or claims submitted but not yet reimbursed. The projected revenue analysis engine 270 may prepare a projected revenue report 718 (e.g., estimated reimbursement levels and estimated timing of remittance) for review by a representative of the service provider. In other embodiments, the projected revenue analysis engine 270 provides a set of forecast metrics to the report generation engine 278 of FIG. 2 for generating the report 718.

Figure 8:
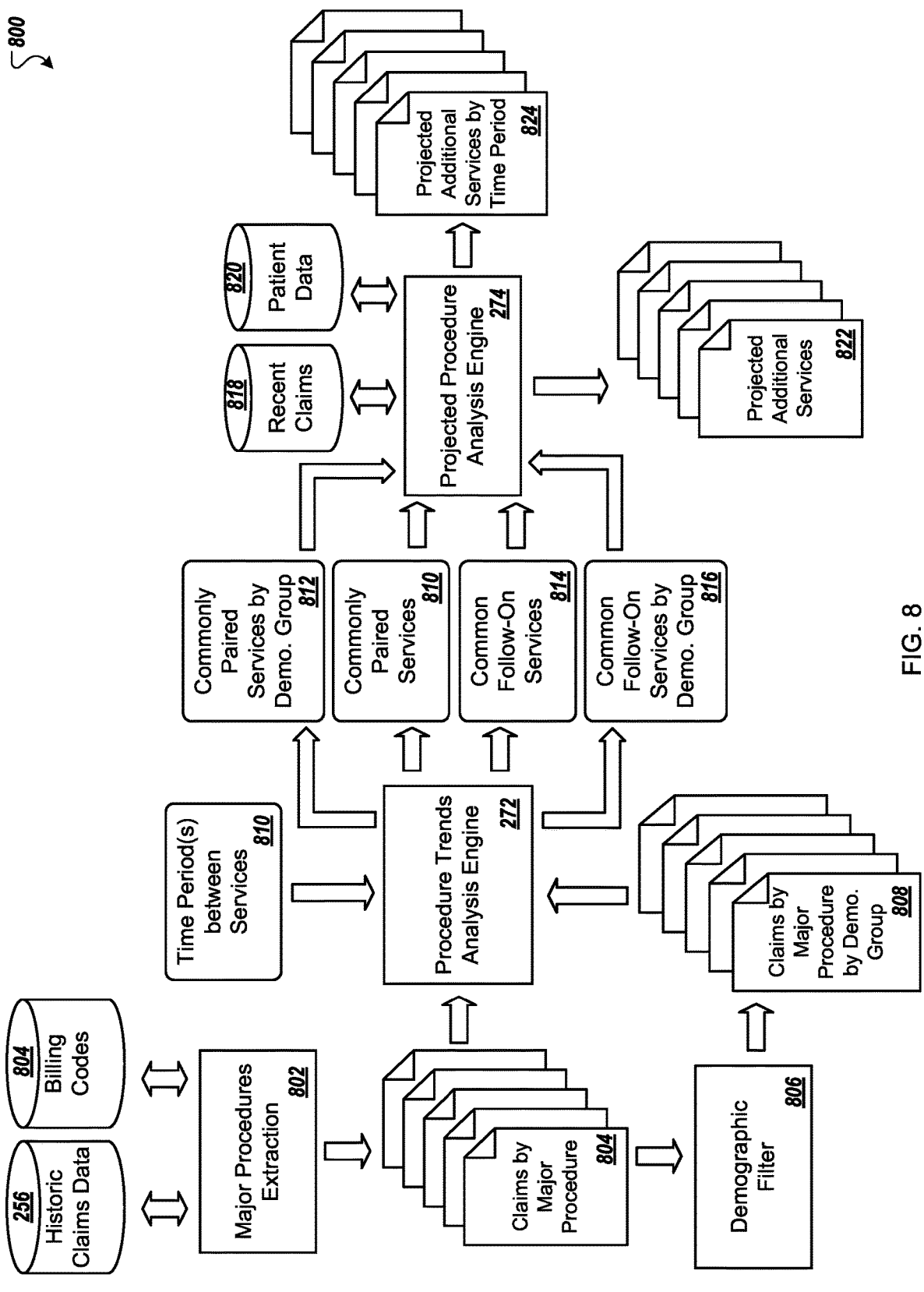
FIG. 8 is a flow diagram of an example process for predicting future revenue through performing machine learning analysis of historic medical procedures to identify and extrapolate commonly paired and/or follow-on procedures to procedures captured in recent claims data.

FIG. 8 is a flow diagram of an example process 800 for predicting future services through performing machine learning analysis of historic medical procedures to identify and extrapolate commonly paired and/or follow-on services to procedures captured in recent claims data and/or upcoming service requests (e.g., scheduled surgeries, etc.). The projected additional services, for example, may be analyzed to project future revenue and/or to better anticipate upcoming demands for supplies, medical equipment, and/or personnel. At least a portion of the process 800 may be performed by the predictive analytics platform 102 of FIG. 2. For example, as illustrated, portions of the process 800 may be performed by the procedure trends analysis engine 272 and the projected procedure analysis engine 274, described in relation to FIG. 2.

In some implementations, the process 800 begins with extracting claims including major procedures from the historic claims data 256. Billing codes 804 representing major procedures, for example, may be provided to a major procedures extraction engine 802 to filter the historic claims data 256 to sets of claims by major procedure 804.

In some implementations, the claims are further arranged in sets of each major procedure by one or more demographic groups. For example, a demographic filtering engine 806 may sort the sets of claims by major procedure 804 into subsets of claims by age group and/or gender.

In some implementations, the procedure trends analysis engine 272 receives the sets of claims by major procedure 804 and the subsets of claims by major procedure by demographic group 808 and analyzes the claims 804, 808 to identify commonly paired services 810 and commonly paired services by demographic group 812. Further, the procedure trends analysis engine 272 may receive additional historic claims data 256 related to the patients selected within one or more time periods 810 between the major procedure(s) and the service(s) to identify common follow-on services 814 and common follow-on services by demographic group 816. The procedure trends analysis engine 272, for example, analyzes the claims as described in relation to FIG. 2.

In some implementations, the commonly paired services 810, commonly paired services by demographic group 812, common follow-on services 814, and common follow-on services by demographic group 816 are provided to a projected analysis engine 274 for further analysis in view of recently submitted claims 818 (or service requests 260 of FIG. 2 representing upcoming services). The projected analysis engine 274 may analyze the recent claims 818 and/or the service requests 260 to identify projected additional services 822 and projected additional services 824 by time period, as described in relation to FIG. 2.

Figure 10A:
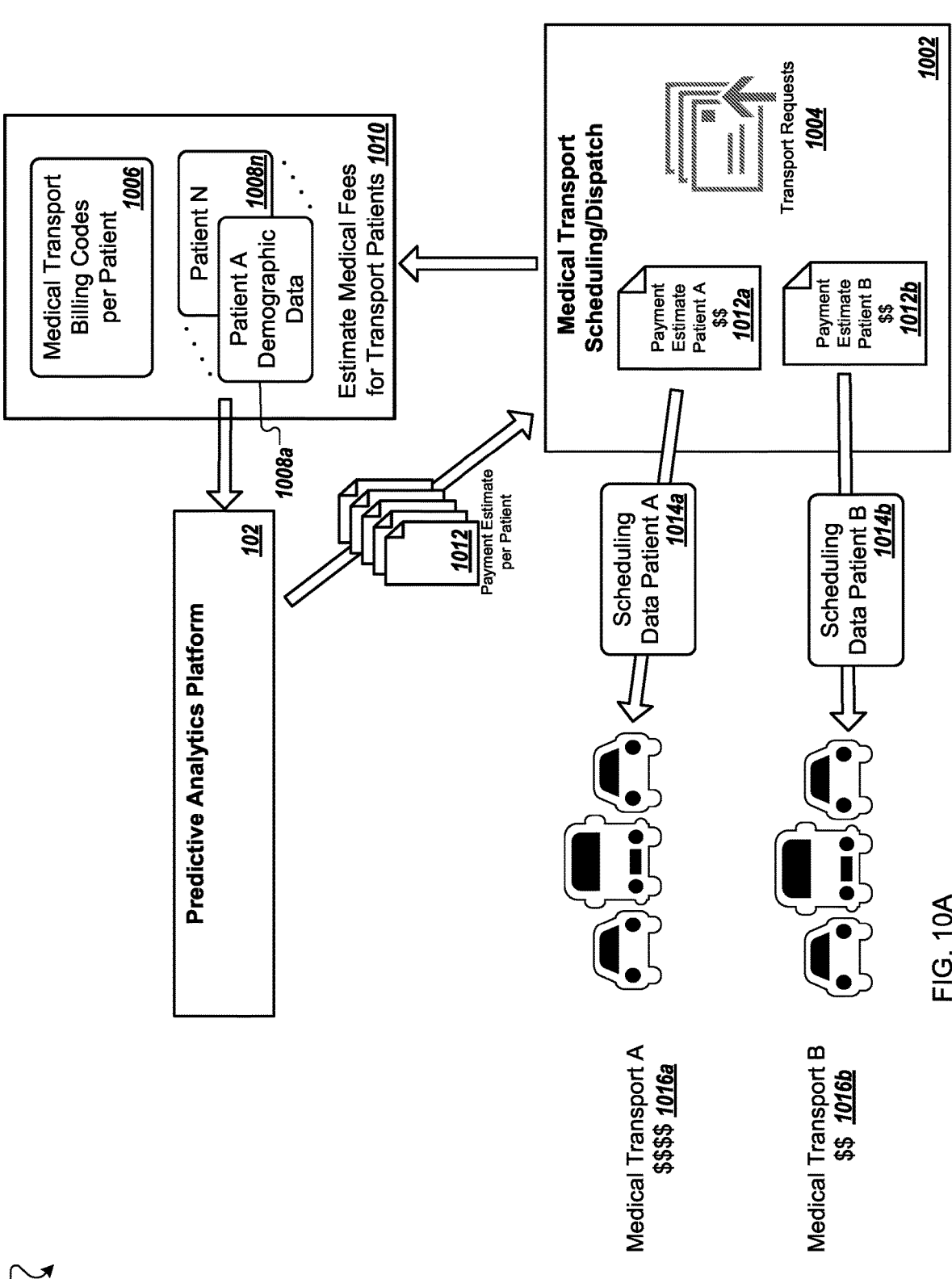
FIG. 10A is a flow diagram of an example process for intelligently scheduling and/or dispatching medical transport through performing machine learning analysis of historic medical transport records in view of patient demographics.

FIG. 10A is a flow diagram of an example process 1000 for intelligently scheduling and/or dispatching medical transport through performing real-time or near-real-time machine learning analysis of historic medical transport records in light of patient demographics. At least a portion of the process 1000 may be performed by the predictive analytics platform 102 of FIG. 2.

In some implementations, a medical transport scheduling and dispatch platform 1002 receives transport requests 1004 for transporting patients to medical facilities (e.g., emergency medical transport, doctor visit transport, hospital to hospice or nursing facility patient transfer, medical facility to specialist facility transfer, etc.). Each transport request 1004 may include a pick-up location, a drop-off location, a time of transfer, and/or patient demographic data such as name, date of birth, address, gender, phone number, and/or social security number. A portion of the transport requests 1004 may identify special requirements for the patient, such as wheelchair transfer. Further, at least a portion of the transport requests 1004 may include payer information regarding a payer providing coverage for the service. In some examples, the transport requests 1004 may be submitted by emergency medical services (e.g., automatically through a patient charting record or through a separate submission function available through the medical transport scheduling and dispatch platform 1002), service providers, and/or emergency dispatch systems (e.g., 911). The medical transport scheduling and dispatch platform 1002 is configured to receive incoming requests and schedule/dispatch medical transport from medical transport providers such as a first medical transport provider 1016a and a second medical transport provider 1016b.

In some implementations, the medical transport scheduling and dispatch platform 1002 coordinates with the predictive analytics platform 102 to intelligently distribute the transport requests 1004 between the medical transport providers 1016 based on patient demographic data 1008 and transport billing codes 1006 corresponding to each patient (e.g., type of transport service required). The medical transport scheduling and dispatch platform 1002, for example, submits one or more requests 1010 to the predictive analytics platform 102 for estimated medical fees for transporting each of the patients. The requests 1010 may be submitted in real-time, in near-real-time, and/or in batch mode. For example, the medical transport scheduling and dispatch platform 1002 may automatically submit requests for payment estimates related to emergency medical transport, while requests for pre-scheduling of medical check-up visits, dialysis, or chemotherapy sessions may be uploaded in batch mode. The medical transport scheduling and dispatch platform 1002, for example, may communicate with the predictive analytics platform 102 via an application programming interface (API) or other electronic transfer mechanism. In another example, a widget or applet installed in the computing system of the medical transport scheduling and dispatch platform 1002 may integrate information from the medical transport scheduling and dispatch platform 1002 while maintaining the security and confidentiality of data entered into and stored by the medical transport scheduling and dispatch platform 1002. Each request may include demographic data 1008 for at least one patient along with at least one medical transport billing code 1006. For example, a request for transport may also include a request for services provided in transit, such as oxygen delivery, which can be factored into the payment estimate.

In some implementations, the predictive analytics platform 102 analyzes the patient demographic data to identify or confirm payer coverage. For example, the predictive analytics platform 102 may provide the patient demographic data 1008 to the payer identification engine 218 or the coverage verification engine 216 (if the patient information provided included a payer identification) of FIG. 2 to identify and/or confirm payer coverage. Further, the predictive analytics platform 102 may provide the billing code(s) corresponding to each patient 1008 to the payment pattern application engine 226 of FIG. 2 to estimate a remittance value associated with each transport request 1004.

In some implementations where little patient demographic information is known (e.g., an emergency medical event with an unconscious or incoherent patient), the predictive analytics platform 102 analyzes the provided demographic data, for example using the demographic verification engine 214, to obtain greater information regarding the patient. For example, if the pick-up address is at a domicile, the address may be applied to the patient name to determine if the address is the patient's home.

In some implementations, the predictive analytics platform 102 provides the payment estimates per patient 1012 to the medical transport scheduling and dispatch platform 1002. Using the payment estimates 1012, the medical transport scheduling and dispatch platform 1002 distributes the transport requests 1004 to the medical transport companies 1016 in accordance with a price level associated with each medical transport company 1016a, 1016b. For example, as illustrated the medical transport company 1016a is more expensive than the medical transport company 1016b, so by scheduling in accordance with reimbursement the medical transport scheduling and dispatch platform most efficiently distributes the transport requests 1004 to ensure the medical transport companies 1016a, 1016b are most likely to be fully reimbursed for the services. In one example, where the medical transport scheduling and dispatch platform 1002 owns or is associated with a particular medical transport company 1016, the transport provider increases revenue by increasing confidence in reimbursement for the services provided for their transport services.

Although described in relation to payment levels, in some implementations, if there are options on where to transport a patient, the predictive analytics platform 102 may promote an in-network hospital or other covered facility in favor of a generally equidistant hospital that is not within the patient's insurance coverage. Other additions to or modifications to the process flow 1000 are possible.

FIG. 1013 is a flow diagram of an example process 1020 for validating a prescription in real-time or near real-time through performing machine learning analysis on prescription billing codes in view of patient demographics. As illustrated, prescription requests 1024 are received by a prescription services platform 1022. The prescriptions, for example, may be for a recommended product and/or service for a patient. A medical practitioner such as a doctor or surgeon, for example, may recommend a variety of therapy services, diagnostic products and/or services, and/or other recovery assistance prescriptions for a patient. The medical practitioner may need to identify insurance coverage for different options and/or discern a justification coding for the product(s) and/or service(s) accepted by the patient's insurance provider.

To accelerate the diagnostic or recovery process, in some implementations, the prescription services platform 1022, upon receiving prescription requests 1024 (e.g., suggested prescriptions for the patient made by the medical practitioner), submits a fees estimate 1026 including one or more prescription billing codes 1028 along with patient demographic data 1030 to the predictive analytics platform 102 to request an estimate of medical fees for the patient associated with the recommended products and/or services.

In some implementations, the payment pattern application engine 226 and/or the payer pre-approval analysis engine 232 of the predictive analytics platform 102 (e.g., described in relation to FIG. 2) analyze the billing codes 1028 in view of the patient information to determine likelihood of coverage for the prescriptions and whether pre-approval appears to be required by the payer. The payer identification engine 218, in some embodiments, is invoked to identify one or more payers providing active coverage for the patient. In other embodiments, the prescription services platform 1022 provides payer information, and the predictive analytics platform 102 may confirm coverage by invoking the coverage verification engine 216 of FIG. 2. Further, the payment pattern application engine 226 may determine an estimated recovery for the prescription products and/or services, for example as described in relation to the method 320 of FIG. 3C.

The predictive analytics platform 102, in some implementations, includes a prescription approval analysis engine 1034 configured to analyze the claims data 256 in light of approvals and/or denials by the patient's payer(s) for the prescription products and/or services identify proposed reasons and/or justifications for the products and/or services being subscribed to supply suggested language that may apply to the present patient. For example, denials associated with the claims data 256 may indicate reasons including lack of justification and/or insufficient justification. The prescription approval analysis engine 1034, on some embodiments, limits analysis to more recent data such as, in some examples, approvals and/or denials within the same calendar year, approvals and/or denials within the last six months, or approvals and/or denials within the last twelve months.

In some implementations, the predictive analytics platform 102 returns analysis results 1032 including, in some examples, payer and payment verification, payment estimate information, and/or suggested justification language to the prescription services platform 1022 for use in determining the most appropriate products and/or services for the patient (e.g., the covered product(s) in view of two or more options) and in applying for reimbursement from the patient's payer.

A wearable cardio-defibrillator, such as for example the ZOLL LifeVest® wearable cardioverter defibrillator, provides one example of a real-time prescription implementation. A cardiologist prescribes a wearable cardio-defibrillator for a patient at high risk for sudden cardiac arrest. The wearable cardio-defibrillator is an externally worn vest that monitors a patient's heart rhythm continuously and, if the heart rhythm indicates a life-threatening arrhythmia, the wearable cardio-defibrillator provides a shock treatment to restore a normal heart rhythm. Such a device is prescribed, for example, when a patient is waiting for surgery for an implantable defibrillator (ICD) pending monitoring of ventricular function for natural improvements or resolution of an infection or for example as a supplement to pharmacological cardiac treatments designed to avoid surgery. Thus, due to the critical nature of this wearable device to the patient's ability to stay alive, the prescription needs to be written and filled in as short a time as possible. There is generally a complex justification required for such a prescription and the patient and provider benefit from a real-time knowledge of predicted coverage amounts, accurate pre-payment amounts, and optimized claim submission. For example, if a patient has multiple coverages or a single insufficient coverage plan, the predictive analytics platform 102 can identify the payers associated with the predicted coverage amounts along with enabling discovery of other payers. Furthermore, communicative coupling between the predictive analytics platform 102 and the various payers and providers may enable an automated, accurate, and efficient process in real-time for the prescription and delivery of the necessary medical device.

Figure 10B:
FIG. 10B is a flow diagram of an example process for validating a prescription in real-time or near real-time through performing machine learning analysis on prescription billing codes hi view of patient demographics.
Figure 10C:
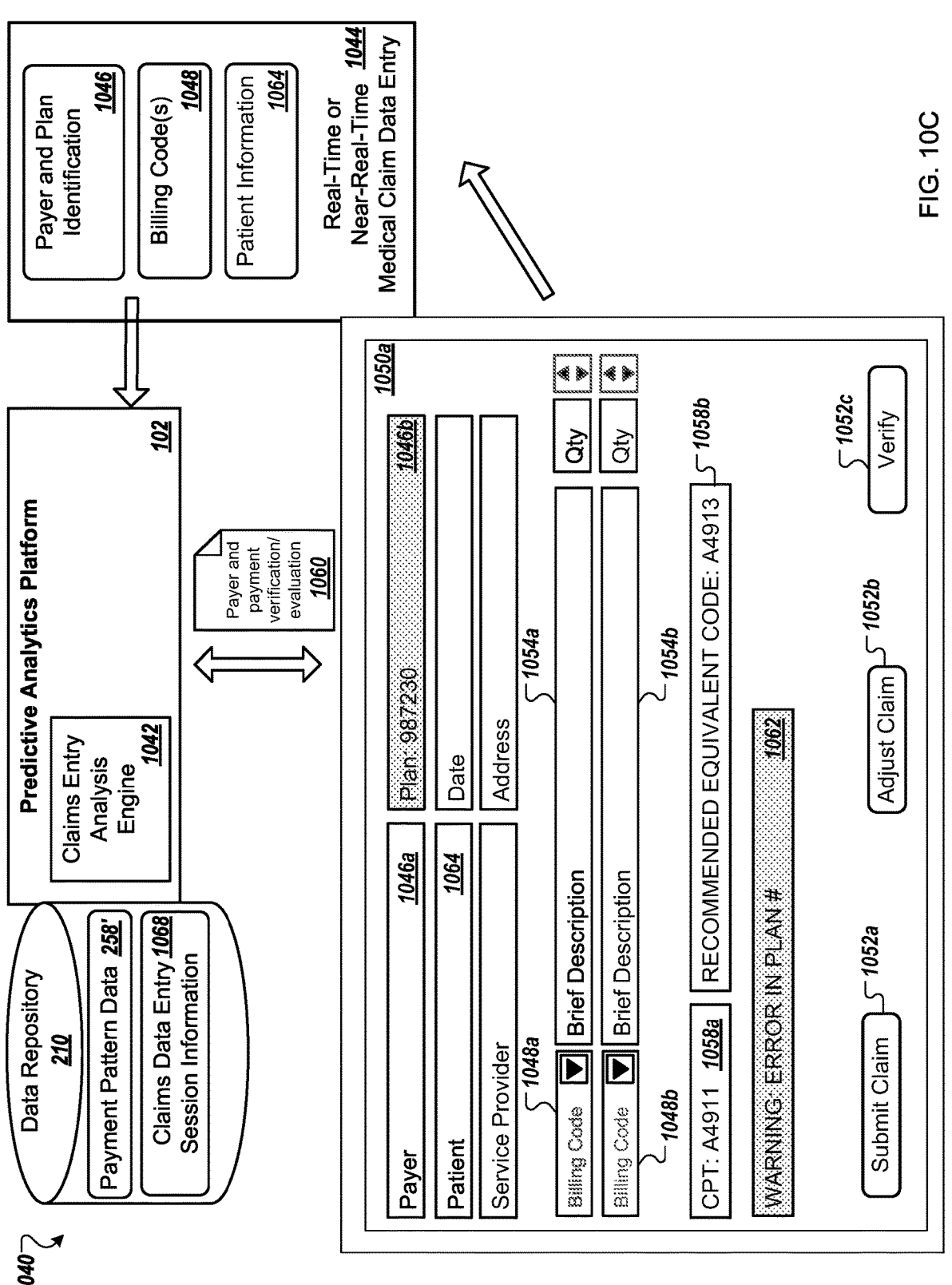
FIG. 10C is a flow diagram of an example process for providing real-time feedback related to medical claim population.

Turning to FIG. 10C, a flow diagram is illustrated of an example process 1040 for providing real-time feedback related to medical claim population to ensure accurate and complete information is entered by a representative of the medical provider at a graphical user interface (GUI) 1050a. At least a portion of the process 1040 may be performed by the predictive analytics platform 102 of FIG. 2. As illustrated, the predictive analytics platform 102 includes a claims entry analysis engine 1042 for performing real-time analysis of real-time or near-real-time medical claim data entry information 1044 to the medical claim represented in the GUI 1050a. The medical claim data entry information 1044, for example, may include line-item additions and/or adjustments to fields of the medical claim being entered at the GUI 1050a, such as payer and plan identification 1046 as well as billing code(s) 1048.

In some implementations, prior to submitting a medical claim (e.g., using a submit control 1052a), the medical claim data entry information 1044 is provided to the predictive analytics platform 102 for review by the claims entry analysis engine 1042. The medical claim data entry information 1044, for example, may be issued to the predictive analytics platform 102 when the representative selects a verify control 1052c of the GUI 1050a. The medical claim data entry information 1044 may be provided to the predictive analytics platform 102, in some examples, via an API and/or via a widget or applet executing on the system including the claims entry software that generates the GUI 1050a.

In some implementations, the predictive analytics platform 102 stores at least a portion of the claims data entry session information 1068. For example, the predictive analytics platform 102 may store the payer and plan identification 1046 so that it is only provided once in the medical claim data entry information 1044. For example, while analyzing real-time data entry (e.g., not waiting until the verify control 1052*c* is activated), the predictive analytics platform 102 may repeatedly receive line-item updates of data entered into the GUI 1050*a*.

The predictive analytics platform 102, in some implementations, analyzes the payer and plan identification 1046 for accuracy. For example, the coverage verification engine 216, described in relation to FIG. 2, may confirm that the payer 1046*a* and plan identifier 1046*b* (illustrated in GUI 1050*a*) represent active coverage information for a patient identified by patient information 1064. The patient information 1064, for example, may include some portion of a full name, an address, a date of birth, social security information, and/or gender. The coverage verification engine 216 of the predictive analytics platform 102, as described in relation to FIG. 2, may analyze the payer information 1046 and the patient information 1064 to verify coverage. If the coverage cannot be verified (e.g., outdated information, mis-typed plan identifier, more information required such as a responsible party, etc.), in some embodiments, the predictive analytics platform 102 provides the claims entry application (e.g., the application causing presentation of the GUI 1050*a*) with payer verification and/or evaluation information 1060. For example, the GUI 1050*a*, as illustrated, is updated with a warning message 1062 indicating that there appears to be an error in the plan number. Further, the text entry field containing the plan identifier 1046*b* is highlighted or shaded to indicate to the user that there is a problem with that field.

In some implementations, the predictive analytics platform 102 analyzes the billing codes 1048*a*, 1048*b*, alone or in combination, to determine a likelihood of payment by the payer 1046*a* under the plan 1046*b*. Some payers may only accept a subset of the billing codes or otherwise lean toward preferred billing codes for requesting reimbursement. In this manner, for example, the payers may desire a broader code be used rather than a code corresponding to a more detailed description (e.g., no matter whether a minibus or a larger bus is used for a patient transport, the payer may desire coding using the code corresponding to minibus). Oftentimes, service providers must struggle through large manuals to discover such details and will instead likely overlook these requirements, leading to denial of the claim, a need for re-submission, and a delay in reimbursement. In some embodiments, the claims entry analysis engine 1042 may analyze the billing codes 1048 in view of payment pattern data 258' (e.g., payment pattern data 258 as described in relation to FIG. 2 plus, in some embodiments, other data sources) to determine whether the payer has historically reimbursed for the entered code(s). If not, the claims entry analysis engine 1042 may determine a recommended equivalent code for requesting reimbursement. For example, as illustrated in the GUI 1050*a*, a CPT code 1058*a* of A4911 has been entered by the representative, but the predictive analytics platform 102, in the payer and payment verification/evaluation information 1060, has identified that an equivalent code of A4913 1058*b* is recommended.

The GUI 1050*a* includes an adjust claim control 1052*b*. In some implementations, upon selection of the adjust claim control 1052*b*, the predictive analytics platform 102 causes recommended changes to be applied to the claim presented in the GUI 1050*a*. For example, the predictive analytics platform 102 may identify an appropriate plan number 1046*b* by executing the payer identification engine 218 and/or the demographic verification engine 214 to match the patient information 1064 to an appropriate payer plan. The match, for example, may be within a degree of confidence, such as at least 80% confidence or an otherwise high confidence level. Further, the recommended equivalent code 1058*b* may be transferred to the appropriate billing code entry box 1048.

In some implementations, the claim entry analysis engine 1042 analyzes pairs or groupings of billing codes 1048 (e.g., with or without limitation to the payer 1046*a*) to determine whether claims have been reimbursed with the same combination of billing codes 1048*a* and 1048*b* and/or whether the billing codes otherwise make sense being used in coordination. For example, if the representative mistakenly entered both A0998 (ambulance response and treatment, no transport) and A0427 (ambulance service, advanced life support, emergency transport), the claims entry analysis engine 1042 may flag the combination as an error. In other embodiments, the claims entry analysis engine 1042 may analyze the payment pattern data 258', including code combination analysis, to identify that the combination has not or has rarely been used. Further, the claims entry analysis engine 1042 may identify a recommended equivalent code for replacing a pair of billing codes which captures the services identified in the two separate billing codes.

In some implementations, after the representative has completed data entry for the medical claim and the predictive analytics platform 102 has verified the information, the representative may select a submit claim control 1052*a* to submit the claim to the payer for reimbursement.

Figure 10D:
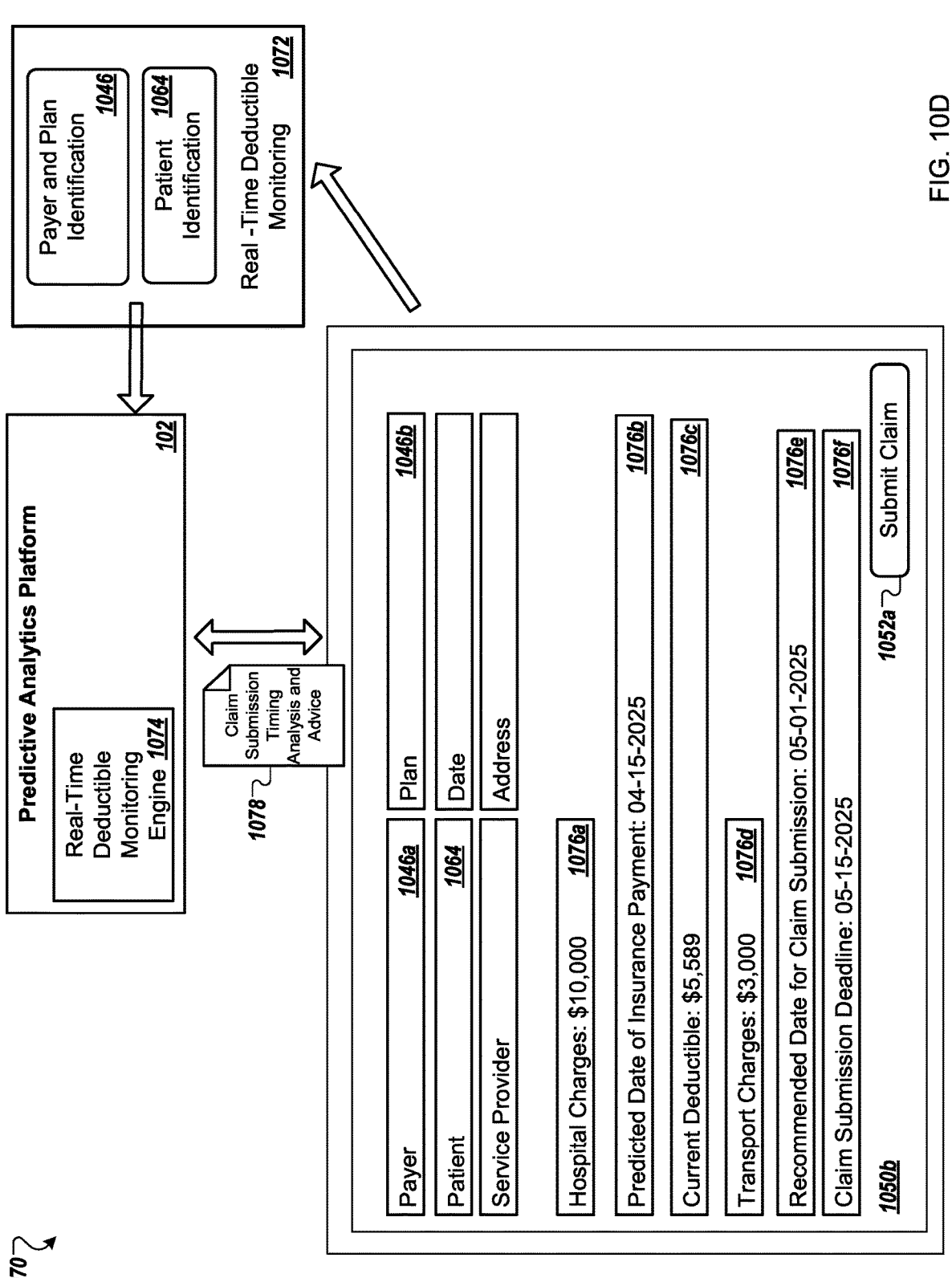
FIG. 10D is a flow diagram of an example process for performing real-time deductible monitoring related to a transport service claim.

Turning to FIG. 10D, a flow diagram is presented of an example process 1070 for performing real-time deductible monitoring related to a transport service claim. Oftentimes, when a patient is picked up by emergency transport services, two or more payers will be implicated in the service. This can include, in some examples, both a patient deductible and a primary coverage, both liability coverage and primary coverage, and/or both primary coverage and secondary coverage. Because hospital services recovery is typically a much larger amount, rather than pursuing two or more different avenues for coverage, it may be more efficient for the emergency transport services provider to delay submission of the claim until the hospital has exhausted one or more of the available sources, such as the patient deductible.

As illustrated in an example screen shot of a graphical user interface 1050*b*, the payer 1046*a*, plan 1046*b*, and patient 1064 information is presented in a top portion of the screen. In a lower portion, claims status information 1076 is presented to identify pending reimbursements as well as information useful in coordinating claim submission between the transport provider and other medical provider(s) (as illustrated, a hospital service provider). The claims status information 1076 includes hospital charges 1076*a*, a predicted date of insurance payment 1076*b* to the hospital to reimburse the charges 1076*a* claimed, a current patient deductible 1076*c* under the plan 1046*b*, transport charges 1076*d*, a recommended date for claim submission 1076*e*, and a claim submission deadline 1076*f*. The claims status information 1076, for example, may be presented in a lower portion of the screen shot of the GUI 1050*a* presented in FIG. 10C after the claim has been filled in and verified. At least a portion of the claims status information 1076 may have been provided in the payer and payment verification/evaluation information 1060 of FIG. 10C. For example, based on the payment pattern data 258, the predictive analytics platform 102 may have determined the current deductible 1076*c* and/or the transport charges 1076*d*.

In some implementations, the claims application presenting the GUI 1050*b* provides a real-time deductible monitoring request 1072 to the predictive analytics platform 102. As illustrated, the request 1072 includes payer and plan identification information 1046 and patient identification information 1064.

In some implementations, the predictive analytics platform 102 includes a real-time deductible monitoring engine 1074 to determine whether the patient has already reimbursed the deductible amount or is likely to reimburse up to the full deductible amount in one or more additional pending medical claims (e.g., claims related to the transport charges 1076*d*). The real-time deductible monitoring engine 1074, for example, may identify the hospital charges 1076*a* (e.g., in the claims data 256 of FIG. 2) as well as a status of the hospital-related claim (e.g., date submitted), identify the present level of the patient's remaining deductible 1076*c* (e.g., using the coverage verification engine 216 of FIG. 2), and identify a likely timing of reimbursement to the hospital by the payer as the predicted date of insurance payment 1076*b* (e.g., using the payment trends analysis engine 239 of FIG. 2). As illustrated, the hospital charges 1076*a* are $10,000 and the current deductible level 1076*c* is $5,589. Thus, all of the patient's deductible can be allocated to the hospital charges rather than inefficiently splitting the deductible between the hospital and the transport service provider. The real-time deductible monitoring engine 1074, using payer plan information 244, may further identify the claim submission deadline 1076*f* of May 15, 2025. Since it is predicted that the hospital will be reimbursed around Apr. 15, 2025, the real-time deductible monitoring engine 1074 may recommend that the transportation service provider delay in claim submission until May 1, 2025 (e.g., after the hospital has likely submitted reimbursement but prior to the claim submission deadline 1076*f*). The analysis and advice from the real-time deductible monitoring engine 1074 may be provided from the predictive analytics platform 102 to the GUI 1050*b* as claim submission timing analysis and advice 1078.

Using the information presented in the GUI 1050*b*, a representative of the transportation service provider may opt to delay submission rather than selecting the submit claim control 1052*a*. In some implementations, the predicted analytics platform 102 may monitor the deductible periodically (e.g., starting after the predicted date of Apr. 15, 2025) and issue a notification to the transportation service provider when the deductible level is $0 to ensure timely submission of the claim. The notification, for example, may be provided through a user portal and/or via a communication mechanism logged with the predictive analytics platform 102, such as an email address or phone number for text messaging. In some embodiments, the representative may revisit the GUI 1052 periodically to obtain updated deductible information 1076*c*.

Figure 10E:
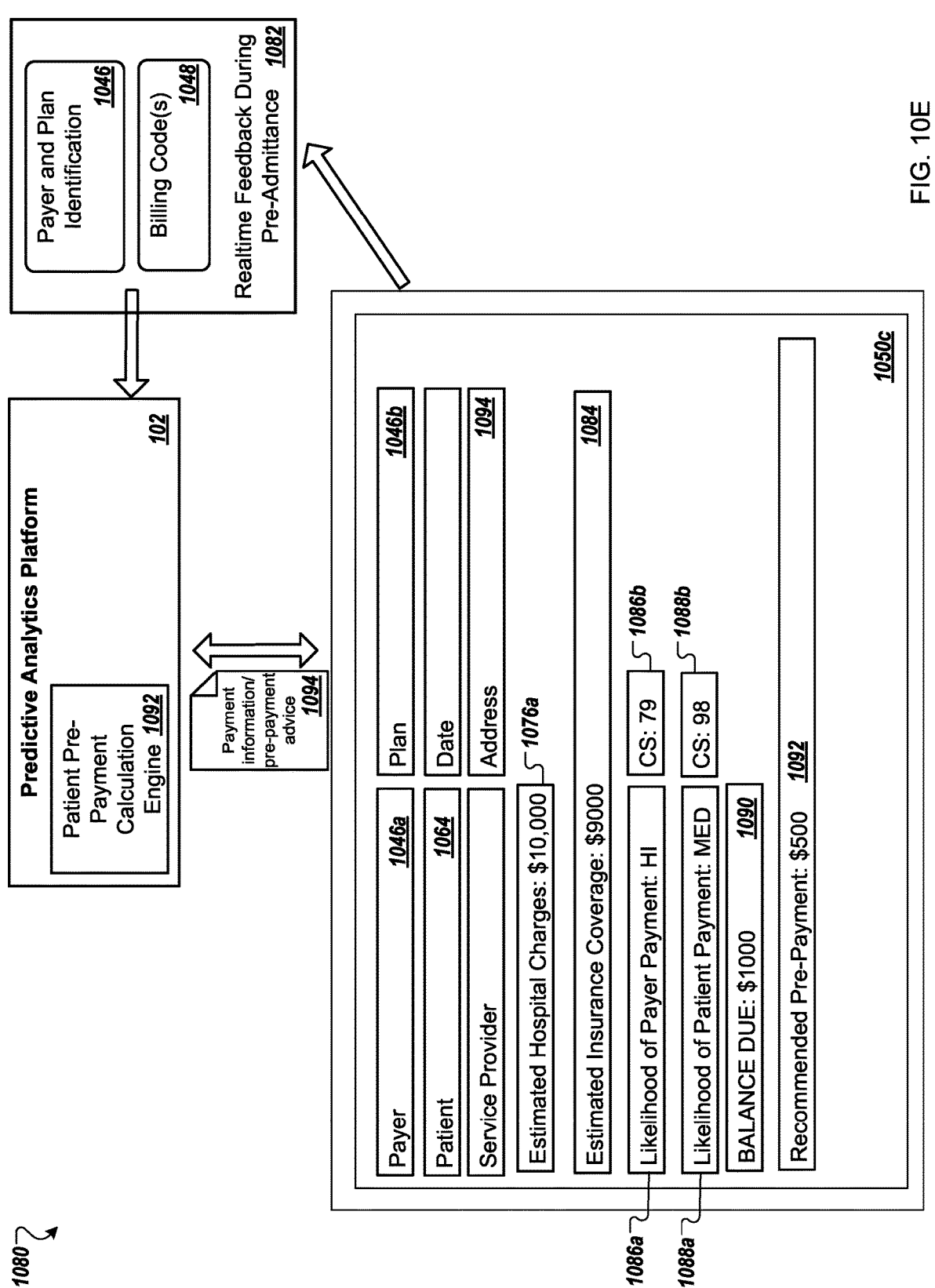
FIG. 10E is a flow diagram of an example process for real-time analysis of patient services during a visit to a medical provider to determine a pre-payment amount.

FIG. 10E is a flow diagram of an example process 1080 for real-time analysis of patient services during a visit to a medical provider to determine a pre-payment amount. An example screen shot of a graphical user interface (GUI) 1050*c* illustrates, again, the same initial information such as payer 1046*a*, plan 1046*b*, and patient 1064, as well as the estimated hospital charges 1076*a* of FIG. 10D. However, rather than the transport service provider discussed in relation to FIG. 10C, the GUI 1050*c* presents information for the hospital service provider, including estimated insurance coverage 1084 for the estimated hospital charges 1076*a*, a likelihood of payer payment 1086*a* of the estimated insurance coverage 1084*a* and corresponding confidence score

1086*b*, a likelihood of patient payment 1088*a*, a balance due 1090 representing a difference between the estimated hospital charges 1076*a* and the estimated insurance coverage 1084, a likelihood of patient payment 1088*a* and corresponding confidence score 1088*b*, and a recommended pre-payment amount 1092. The estimated charges 1076*a*, insurance coverage 1084, likelihood of payer patient 1086, likelihood of patient payment 1088, and balance due 1090, for example, may be determined using at least portions of the method 300 of FIG. 3A and its sub-methods, In some implementations, the predictive analytics platform 102 includes a patient pre-payment calculation engine 1092 to determine the recommended pre-payment amount 1092 based on the balance due 1090 and the likelihood of patient payment 1088. For example, although the patient's likelihood to pay $1,000 is medium 1088*a* with a confidence score of 98/100 1088*b*, the patient may have a higher likelihood of covering a portion of the balance due 1090. Further, the likelihood of the patient repaying any portion of the balance due 1090 may drop significantly after leaving the facility (e.g., when being billed to a home address 1094). Thus, the patient pre-payment calculation engine 1092 may analyze remittance data 268 related to similar patients (e.g., identified by the patient matching engine 230) to identify an amount of funds up to the balance due 1090 that is associated with a high likelihood of payment. The patient pre-payment calculation engine 1092 may further identify the amount based on at least a threshold confidence score of the high likelihood that the patient will pay the amount. The patient pre-payment calculation engine 1092 may perform many of the same functions of the patient likelihood to pay analysis engine 228, but with a goal of a likelihood rating rather than a goal of a particular reimbursement amount. Further, in some embodiments, the patient pre-payment calculation engine 1092 identifies sources of immediate funds for pre-payment of services such as, in some examples, a patient health savings account, flexible spending account, and/or an available credit balance on a medical spending credit card. The pre-payment amount 1092 may reflect in part confidence in the availability of one or more of these sources to the patient.

As illustrated, the patient pre-payment calculation engine 1092 has determined a recommended pre-payment amount 1092 of $500, i.e., half of the balance due 1090.

The predictive analytics platform 102, in some embodiments, provides payment information/pre-payment advice 1092 to the application presenting the GUI 1050*c* for presentation. In reviewing the GUI 1050*c*, a representative of the hospital may elect to invoice the patient the recommended pre-payment amount 1092 or another amount (e.g., up to the balance due 1090).

Figure 11:
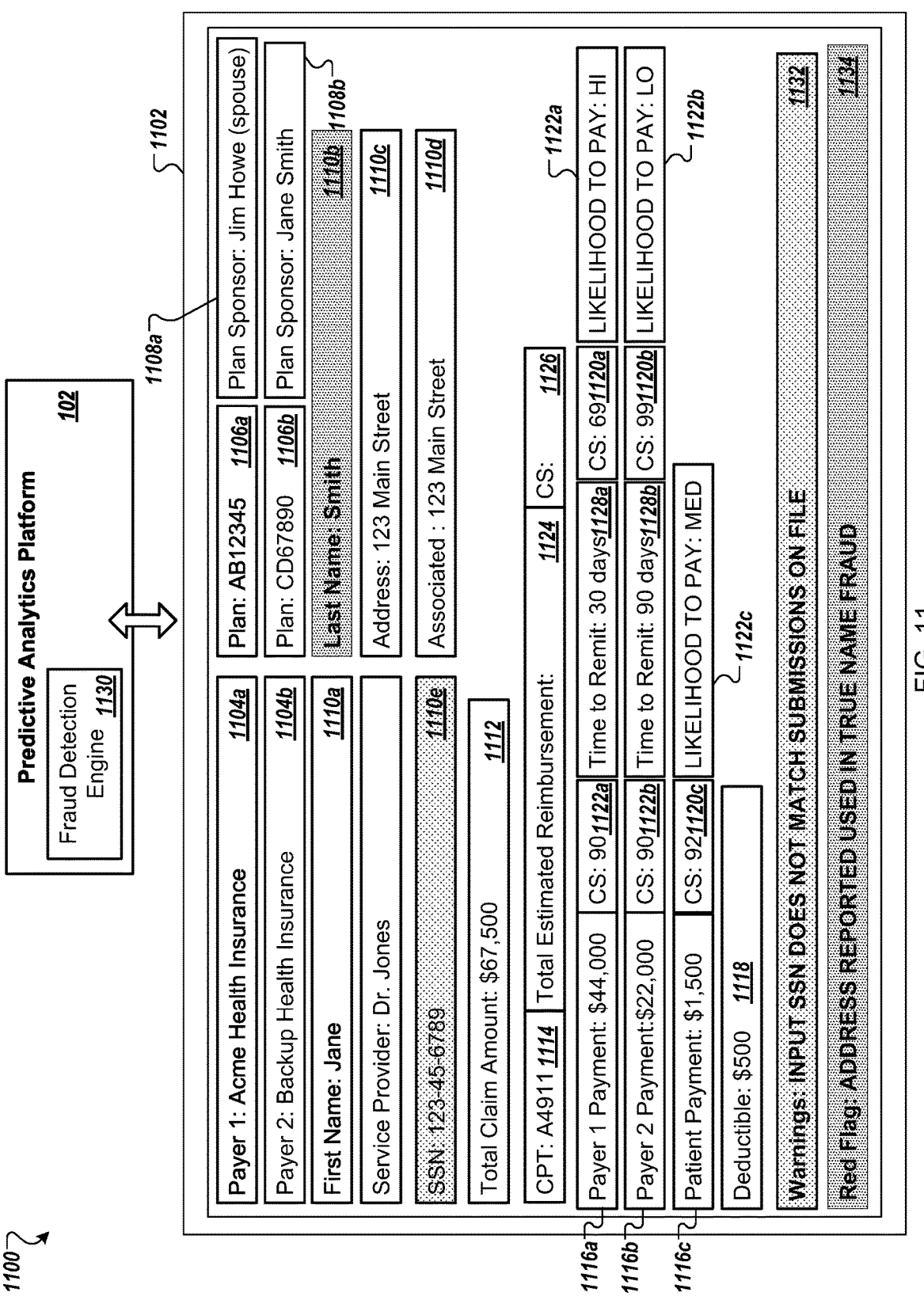
FIG. 11 is an example screen shot of a graphical user interface for presenting payment estimates related to a medical claim.

Turning to FIG. 11, an example system 1100 includes a graphical user interface (GUI) 1102 for presenting payment estimates related to a medical claim and the predictive analytics platform 102. In some embodiments, the predictive analytics platform 102 generates the GUI 1102, for example through a claims processing engine of the predictive analytics platform 102. In other embodiments, a claims processing application is configured to communicate with the predictive analytics platform 102, for example through one or more API calls, to obtain complex predictive intelligence from the predictive analytics platform 102, as described in relation to FIG. 1A. A portion of the information in the GUI 1100 may be provided by and/or analyzed by the predictive analytics platform 102 to enhance service provider confidence in obtaining reimbursements for services and/or products provided to a patient identified in patient information 1110*a*.

As illustrated, the GUI 1100 presents patient information 1104, including first name 1110*a*, last name 1110*b*, address 1110*c*, social security number (SSN) 1110*e*, and an address associated with the SSN 1110*d*. Two payers are presented as providing active coverage for the patient (Jane Smith). A first payer 1104*a* is associated with plan information 1106*a* and a plan sponsor 1108*a* identified as the spouse of Jane Smith. A second payer 1104*b* is associated with plan information 1106*b* and a plan sponsor 1108*b* identified as Jane Smith. A total claim amount 1112 ($67,500) related to billing code 1114 (A4911) is distributed between a first payer payment amount 1116*a* ($44,000), a second payer payment amount 1116*b* ($22,00), and a patient payment amount 1116*c* ($1,500). The patient payment amount 1116*c* captures a deductible amount 1118 ($500).

Each payment amount 1116 is associated with a payment confidence score 1120 related to a corresponding likelihood to pay 1122. The payer payment amounts 1116*a,b* are further associated with a coverage coordination confidence score 1122*a*, 1122*b* representing confidence in the division of the first payer payment amount 1116*a* and the second payer payment amount 1116*b*.

In some implementations, the GUI 1102 further includes a total estimated reimbursement 1124 and an associated reimbursement confidence score 1126 determined by combining the payments 1116 and associated confidence scores 1120. The total estimated reimbursement 1124, in some embodiments, may further reflect a second confidence score of the second payer covering more of the total reimbursement 1124 if the first payer 1104*a* fails to cover the entire first payer payment 1116*a*. For example, as illustrated, a time to remit a claim for reimbursement to the first payer 1128*a* is 30 days and a time to remit a claim for reimbursement to the second payer 1128*b* is 90 days, such that the first payment amount 1116*a* may be submitted to the first payer 1104*a* prior to submitting a claim for payment to the second payer 1104*b* (e.g., the backup health insurance). For example, the second payer 1104*b* may not accept the claim for processing prior to confirmation of the first payer 1104*a* reimbursing a first portion of the claim amount 1112.

In some implementations, the predictive analytics platform 102 reviews the patient information 1110*a* to identify one or more potential problems. For example, a fraud detection engine 1130 may review the patient information 1110*a* to identify information that is inconsistent with other data sources and/or potential security concerns regarding the patient, such as identity theft reports. As illustrated, for example, a warning 1132 states that the "input ssn does not match submissions on file." The warning, for example, may be highlighted in a same manner as the SSN field 1110*e* (e.g., in yellow). In another example, a security red flag 1134 states that the address has been reported as used in true name fraud. The last name field 1110*b* is highlighted in a same manner as the security red flag 1134 (e.g., red).

Figure 12A:
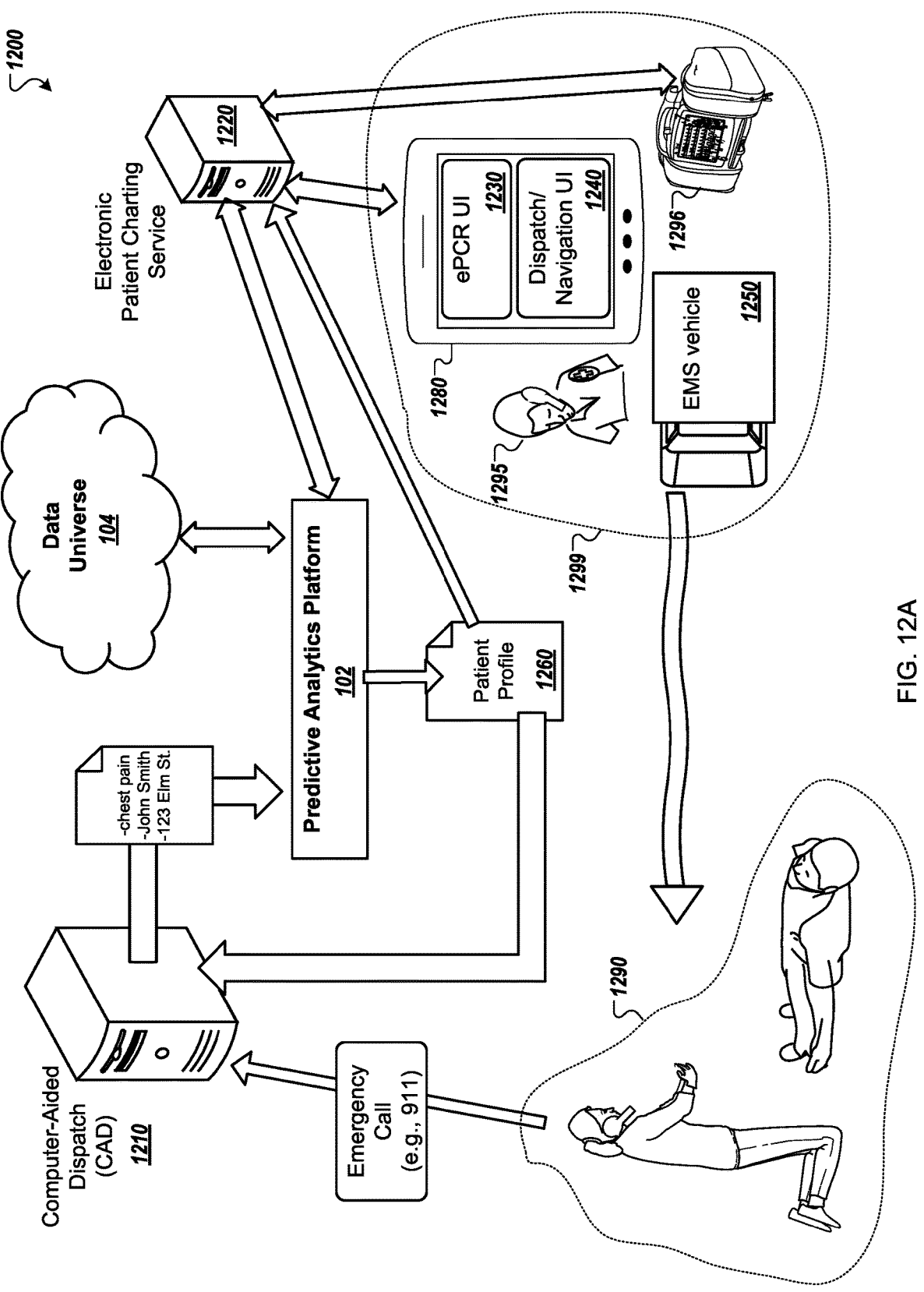
FIGS. 12A and 12B are flow diagrams of an example process for using a predictive analytics platform to coordinate and supplement information related to an emergency medical transport request between a computer-aided dispatch system and an electronic patient charting service.

Referring to FIG. 12A, an example system 1200 including the predictive analytics platform 102 communicatively coupled to a computer aided dispatch (CAD) 1210 and an electronic patient charting service 1220 is shown. The platform 102 and the CAD 1210 are communicatively coupled via a long-range network such as, for example, the Internet and/or a cellular network. Similarly, the platform 102 and the electronic patient charting service 1220 are communicatively coupled via a long-range network such as, for example, the Internet and/or a cellular network. In an implementation, the electronic patient charting service 1220 may be communicatively coupled with the CAD 1210. In an implementation, the platform 102, the CAD 1210, and/or the electronic patient charting service 1220 may be components of a cloud-based software as a service (SaaS) platform.

In an exemplary scenario, a bystander at the scene 1290 of an emergency places an emergency call (e.g., a 911 call) and provides emergency information received by the CAD 1210. At this initial stage of an emergency response, the emergency information provided to the CAD 1210 may include the nature of the emergency (e.g., chest pain, drug overdose, cardiac arrest, automobile accident, poisoning, etc.) along with some initial demographic information for the victim. For example, the initial demographic information may include a first name, a last name, and an address. Often, in an emergency situation, the initial demographic information may be minimal information. The victim may be unconscious and/or may be in the company of casual acquaintances or strangers without access to specific information like a social security number, insurance provider, primary care physician, insurance sponsor, etc. The CAD 1210 may provide this initial demographic information to the predictive analytics platform 102 in real-time at the outset of the EMS response to an emergency situation. Additionally, the CAD 1210 may provide this initial demographic information to an EMS agency that may dispatch an EMS crew 1295. The EMS crew 1295 may operate in a mobile environment 1299 that includes an EMS vehicle 1250, at least one mobile device 1280, and one or more items of medical equipment 1296. The medical equipment 1296 may include one or more of a defibrillator, a patient monitor, a ventilation system, a first aid kit, an ultrasound device, a temperature management device, an automated compression device, a drug delivery device, and/or another item of medical equipment for patient monitoring and/or therapy delivery. The electronic patient charting service 1220 may service a user interface at the mobile device 1280 to capture patient charting information to populate an electronic patient care record (ePCR). The ePCR may include a detailed record of treatments and interventions provided to the patient by the caregivers along with patient transport information. The predictive analytics platform 102 may receive the ePCR from the charting service 1220 and may populate a medical claim with information recorded in the ePCR and/or utilize the medical procedure codes indicated by and/or recorded in the ePCR to estimate payments as described above. In an implementation, the medical device (s) 1296 may communicatively couple to the charting service 1220 and/or the mobile device 1280 to provide medical treatment information for automatic recordation in the ePCR.

The mobile device 1280 may provide one or more of an ePCR user interface (UI) 1230 and a dispatch/navigation UI 1240. In various implementations, the ePCR UI 1230 and the dispatch/navigation UI 1240 may be user interfaces for multiple applications or a single UI for a combined application. The charting service 1220 may control the ePCR application on the mobile device 1280 to automatically enter this initial demographic information into the patient charting file for the emergency event at the patient scene 1290.

Figure 12B:
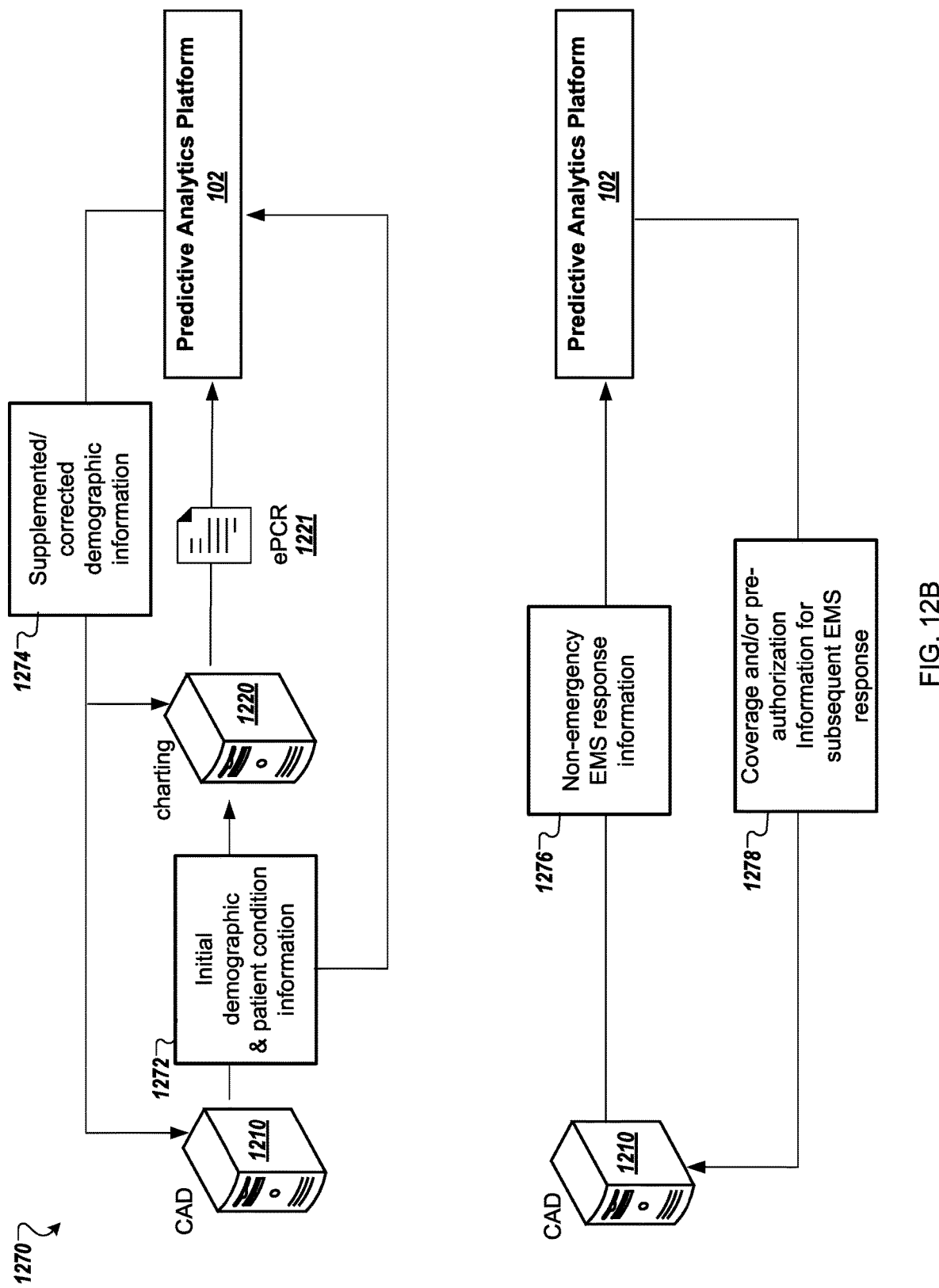

Referring to FIG. 12B, some examples of information flow between entities in FIG. 12A are shown in a process 1270. For example, during provision of EMS services for an emergency situation, the CAD 1210 may provide initial demographic and patient condition information 1272 to the charting service 1220 and the predictive analytics platform 102. The charting service 1221 may further provide the ePCR 1221 documenting the emergency response to the platform 102. The platform 102 may provide supplemented and/or corrected. demographic information back to the charting service 1220 and/or the CAD 1210. As described further below, the charting service 1220 may utilize the supplemented and/or corrected demographic information to obtain medical records for the victim that may enable improved care for the victim. Additionally, the platform 102 may provide insurance coverage information to the charting service 1220 for use in disposition and transport of the patient to a preferred provider based on coverage if the preferred provider has the same level of medical care capability and is approximately the same distance from the emergency scene so that patient care is not compromised based on coverage. However, in the case of equivalent medical care, it may be financially and medically advantageous to the patient to proceed initially to a preferred and known provider. The CAD 1210 may store demographic information for subsequent responses by EMS for the same patient to provide more efficient care in these subsequent responses. As another example, the CAD 1210 may provide non-emergency response information 1276 to the platform 102. The non-emergency response information 1276 may be information for the provision of EMS services for a scheduled transport, such as dialysis or chemotherapy and this information may include patient demographic and/or medical information. The platform 102 may return coverage and/or pre-authorization information back to the CAD 1210 for use in a subsequent provision of non-emergency EMS services for the same patient. Scheduled transport is often for a treatment, like dialysis, that is repeated frequently for the same patient. Thus, with the information from the platform 102, the full analysis of transport vehicle type, pre-authorization, transport destination, estimated costs and reimbursements may all be available at the outset to the benefit of both the patient and the care providers.

The examples shown in FIGS. 12A and 12B may enable the platform 102 to improve the efficiency, and therefore the efficacy, of care provided to a victim of an emergency event. For example, the efficacy and efficiency of care provided to a victim of an emergency event may be dramatically improved if the EMS crew has more information about the victim than the minimal information provided by the CAD 1210. This additional information also beneficially supplements caregiver observations on scene. Therefore, while the EMS vehicle 1250 is on route to the scene 1290 over a short time frame (e.g., 2-15 minutes) given the emergency nature of the EMS deployment, the predictive analytics platform 102 may access the data universe 104 to generate a patient profile 1260 before or substantially concurrently with the arrival of the EMS crew at the patient scene 1290.

In some implementations, the predictive analytics platform 102 implements one or more of the methods and/or processes described above to generate the patient profile 1260. For example, the predictive analytics platform 102 may perform at least a portion of the method 900 of FIG. 9 to correct and/or update patient demographic data based on the information provided by the CAD 1210. The predictive analytics platform 102 may identify one or more payers (e.g., active insurance coverage) associated with the victim using the method 310 of FIG. 3B. Further, the predictive analytics platform 102 may identify a liability insurance payer using at least a portion of the method 500 of FIG. 5A, for example if the emergency scene involves a vehicle accident. Using this information, the predictive analytics platform 102 may identify, for example using at least a portion of the methods 300, 320, and/or 330 of FIGS. 3A,

3C, and 3D to determine likelihoods of payment being recovered from one or more payers and/or the patient. In embodiments where determining the likelihoods results in determining that the patient does not have active coverage or that the patient qualifies for additional coverage under one or more medical payment assistance programs, the predictive analytics platform 102 may identify, for example using at least portions of the method 600 of FIG. 6, options for coverage for an underinsured patient. Determining the likelihoods, in further embodiments involving active coverage, includes determining whether prior authorization is required for one or more services and, in some instances, requesting service authorization, as described in relation to the methods 400 410 of FIG. 4A and FIG. 4B.

The platform 102 may provide this profile 1260 to the CAD 1210 and/or to the ePCR. service 1220. In an implementation, the CAD 1210 may store all or a portion of the patient profile 1260 for a subsequent EMS response and deployment involving the same patient in order to improve the efficiency and efficacy of the subsequent response. In some implementations, the CAD 1210 may limit the stored information to a supplemented demographic profile. In an implementation, the ePCR service 1220 may auto-populate the patient charting file with the patient profile and/or may display at least a portion of the patient profile at the ePCR UI. In an example, the demographic and/or coverage information provided to the ePCR service 1220 may enable the ePCR service 1220 to access medical records for the patient with information that may enable improved care. For example, knowledge of a history of asthma or heart disease may improve care provided in an emergency. The access by the ePCR service 1220 to the medical records (e.g., as stored in a regional Health Information Exchange (HIE) or a hospital system electronic health record (EHR)) may be difficult or impossible based on only the patient information provided to the CAD and/or EMS caregivers on scene and without the supplements to this data available from the patient profile 1260. For example, the victim of the emergency may be unable to provide identification and/or medical provider information (e.g., the victim may be unconscious, incoherent, or confused). The amount of information about the victim may be limited to a name known by a bystander, some identification in the victim's possession (e.g., a driver's license), or a street address. If the platform 102 is able to supplement the demographic information and/or medical provider information and provide this information to the ePCR service 1220, the ePCR service 1220 may in turn use this information to access medical records that may enable improved care for the victim.

In an implementation, the EMS crew may become aware of additional patient information on scene and may provide this information to the predictive analytics platform 102. The platform 102 may utilize this additional information to supplement, correct, or otherwise modify the patient profile 1260 in real-time over the course of the emergency encounter.

Insurance and provider information in the patient profile 1260 may enable the EMS crew to transport the victim to an appropriate destination. For example, given a choice of destinations, the EMS crew may be able to transport the patient to an in-network or otherwise preferred provider. Additionally, the CAD 1210, the platform 102, and/or the ePCR service 1220 may communicatively couple with the transport destination and provide at least a portion of the patient profile 1260. In this manner, the transport destination may be apprised of an imminent arrival with the additional information from the patient profile 1260 that enables improved and more efficient care.

FIG. 13A illustrates a flow diagram of an example process 1300 for training machine learning models and deriving combined data models directed to predicting the identity of payers based on subscriber identification format. The coverage verification engine 216 of FIG. 2, for example, may apply data derived by the data models of the process 1300 to verify a patient's insurance coverage. The data models developed by the process 1300, in another example, may be used by the method 300 of FIG. 3B to verify a patient's insurance coverage (312).

In some implementations, the process 1300 begins with accessing subscriber identifiers 1304*a* and corresponding payer identifiers 1304*b* from a storage region 1302. The subscriber identifiers 1304*a* (e.g., numeric or alphanumeric member identification codes) and corresponding payer identifiers 1304*b* (e.g., names, identification codes, etc.), for example, may be accessed from the data universe 104 of FIG. 1A. The subscriber identifiers 1304*a* and corresponding payer identifiers 1304*b*, for example, may be stored as part of patient records represented by the patient data 240 of FIG. 2 (e.g., in the data repository 210). Although described in relation to a one-to-one relationship between subscriber identifier 1304*a* and payer identifier 1304*b*, in some embodiments, the payer identifiers 1304*b* include hierarchical payer information (e.g., a national parent company identification as well as one or more regional payer identifications for each region (e.g., state, municipality) in which the national parent company provides coverage), such as, in an illustrative example, Acme Insurance of New England, Acme Insurance of California, and Acme Insurance of Ohio.

In some implementations, the subscriber identifiers 1304*a* and corresponding payer identifiers 1304*b* are provided to a first learning model training engine 1308*a* to train a learning model 1310*a* to recognize patterns of subscriber identifiers 1304*a* corresponding to each payer represented by the payer identifiers 1304*b*. The patterns, for example, may include a total number of characters, a position of a series of alphabetic characters in relation to numeric characters within a given subscriber identifier, use of non-alphanumeric characters, and/or other patterns that may be used to characterize a certain payer's subscriber identifiers.

The first learning model training engine 1308*a*, in some embodiments, includes a decision tree learning model algorithm such as a random forest model algorithm to classify subscriber identifiers as belonging to a given payer among a set of payers. The decision tree learning model algorithms, for example, provide strong accuracy on data sets appropriate to supervised learning (e.g., pre-matched known truth data). In some embodiments, the first learning model training engine 1308*a* includes neural network-based analysis for categorizing subscriber identifiers by payers based on patterns within the subscriber identifiers, such as a recurrent neural network (RNN). The RNN, for example, may receive additional patient information, such as geographical region, age, sex, employer, etc. to identify subscriber patterns used to code the additional patient data. Other learning model algorithms and/or neural network-based analysis tools may be applied to train the learning model 1310*b*.

The patient records supplying the subscriber identifiers 1304*a* and payer identifiers 1304*b*, in some embodiments, include an unbalanced set of data, including records primarily representative of one to a handful of very large payers with a minority of the data representing smaller insurers. In such a circumstance, in some implementations, a data balancing engine 1306 evens the numbers of records of matched subscriber identifiers 1304*a* and payer identifiers 1304*b* to promote the learning of subscriber identifiers 1304*a* related to less popular payers. The data balancing engine 1306, for example, may undersample the data related to popular payers or oversample data to create copies of records related to the less popular payers.

In some implementations, the balanced set of the subscriber identifiers 1304*a* and corresponding payer identifiers 1304*b* are provided to a second learning model training engine 1308*b* to train a learning model 1310*b* to recognize patterns of subscriber identifiers 1304*a* corresponding to each payer represented by the payer identifiers 1304*b*. As described in relation to the learning model training engine 1308*b*, a variety of machine learning algorithms and/or deep learning analysis networks may be used to train the balanced learning model 1310*b*.

In some implementations, the balanced learning model 1310*b* is combined with the first (e.g., unbalanced) learning model 1310*a* by a data model combining engine 1308*c* to create a payer by subscriber ID format predictive model 1310*c* for matching a given subscriber identifier with a corresponding payer. The predictive model 1310*c*, in some embodiments, provides one or more likely payers based on a given subscriber identifier, where the payers are identified in reference to relative likelihood. In one example, the payers used to train the predictive model 1310*c* may be weighted based on likelihood of a given subscriber identifier corresponding to each payer. For example, weightings may be based in accordance with insurance industry statistical information regarding market share of subscribers. In another example, the weightings may be based on the statistical distribution in the training data where the training data is expected to be reasonably representative of the population as a whole.

Figures 1, 13B:
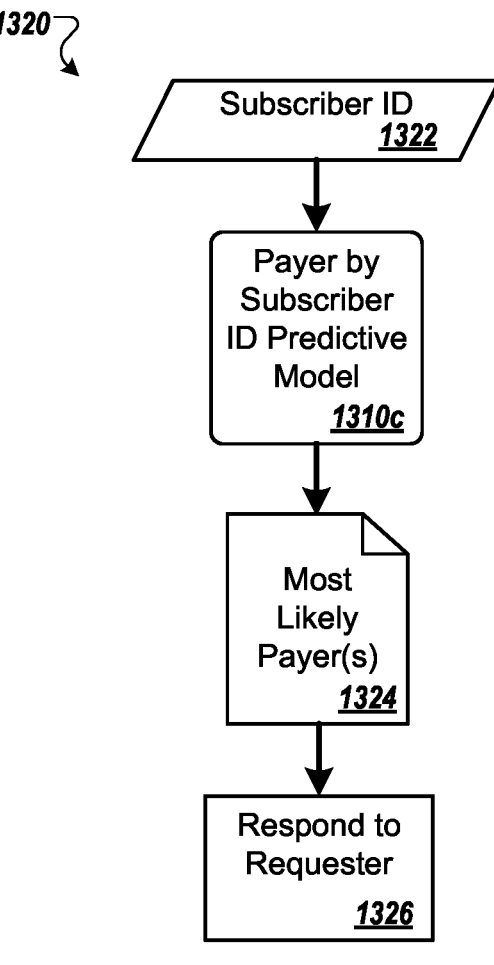
Figures 2, 13B:
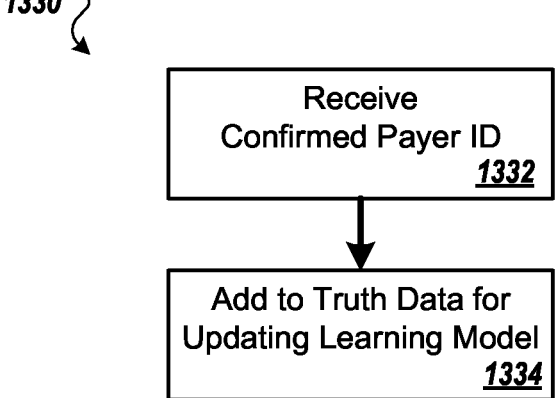
Figures 1, 13C:
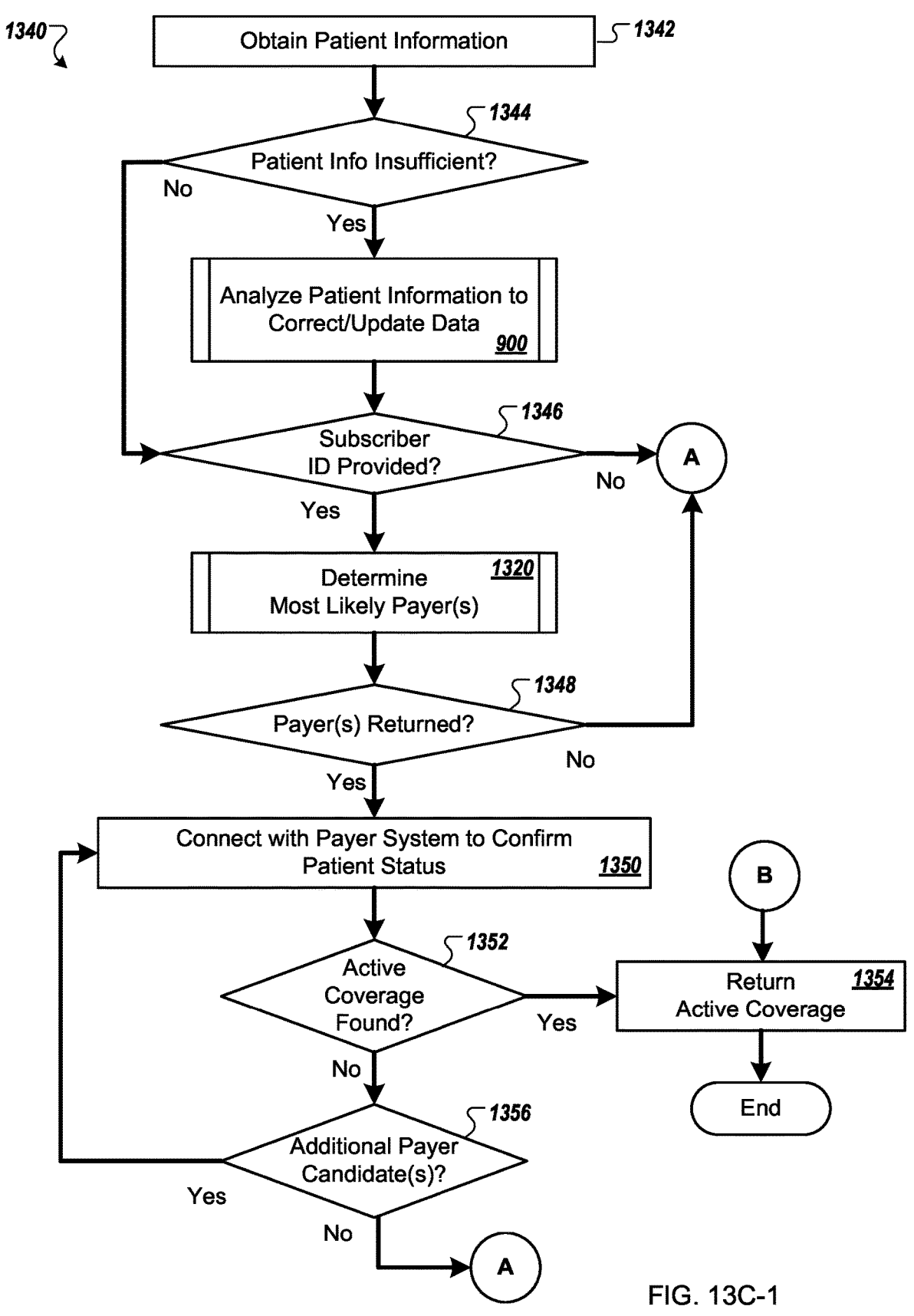
Figures 2, 13C:
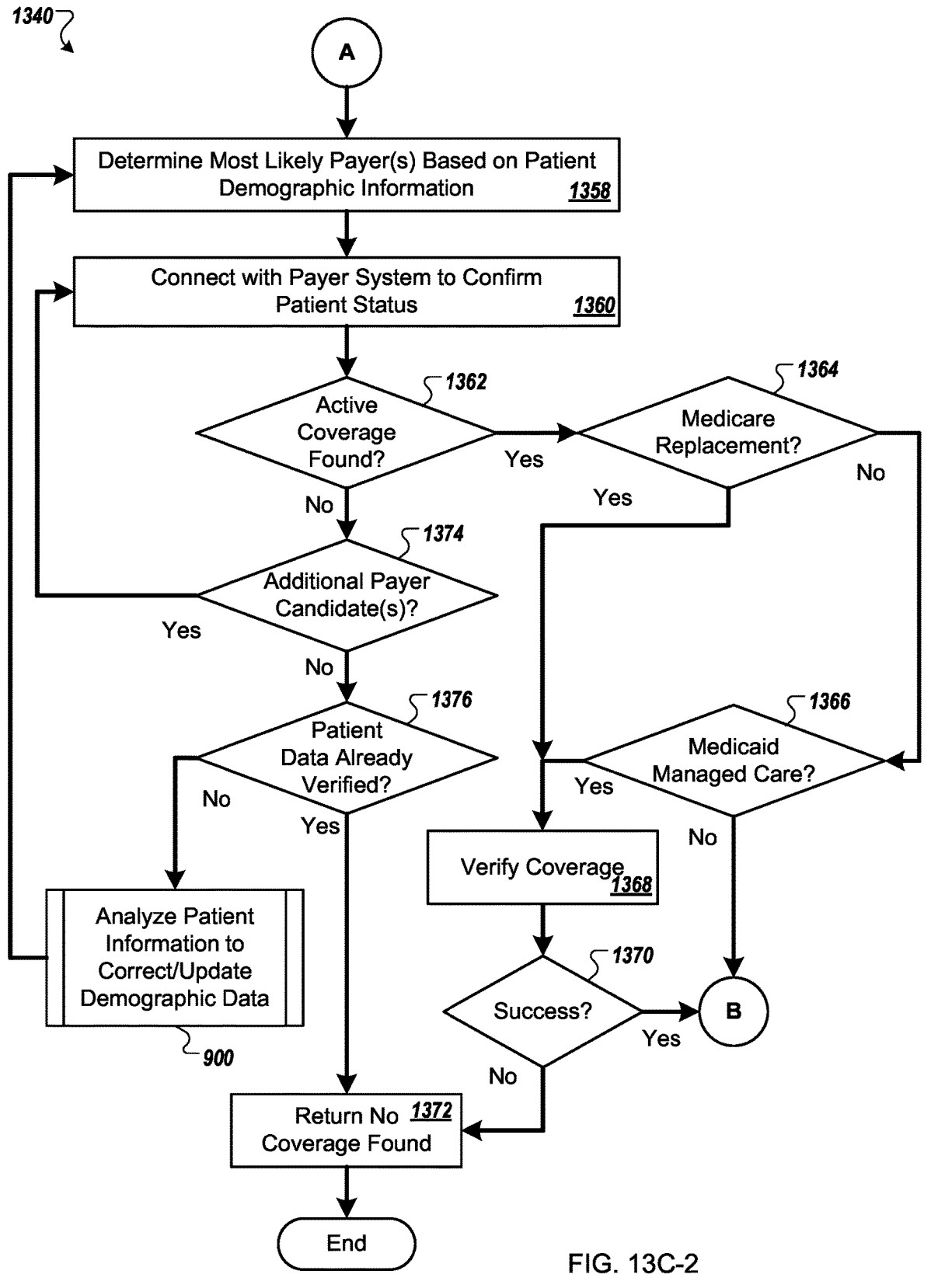

FIG. 13C-1 and FIG. 13C-2 illustrate a flow chart of an example method 1340 for identifying potential payers for a patient's medical treatments. Portions of the method 1340, in some examples, may be used by the method 300 of FIG. 3A, the method 310 of FIG. 3B, and/or the method 320 of FIG. 3C. The method 1340, for example, may be executed by the payer identification engine 218 of FIG. 2.

In some implementations, the method 1340 begins with obtaining patient information (1342). The patient information, for example, may be similar to patient information described in relation to operation 302 of the method 300 FIG. 3A.

In some implementations, if the patient information is insufficient (1344), the patient information is analyzed to correct and/or update the provided data (see, e.g., method 900 of FIG. 9).

In some implementations, if a subscriber identifier is provided (1346), the most likely payer(s) is determined (see method 1320). Turning to FIG. 13B-1, in some implementations, a subscriber identifier 1322 is provided to the payer by subscriber identifier predictive model 1310*c* to obtain a list of one or more most likely payers based on the format of the subscriber identifier 1322. The list, in some embodiments, may include a confidence level or rating associated with each payer of the one or more payers. For example, a percentage confidence level may be provided. The payers may be ranked in relation to likelihood of match. In some implementations, the list of most likely payers 1324 is provided in response to the requester (1326). The requester may have connected to an application programming interface (API), and the response may be submitted to the requester via the API. In another example, the payer may have submitted the request via a web service, and the results may be returned via the web service. Example web services include JSON and XML. The formatting and/or response path, in some embodiments, may be determined at least in part based upon settings associated with a user, a medical facility, or other account information.

Returning to FIG. 13C-1, in some implementations, if payers have been returned (1348), a current payer is confirmed by connecting with the payer system of each returned payer (1356) until an active patient status is identified (1350). The payers may be analyzed in order or in parallel.

In some implementations, if active patient coverage is identified (1352), the active coverage is returned (1354). The active coverage, for example, may be returned to the submitter of the patient information, such as a patient intake portal. The active patient coverage, for example, may be presented to intake personnel at a medical facility.

Turning to FIG. 13C-2, in some implementations, if active coverage is not found (1356), the most likely payer(s) are determined based on patient demographic information (1358). This is described, for example, in relation to operation 334 of the method 310 of FIG. 311

In some implementations, a current payer is confirmed by connecting with the payer system of each returned payer until an active patient status is identified (1360). The payers may be analyzed in order or in parallel.

In some implementations, if active coverage is found (1362), it is determined whether the coverage is a Medicare replacement (1364) or Medicaid managed care (1366), in which case coverage is verified (1368). For example, replacement coverage may be verified if it has not yet been verified. If verification is unsuccessful (1370), in some implementations, a status of no coverage found is returned (1372).

If, instead, verification was successful (1370) or the active coverage found (1362) is not a Medicare replacement or Medicaid managed care (1364, 1366), the active coverage is returned (1354).

Returning to operation 1364, if active coverage was not found, and the patient data has already been verified (1376), no coverage found is returned (1372). If, instead, the patient data has not already been verified (1376), the patient information is analyzed to correct and/or update demographic data (see method 900 of FIG. 9), and the method 1340 returns to determining the most likely payer(s) based on the corrected and/or updated patient demographic information (1358).

Although described as a particular series of operations, in some embodiments, more or fewer steps may be included in the method 1340. For example, in some implementations, if active coverage is found (1352) based on payer(s) returned by the method 1320, a method 1330 of FIG. 13B-2 is invoked to provide a confirmed payer identifier (1332) for adding to truth data for updating the payer by subscriber identifier predictive model 1310c (1334). In further embodiments, certain steps of the method 1340 may be performed in a different order or in parallel. For example, rather than determining if there are additional payer candidates (1356), the method 1340 may connect with multiple payer systems in parallel to confirm patient status (1350). Other modifications of the method 1340 are possible.

Figure 14:
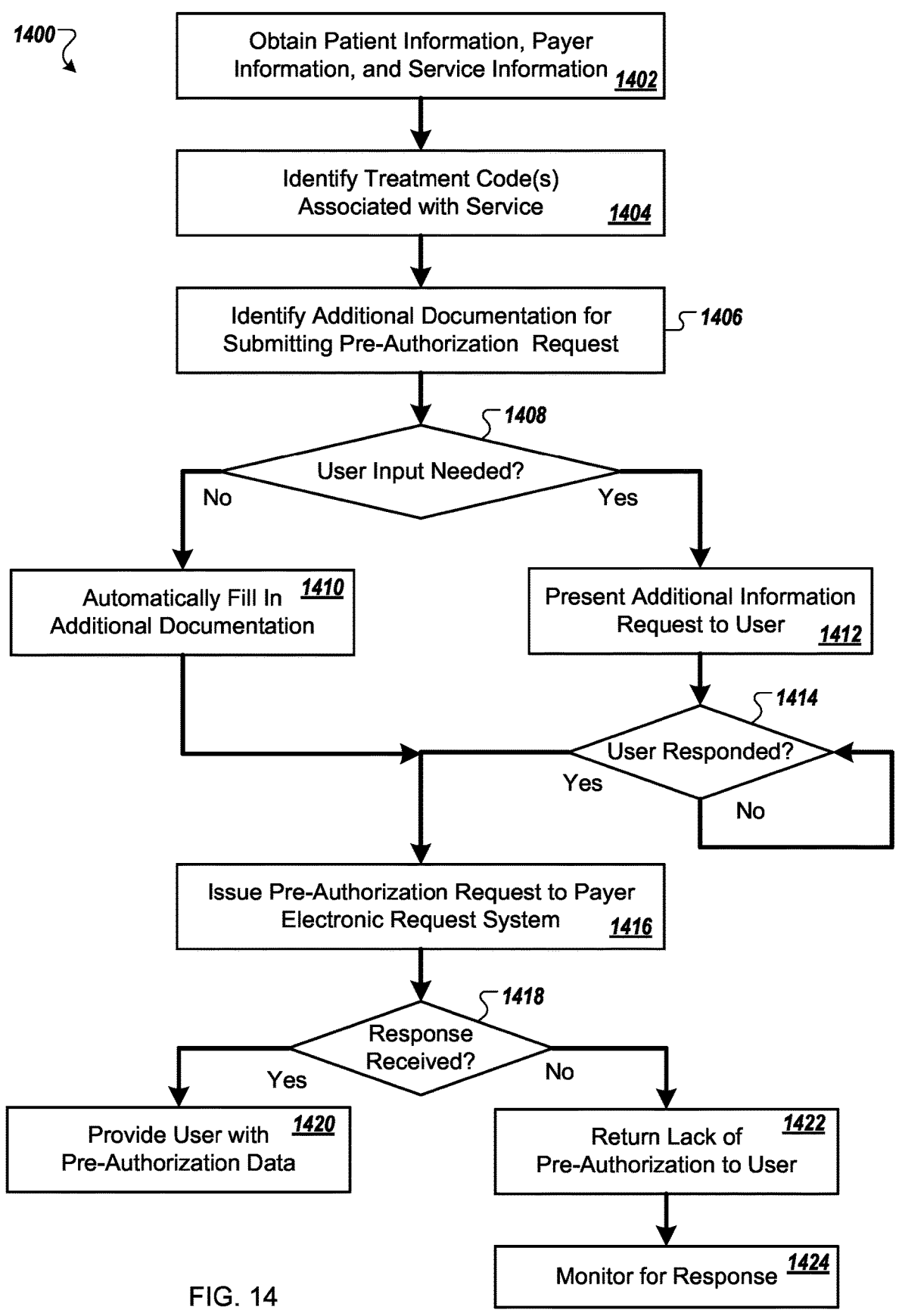
FIG. 14 illustrates a flow chart of an example method for automatically processing information for submitting a pre-authorization request.

FIG. 14 illustrates a flow chart of an example method 1400 for automatically processing information for submitting a pre-authorization request. The method 1400, for example, may be executed after determining that a pre-authorization is required by the patient's insurance company based on the patient's insurance plan. Portions of the method 1400, for example, may be performed in relation to the operations of the method 400 of FIG. 4A. The method 1400, for example, may be executed by the payer pre-approval request engine 234 of FIG. 2.

In some implementations, the method 1400 begins with obtaining patient information, payer information, and service information (1402). The patient information and service information may be obtained and may include similar information, for example, as described in relation to the patient demographic data 116 and the procedure codes 114 of FIG. 1A. In another example, the patient information and service information may be received as part of a medical claim as described in relation to operation 152 of the method 150 of FIG. 1B. The payer information, for example, may include a subscriber identifier and a payer identifier.

In some implementations, one or more treatment codes associated with the service are identified (1404). The treatment codes may be provided in the service information. If not, the service codes may be cross-referenced in relation to the treatment and, if applicable, the payer (e.g., to identify preferred service codes for the particular payer).

In some implementations, additional documentation for submitting a pre-authorization request is identified (1406). The documentation, for example, may include information required by the payer or based on the patient's plan provided by the payer. The documentation may further be identified based on the service or type of treatment being provided to the patient. In some examples, the documentation can include a request for reason for the procedure and/or additional details regarding diagnoses leading up to the procedure.

If user input is needed (1408), in some implementations, additional information requests are presented to a user (1412), and user responses are collected (1414). The information requests, for example, may be presented as a tillable form or data entry screen presented within a user portal. In another example, the documentation request may include a downloadable form requiring printing and marking with an official signature.

Otherwise, if user input is not needed (1408), in some implementations, additional documentation is automatically filled in (1410). For example, using the patient information and service information, the required details (e.g., date of treatment, location of treatment, etc.) may be pulled from system records and automatically entered in a format used by the payer's authorization service.

In some implementations, a pre-authorization request is issued to the payer's electronic request system (1416). The pre-authorization request may include subscriber information, service information including the treatment codes, and the additional documentation (if applicable). Submitting the pre-authorization request, in some examples, may include issuing the request to an application programming interface (API) of the payer system or issuing an electronic facsimile of the information to the payer system.

If a response is received (1418), in some implementations, the user is provided with pre-authorization data (1420). For example, if the payer system responds in real-time or near real-time with an acknowledgment and confirmation of authorization, the pre-authorization information received from the payer may be presented to the user.

If no response is received (1418), in some implementations, a lack of pre-authorization is returned to the user (1422), and the method 1400 continues to monitor for a response (1424). If the response continues to pend, for example, the user may be informed that the request is in-progress. The method 1400 may set a timer to check status in the future. For example, every X seconds or minutes the method 1400 may check for completion of the pre-authorization request.

Although described as a particular series of operations, in some embodiments, more or fewer steps may be included in the method 1400. For example, in some implementations, in the event of pre-authorization failure (e.g., refusal), the method 1400 may attempt an alternative treatment code or alert the user to intervene. In further embodiments, certain steps of the method 1400 may be performed in a different order or in parallel. For example, a portion of the additional documentation may be filled in automatically (1410) before or while other additional information is requested from the user (1412). Other modifications of the method 1400 are possible.

Figure 15A:
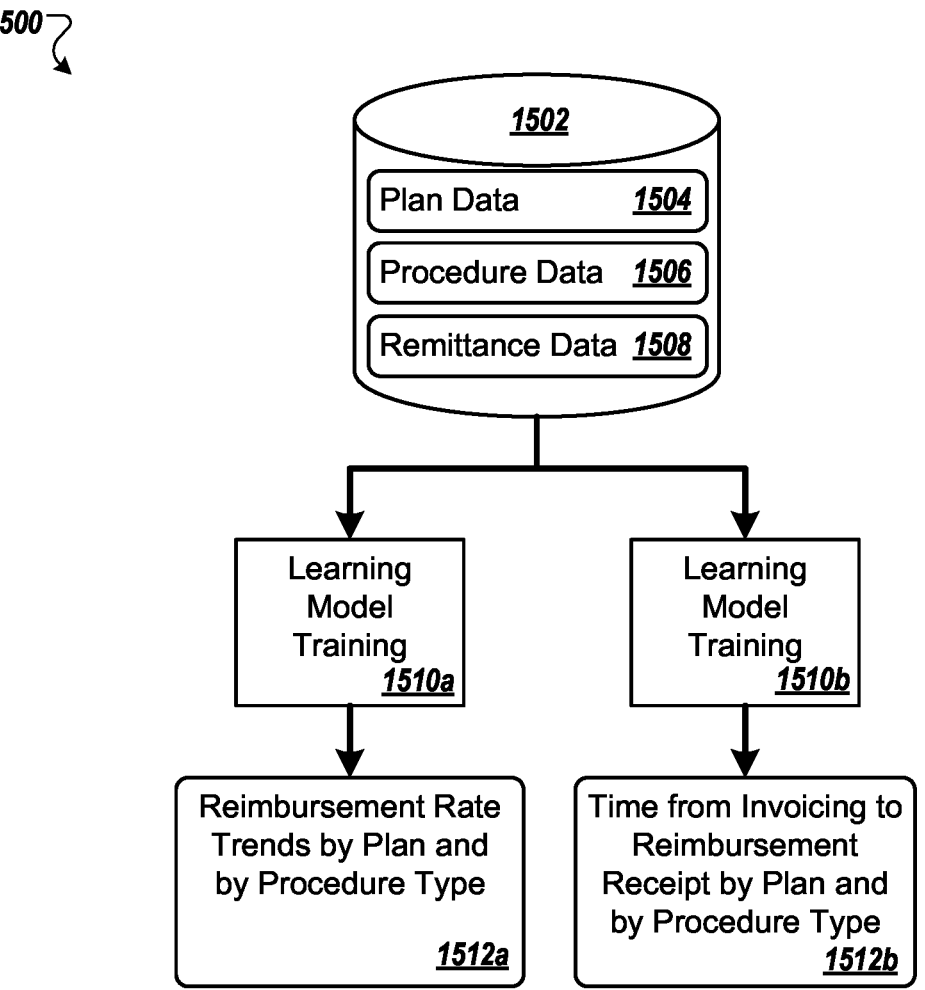
FIG. 15A illustrates a flow diagram of an example process for training machine learning models to estimate reimbursement rates and time to invoicing.

FIG. 15A illustrates a flow diagram of an example process 1500 for training machine learning models to estimate reimbursement rates and time to invoicing. The machine learning models generated by the process 1500, for example, may be used by the method 320 of FIG. 3C for calculating a remittance estimate. In another example, the payment trends analysis engine 239 of FIG. 2 (e.g., applied in the process 700 of FIG. 7) may apply the machine learning models generated by the process 1500 to determine payment patterns 712, 714.

In some implementations, the process 1500 begins with accessing plan data 1504, procedure data 1506, and remittance data 1508 from a storage region 1502. The plan data 1504, for example, may correspond to the plan data 244 as described in relation to FIG. 2. The procedure data 1506 may correspond to the procedure data 248 as described in relation to FIG. 2, and the remittance data 1508 may correspond to the remittance data 268 as described in relation to FIG. 2. The plan data 1504, procedure data 1506, and remittance data 1508 may be linked through a particular subscriber (e.g., by subscriber identifier). In some implementations, the plan data 1504, procedure data 1506, and remittance data 1508 are collected from the data universe 104 (e.g., historic claims data 120) described in relation to FIG. 1A.

In some implementations, the plan data 1504, procedure data 1506, and remittance data 1508 are provided to a first learning model training engine 1510a to train a reimbursement rate learning model 1512a to recognize patterns ("trends") in reimbursement rate by procedure type for each plan of each payer. The procedure types, in a first example, may include a treatment code or set of treatment codes (e.g., for a service involving multiple treatments such as a surgery involving anesthesia, a surgical procedure, implant hardware, and setting in a cast, etc.). In another example, the procedure types may be determined by analyzing only a portion of the full treatment code, such that related or similar codes are analyzed together. In one example historic data may be analyzed to determine codes & remittance related to a service type (e.g., hip replacement).

The first learning model training engine 1510a, in some embodiments, includes a decision tree learning model algorithm such as a random forest model algorithm to estimate payment per treatment type based on the remittance received in relation to the claims data used for training. The decision tree learning model algorithms, for example, provide strong accuracy on data sets appropriate to supervised learning (e.g., pre-matched known truth data). In some embodiments, the first learning model training engine 1510a includes neural network-based analysis, such as a recurrent neural network (RNN). The RNN, for example, may consider additional claims information, such as a geographical region of the treatment facility, type of treatment facility, and/or pre-authorization status to analyze reimbursement trends. Other learning model algorithms and/or neural network-based analysis tools may be applied to train the reimbursement rate learning model 1512a.

In some implementations, the plan data 1504, procedure data 1506, and remittance data 1508 are provided to a second learning model training engine 1510b to train a learning model 1512b to predict a time (e.g., number of days and/or weeks) from invoicing to reimbursement receipt by plan and by procedure type. As described in relation to the learning model training engine 1308b, a variety of machine learning algorithms and/or deep learning analysis networks may be used to train the time to invoicing learning model 1512b.

Figures 1, 15B:
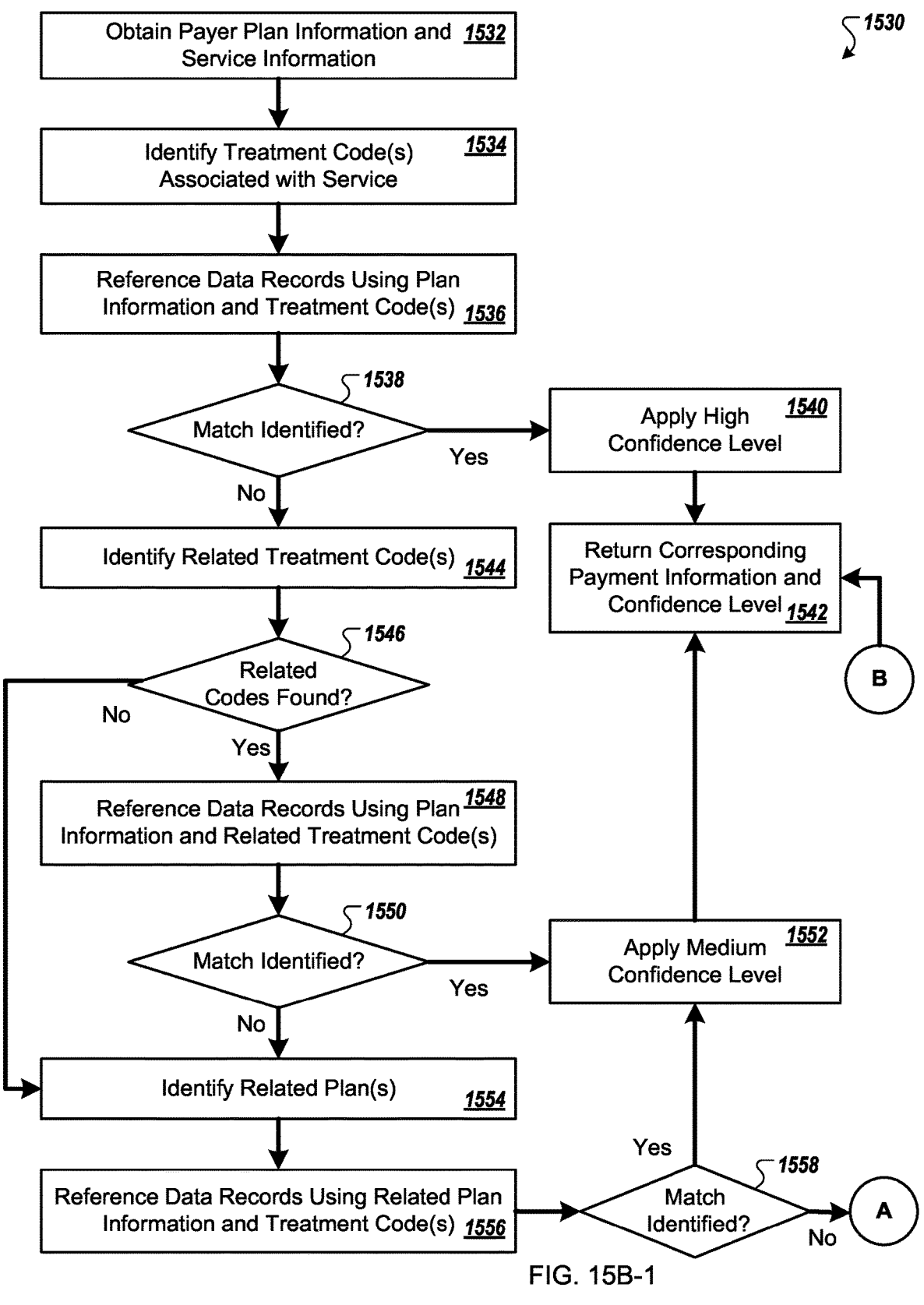
Figures 2, 15B:
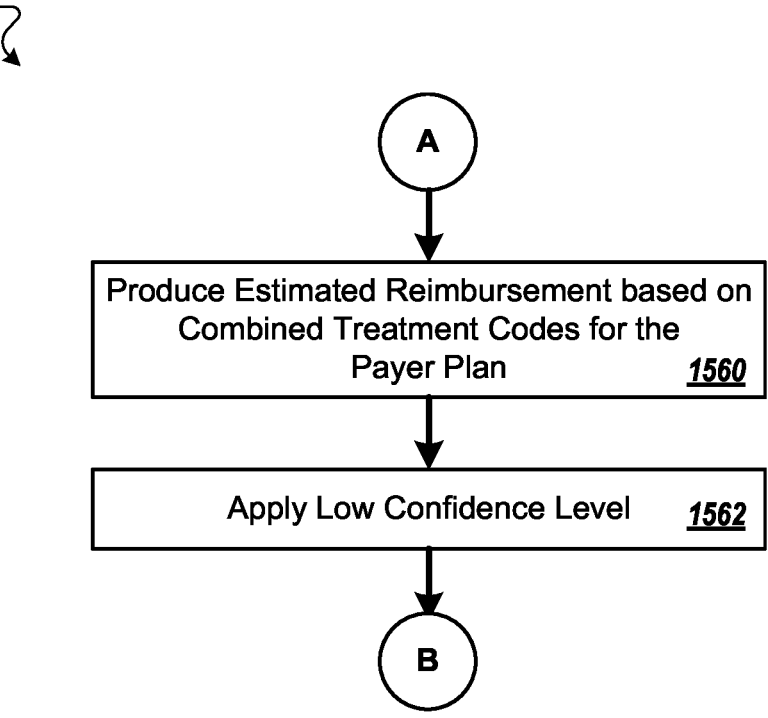

FIG. 15B-1 and FIG. 15B-2 illustrate a flow chart of an example method 1530 for estimating reimbursement amounts for services. The method 1530, for example, may be used by a medical facility to anticipate cash flow. For example, the payment trends analysis engine 272 and/or the projected revenue analysis engine 270 of FIG. 2 may execute the method 1530.

In some implementations, the method 1530 begins with obtaining payer plan information and service information (1532). The information may be obtained, for example, in a similar manner as described in relation to operation 1402 of the method 1400 of FIG. 14.

In some implementations, one or more treatment codes associated with the service are identified (1534). The treatment code(s) may be identified, for example, in a similar manner as described in relation to operation 1404 of the method 1400 of FIG. 14.

In some implementations, data records are referenced using plan information and the treatment code(s) (1536). For example, historic data records such as the plan data 244, procedure data 248, and remittance data 268 of FIG. 2 may be referenced to identify a matching plan and matching treatment codes. In an illustrative example, a relational database may be queried to reference the data records. In another example, a computerized data network, such as the data universe 104 of FIG. 1A, may be queried to identify matching information. The matching information, for example, may be limited to a current year or a current quarter, depending, for example, upon a schedule of reimbursement rate adjustments by the particular plan. If a match is identified, the corresponding reimbursement amount may be accessed.

In some implementations, if a match is identified (1538), a high confidence level is applied (1540) and the corresponding payment information and confidence level are returned (1542). Confidence levels may represent a similarity between the current plan information, service information, and timeframe. For example, the confidence level may be adjusted relative to a time period of the reimbursement in relation to the current date. In an illustrative example, a matching record within the same billing year or calendar year may correspond to the highest confidence level, while a matching record from a prior billing year may be accorded a lower confidence level. The confidence levels, in an illustrative example, include modifiers of "high," "medium," and "low." In another example, the confidence levels are accorded a percentage confidence, up to 100% for a full match (e.g., plan, billing codes, and timeframe).

In some embodiments, the confidence level and payment information are returned to a requesting algorithm or computing system via an API. The confidence level and payment information, for example, may be provided via an API or other portal data transfer for presentation to a requesting user. In other embodiments, the confidence level and payment information are stored in a location accessible to a requesting computing system for later access.

If a match is not identified (1538), in some implementations, one or more related treatment codes are identified (1544). The related treatment codes, for example, may correspond to a different coding system or a closely related treatment code in the same coding system. The related treatment codes, in some embodiments, are accessed using a look-up table storing similar codes. For example, certain plans may prefer one code over another to reference a particular treatment.

If related code(s) are found (1546), in some implementations, data records are referenced using the plan information and the related treatment code(s) (1548). The data records may be referenced, for example, as described in relation to operation 1536.

In some implementations, if a match is identified (1550), a medium confidence level is applied (1552) and the corresponding payment information and confidence level are returned (1542).

If no related codes are found (1546) or no match is identified using related codes (1550), in some implementations, one or more related plans are identified (1554). The related plans, in some examples, may include any similar plans provided by a same payer in a same geographic region, any closely related or same plans provided by a same payer in a different geographic region (e.g., Acme preferred provider organization (PPO) of Florida versus Acme PPO of Louisiana), and/or any historic plans of a same payer replaced by a new plan (e.g., the prior calendar year included a plan no longer offered in the present calendar year). The related plans may be identified, for example, using one or more machine learning algorithms comparing elements of a given payer's plans such as coverage levels, in network charge levels, out of network charge levels, and/or alternative treatments covered. In illustration, a high deductible plan of one major carrier may be deemed comparable to another major carrier's high deductible plan.

In some implementations, the data records are referenced using the related plan information and the treatment code(s) (1556). The data records, for example, may be accessed as described in relation to operation 1536.

If a match is identified (1558), in some implementations, a medium confidence level is applied (1552) and the corresponding payment information and confidence level are returned (1542).

If, instead, a match is not identified (1558), in some implementations, turning to FIG. 15B-2, an estimated reimbursement is produced based on combined treatment codes for the payer plan (1560). The combined treatment codes, in some embodiments, include treatment codes within a particular category. For example, the treatment codes all having the same characters except the last one or two characters may be accessed within the data records, and the reimbursement rates may be combined to determine an estimate. In some embodiments, the combined treatment codes include all treatment codes. For example, all reimbursement records corresponding to the particular plan may be combined to develop a reimbursement estimate. The records, in some examples, are combined by generating an average reimbursement rate, a median reimbursement rate, or a weighted average reimbursement rate. A weighted reimbursement rate calculation, in an illustrative example, may place greater emphasis on common reimbursements received in response to plan invoices (e.g., as opposed to rare treatment codes that may correspond to unusual procedures). In combining the reimbursement rates to determine the reimbursement estimate, in some embodiments, the lowest reimbursement rate(s) and/or the highest reimbursement rate(s) may be discarded to avoid skewing results based upon outlier information. In some embodiments, the reimbursement rate trends by plan and by procedure type 1512a generated by the machine learning process 1500 described in relation to FIG. 15A are accessed to produce the estimated reimbursement.

In some embodiments, databases of general procedure costs by region may be accessed. In illustration, the database of medical and hospital costs maintained by FAIR Health, Inc. of NY, NY may be accessed, using a zip code of the medical provider, to determine a going rate for the service(s) being provided to the patient.

In some implementations, a low confidence level is applied (1562), and the corresponding payment information and confidence level are returned (1542).

Although described as a particular series of operations, in some embodiments, more or fewer steps may be included in the method 1530. For example, in some implementations, related plans may be referenced using related treatment codes to identify a match (e.g., at a confidence level somewhere between the medium confidence level and the low confidence level). In further embodiments, certain steps of the method 1530 may be performed in a different order or in parallel. For example, related plans and related treatment codes may be referenced in parallel to identify a best match for the current treatment code(s) and payer plan. Other modifications of the method 1530 are possible.

Figures 16A, 16B:
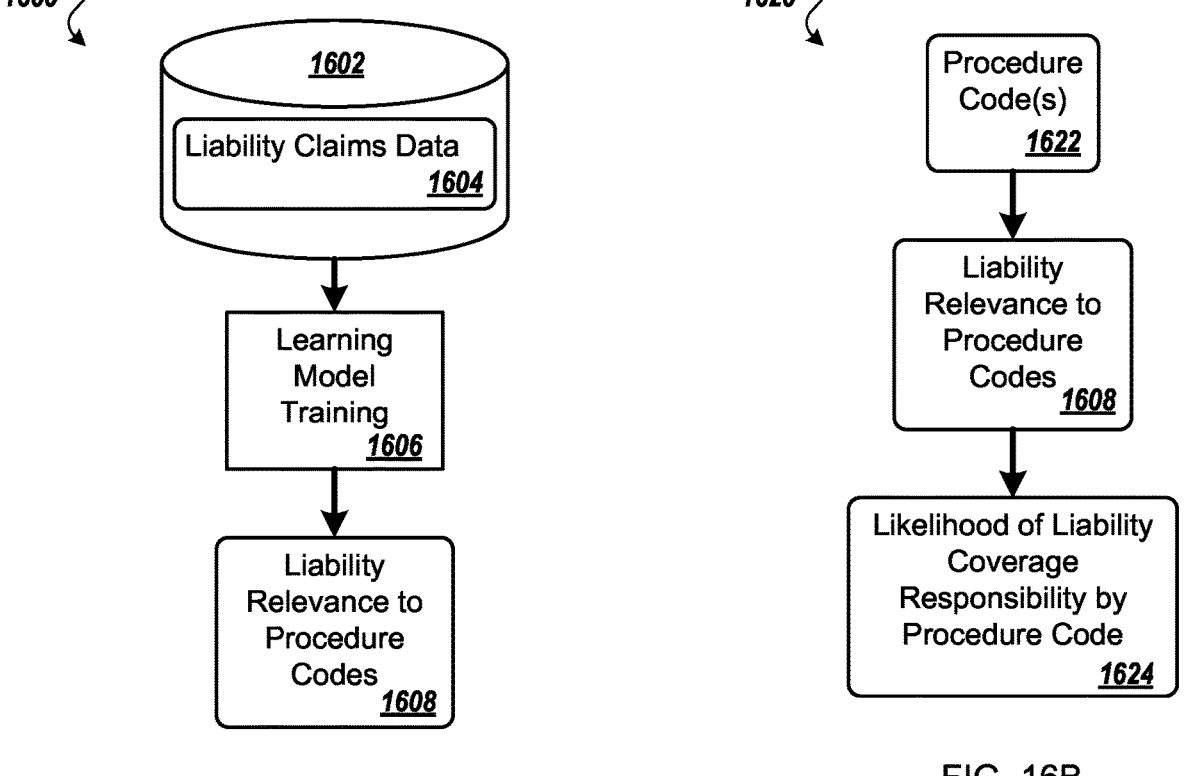
FIG. 16A illustrates a flow diagram of an example process for training a machine learning model directed to predicting whether liability coverage is applicable to medical services.
FIG. 16B illustrates a flow diagram of an example process for applying the machine learning model of FIG. 16A.

FIG. 16A illustrates a flow diagram of an example process 1600 for training a machine learning model directed to predicting whether liability coverage is applicable to medical services. The machine learning model generated by the process 1600, for example, may be applied by the process 500 of FIG. 5F to determine whether a liability payer is likely to be primary coverage (see operation 514).

In some implementations, the process 1600 begins with accessing liability claims data 1604 from a storage region 1602. The liability claims data 1604, for example, may be a portion of the claims data 256 of FIG. 2 corresponding to any payer of the payer data 242 that is a liability payer and/or any plan of the plan data 244 that is a liability plan. Further, rather than and/or in addition to claims data 1604, the data may include remittance data 268 of FIG. 2 corresponding to a liability payer and/or liability plan. In using remittance data, for example, the training data for the machine learning model may include only those claims actually paid by a liability payer.

In some implementations, the liability claims data 1604 is provided to a learning model training engine 1606 to train a learning model 1608 to predict a likelihood of liability coverage responsibility based on procedure code. In the event of remittance data, the remittance data may be cross-referenced with the claims data 1604 to obtain the procedure codes (e.g., in the event that the remittance data lacks procedure codes). In some implementations, the learning model training engine 1606 recognizes frequency of each procedure code discovered within the liability claims data 1604. Further, the learning model training engine 1606 may recognize type of liability payer (e.g., worker compensation liability payer covering a workplace injury, vehicle liability payer covering injury due to a vehicle accident, etc.) and associate certain payer codes as being more relevant to certain types of liability payer.

The learning model training engine 1606, in some embodiments, includes a decision tree learning model algorithm such as a random forest model algorithm to classify procedure codes as being relevant to liability payers. The decision tree learning model algorithms, for example, provide strong accuracy on data sets appropriate to supervised learning (e.g., pre-matched known truth data). In some embodiments, the learning model training engine 1606 includes neural network-based analysis for establishing likelihoods of each payer code as being relevant to liability coverage, such as a recurrent neural network (RNN). The RNN, for example, may receive additional information, such as commonality of the payer codes across all claims, not just liability claims, to adjust likelihoods accordingly. Other learning model algorithms and/or neural network-based analysis tools may be applied to train the learning model 1608.

Figures 1, 16C:
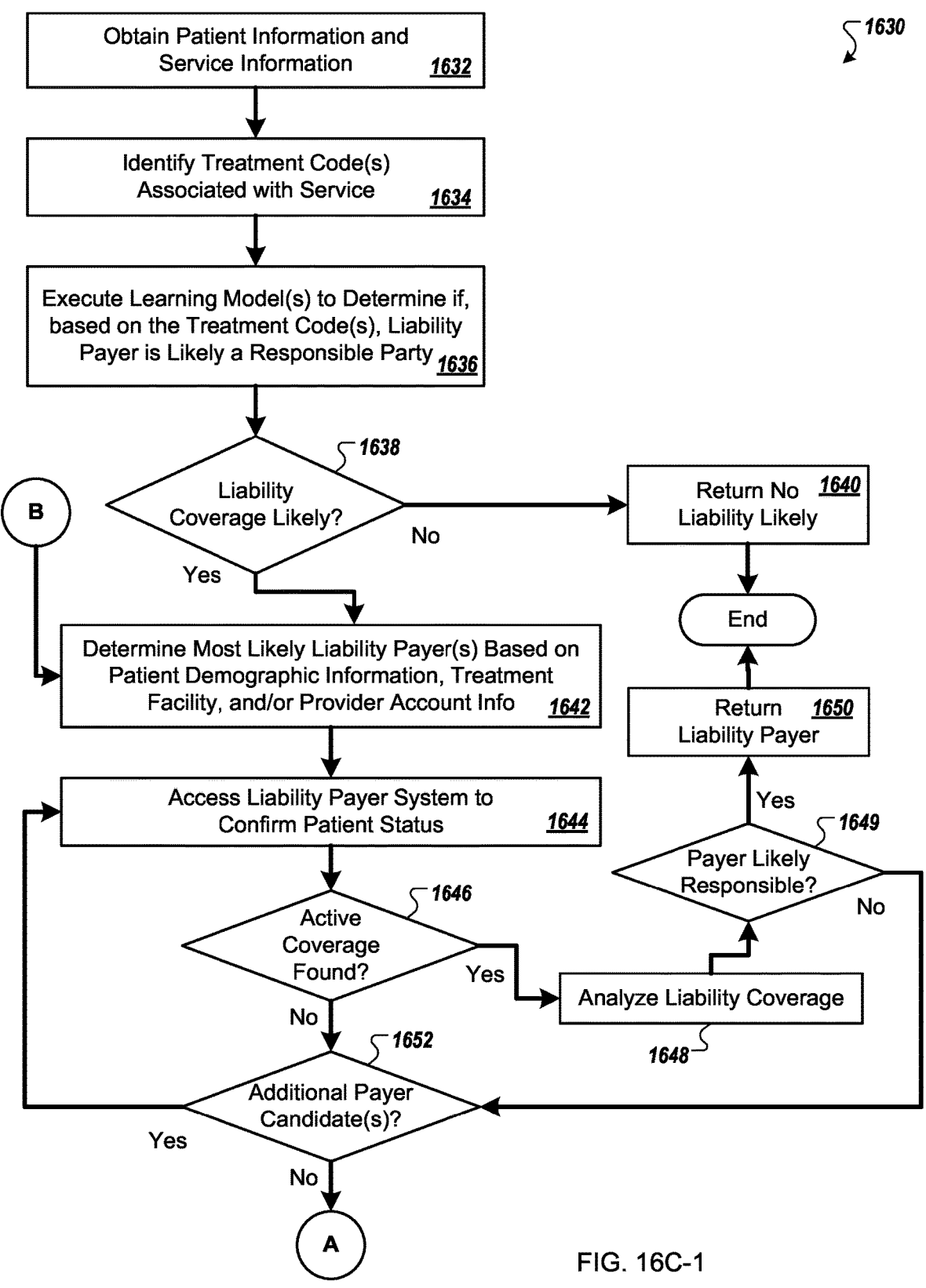
Figures 2, 16C:
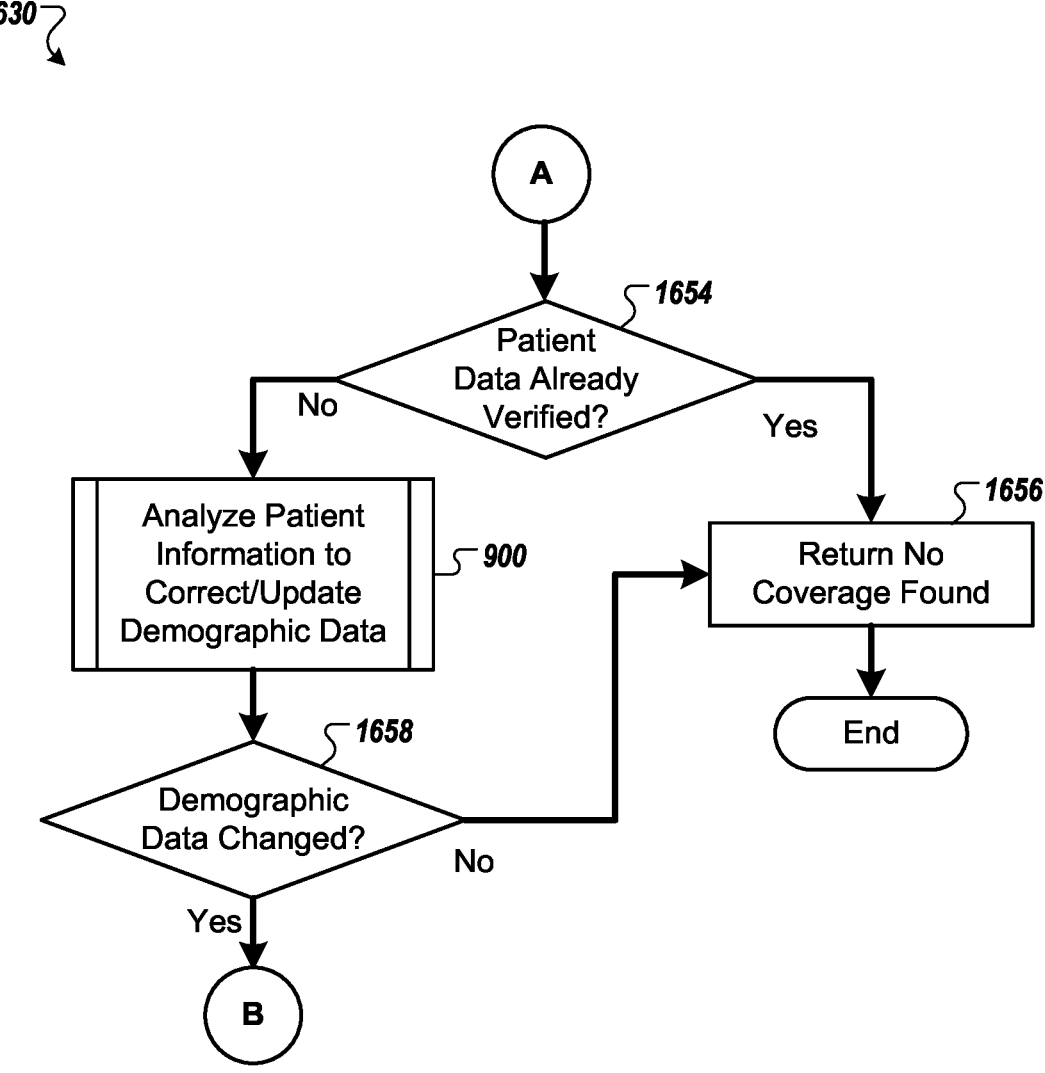

FIG. 16C-1 and FIG. 16C-2 illustrate a flow chart of an example method 1630 for determining whether a liability payer is likely responsible for payment for medical services rendered to a patient. Portions of the method 1630, for example, may be used by the method 500 of FIG. 5A and/or the method 520 of FIG. 5B. The method 1630, for example, may be executed by the liability applicability analysis engine 235 of FIG. 2.

In some implementations, the method 1630 begins with obtaining payer plan information and service information (1632). The information may be obtained, for example, in a similar manner as described in relation to operation 1402 of the method 1400 of FIG. 14.

In some implementations, one or more treatment codes associated with the service are identified (1634). The treatment code(s) may be identified, for example, in a similar manner as described in relation to operation 1404 of the method 1400 of FIG. 14.

In some implementations, one or more learning models are executed to determine if, based on the one or more treatment codes, a liability payer is likely to be a responsible party (1636). Turning to FIG. 16B, a flow diagram of an example process 1620 for applying the machine learning model 1612 of FIG. 16A, in some implementations, begins with receiving one or more procedure codes (1622). The procedure code(s), for example, may be obtained from the service information provided to the method 1630 in operation 1632. The method 1630, for example, may provide the procedure code(s) via an application programming interface (API) or program call.

The process 1620, in some implementations, supplies the procedure code(s) 1622 to the liability relevance to procedure codes machine learning model 1608 to determine a likelihood of liability coverage responsibility for each of the procedure code(s) 1624. The likelihood, in some examples, may include a percentage likelihood (e.g., out of 100% certainty), a scaled likelihood (e.g., on a relative scale of 1 to N), or a category likelihood (e.g., likely, uncertain, or unlikely, etc.).

In some implementations, the likelihoods of liability coverage responsibility by procedure code 1624 are returned to the method 1630 (e.g., via the API or a return call from the program).

Returning to FIG. 16C-1, in some implementations, if liability coverage is unlikely, a no liability likely response is returned (1640).

If, instead, liability coverage is likely (1638), in some implementations, one or more most likely liability payers are determined based on the patient demographic information, the treatment facility, and/or provider account information (1642). Determining likelihood, for example, may be based on a percentage or scale threshold, such as an 80% or above likelihood or at least a 4 rating on a 1 to 5 confidence scale. In some embodiments, identifying the most likely liability payer(s) includes identifying at least one most likely liability payer based on a geographic region identified within the demographic data. Identifying the most likely liability payer(s) may include identifying the at least one most likely liability payer based on the geographic region of the treatment facility and/or a payer's relationship (e.g., in-network or preferred provider status) with the treatment facility. The payer account information, for example, may include type of payer (e.g., ambulance company, hospital, surgical center, etc.). A combination of the type of payer and details regarding the service information, for example, may provide clues indicative of liability. In illustration, the combination of an ambulance company payer and a pick-up location of a street intersection may be indicative of collision.

In some implementations, the liability payer system(s) (1652) are accessed (1644) to confirm patient status (1646). For example, a request for active coverage related to the patient may be submitted to the liability payer system. In illustration, the liability payer system may include an application programming interface (API) or a facsimile number for submitting a request to the liability payer system.

In some implementations, if active coverage is found (1646), liability coverage is analyzed to determine if the plan is likely responsible for the financial reimbursement (1648). The procedure codes, for example, can provide clues to the type of incident. If there is a broken bone from impact by a vehicle, for example, then automobile liability insurance may be involved. Conversely, if the procedure codes are generally indicative of a pedestrian falling into a seizure, then automobile liability insurance is not likely to be applicable. Machine learning, for example, may be used to identify procedure codes common to liability coverage-activating injuries by type of liability coverage using remittance data, similar to the process 1600 described in relation to FIG. 16A. For example, a process similar to the process 1620 of FIG. 16B may be activated to identify whether liability coverage is likely applicable based on procedure codes and type of liability payer.

If the liability payer is determined to be a likely responsible party (1649), in some implementations, the liability payer is returned (1650). For example, the liability payer may be returned to a user portal or logged in a computing system in relation to an open claim for later processing.

If, instead, the payer is not likely responsible (1649) or no active coverage is found (1646), in some implementations, if additional liability payer candidates were identified (1652), the method returns to accessing the next liability payer system to confirm patient status (1644).

If no additional payer candidates are available for analysis (1652), turning to FIG. 16C-2, if the patient data has not already been verified (1654), the patient information is analyzed to correct and/or update demographic data (see method 900 of FIG. 9).

If there is a change in demographic data (1658), in some implementations, the method 1630 returns to determining the most likely liability payer(s) based on the updated patient demographic information (1642).

If, instead, the patient data has already been verified (1654) and no active coverage is found (1646), in some implementations, a result of no coverage found is returned (1656).

Although described as a particular series of operations, in some embodiments, more or fewer steps may be included in the method 1630. For example, in some implementations, rather than determining if liability coverage is generally likely (1638), multiple learning models may be executed (1636), including one or more models per type of liability payer, to determine likelihood of liability per type of liability payer. In this situation, further, the most likely liability payer(s) may be determined (1642) further based on the outcome of the machine learning models' indication (1638) of which type of liability payer(s) would be likely responsible. Other modifications of the method 1630 are possible.

Figure 17A:
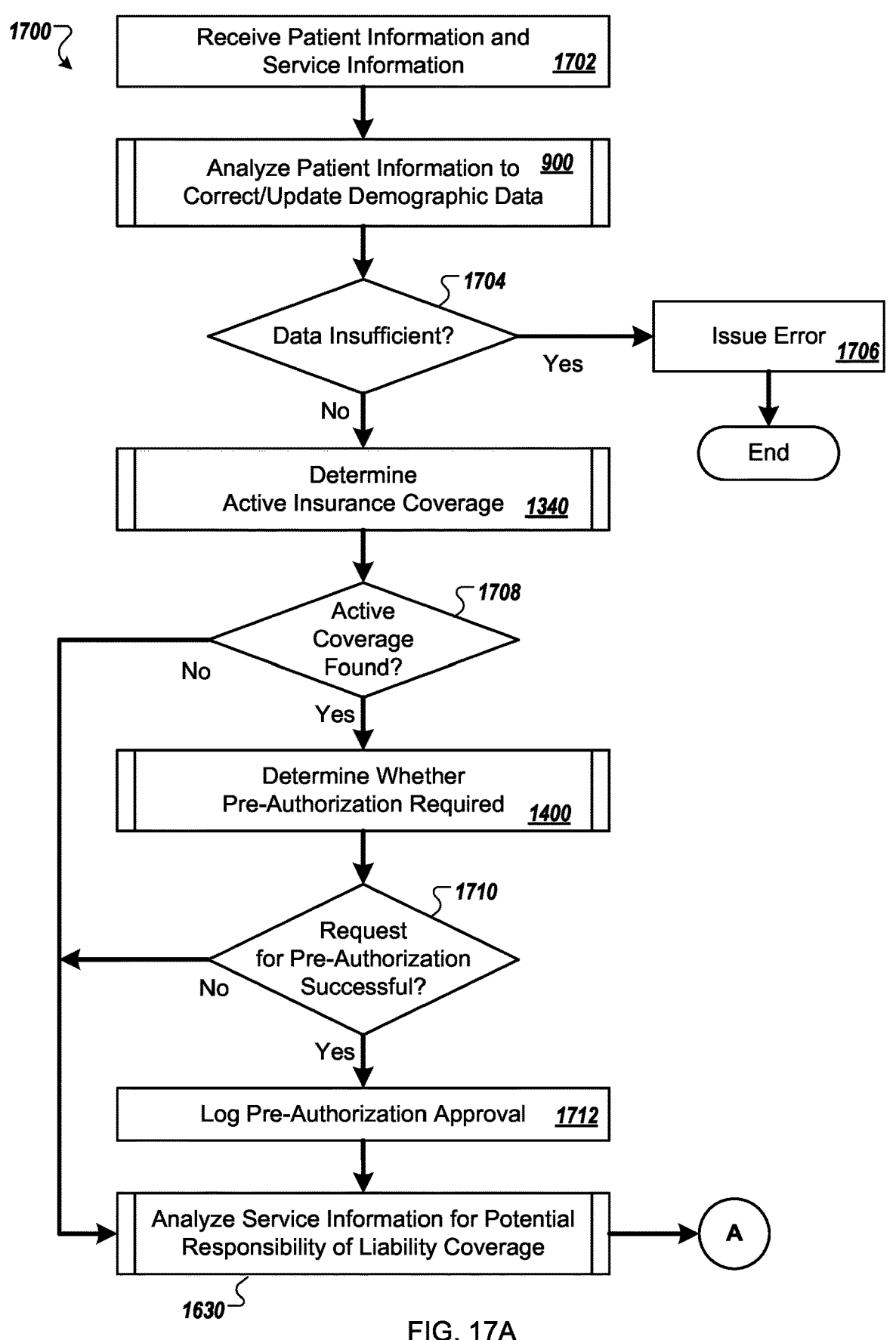
FIG. 17A through FIG. 17C illustrate a flow chart of an example method for automatically deriving payers, estimated reimbursement amounts, and estimated payment dates for medical services rendered to a patient.
Figure 17B:
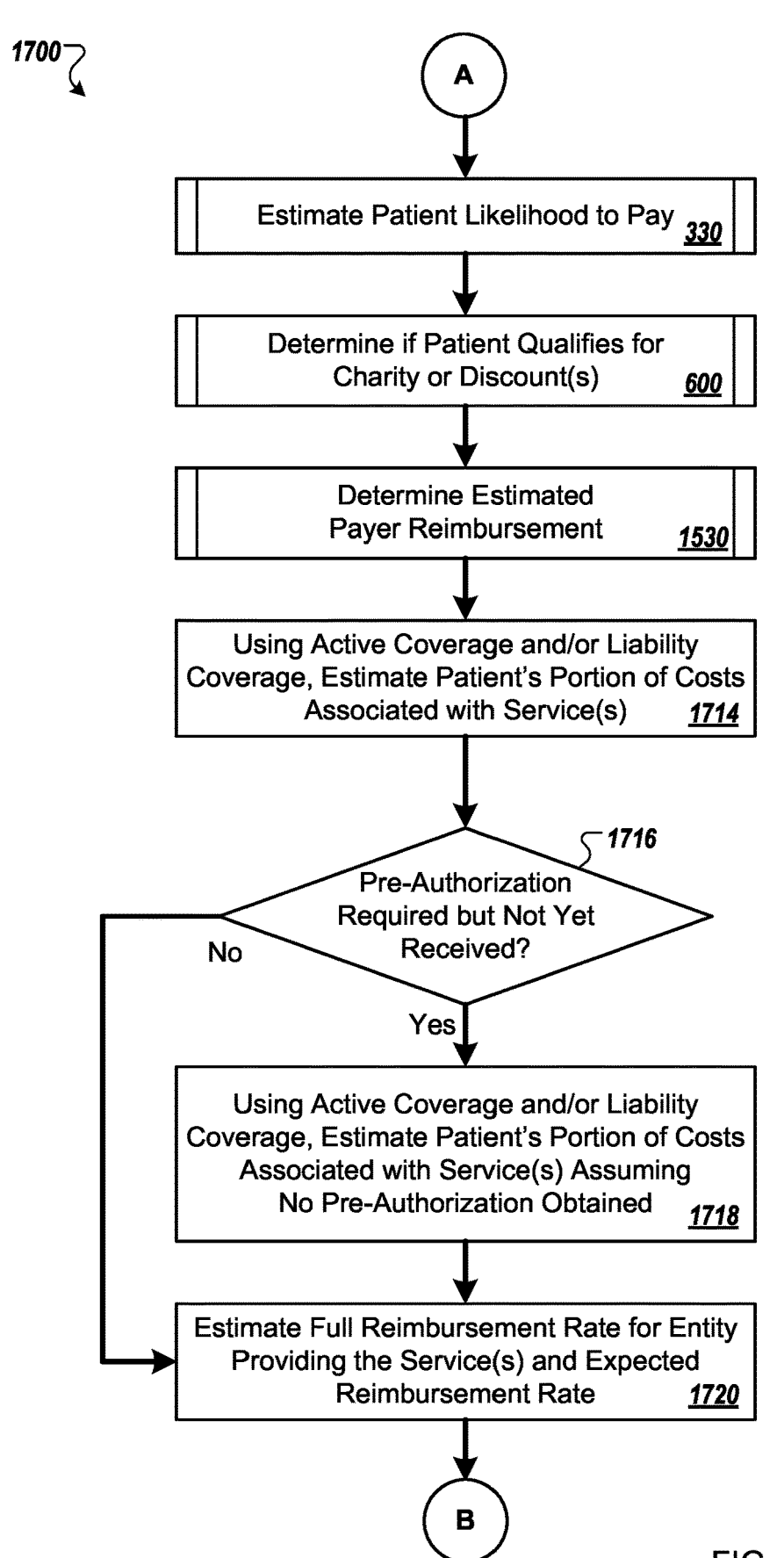
Figure 17C:
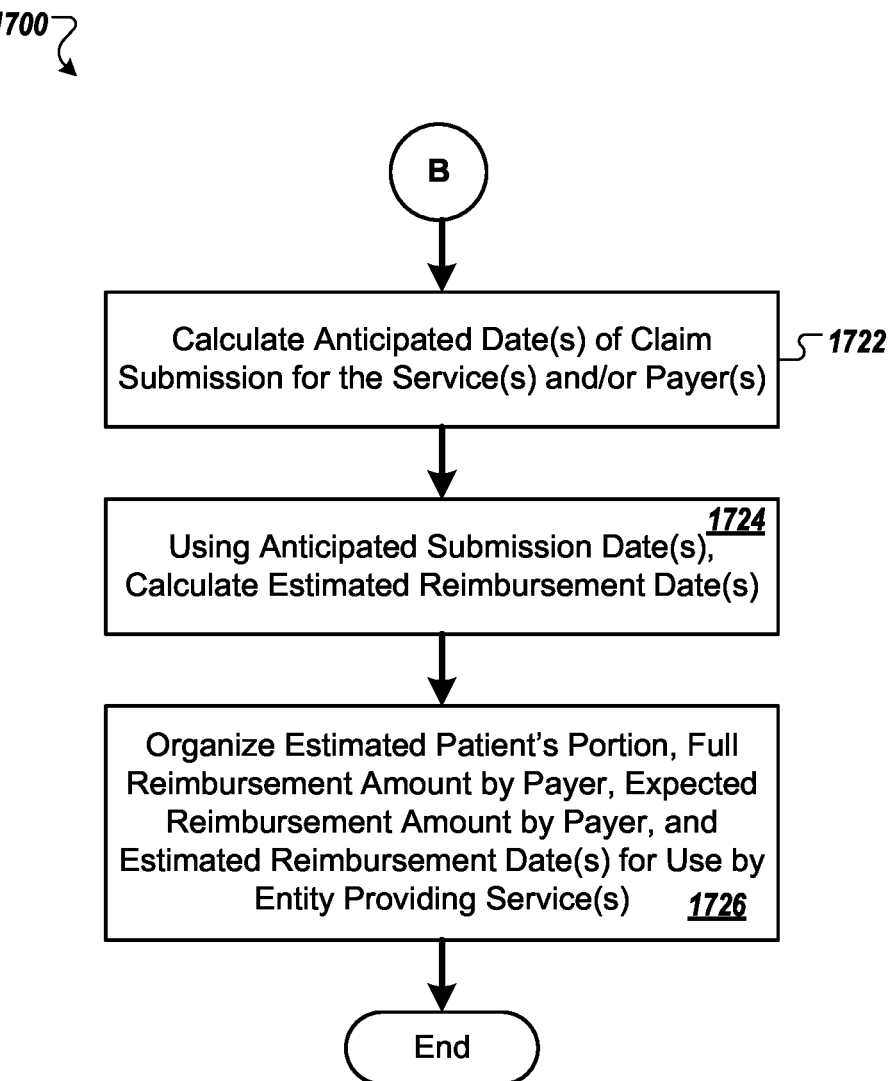

FIG. 17A through FIG. 17C illustrate a flow chart of an example method 1700 for automatically deriving payers, estimated reimbursement amounts, and estimated payment dates for medical services rendered to a patient. The method 1700, for example, may be executed as part of an automated claim processing routine on behalf of a medical provider, such as a hospital, surgical center, or other facility. The method 1700 may be performed by various engines of the predictive analytics platform 102 described in relation to FIG. 1A and FIG. 2.

In some implementations, the method begins with receiving patient information and service information (1702). The patient information and service information may be obtained and may include similar information, for example, as described in relation to the patient demographic data 116 and the procedure codes 114 of FIG. 1A. In another example, the patient information and service information may be received as part of a medical claim as described in relation to operation 152 of the method 150 of FIG. 1B.

In some implementations, the patient information is analyzed to correct and/or update the patient demographic data (see method 900 of FIG. 9).

If the data is insufficient (1704), in some implementations, an error is issued (1706).

Otherwise, if the data is sufficient (1704), in some implementations, active insurance coverage is determined (see method 1340 of FIG. 13C-1 and FIG. 13C-2).

If active coverage was not found (1708), in some implementations, the service information is analyzed for potential responsibility of liability coverage (see method 1630 of FIG. 16C-1 and FIG. 16C-2).

In some implementations, if active coverage is found (1708), it is determined whether pre-authorization is required and, if so, pre-approval is requested (see method 410 of FIG. 4B; method 1400 of FIG. 14).

If pre-authorization request is successful (1710), in some implementations, the pre-authorization approval is logged (1712). For example, pre-authorization information returned by the method 1400 of FIG. 14 may be stored in relation to the claim, such as claims data 256 of FIG. 2.

Whether or not the request for pre-authorization was not successful (1710), in some implementations, the service information is analyzed for potential responsibility of liability coverage (see method 1630 of FIG. 16C-1 and FIG. 16C-2).

Turning to FIG. 17B, in some implementations, after analyzing the service information for potential responsibility for liability coverage, the patient's likelihood to pay is estimated (see method 330 of FIG. 3D).

In some implementations, it is determined whether the patient qualifies for charity and/or other discounts (see method 600 of FIG. 6).

In some implementations, an estimated payer reimbursement is determined (see method 1530 of FIG. 15B-1 and FIG. 15B-2).

In some implementations, the patient's portion of the costs associated with the services is estimated in light of the active coverage and/or liability coverage (1714). For example, the residual balance in light of the payer portion may be determined as described in relation to operation 324 of FIG. 3A.

In some implementations, if pre-authorization is required but has not yet been received (1716), the patient's portion of the costs associated with the services is estimated in light of the active coverage and/or liability coverage assuming lack of pre-authorization (1718).

In some implementations, whether or not a pre-authorization is required, a full reimbursement rate as well as an expected reimbursement rate for the entity providing the service(s) is estimated (1720). The expected reimbursement rate, for example, may be estimated using the method 150 of FIG. 1B.

Turning to FIG. 17C, in some implementations, one or more anticipated dates of claim submission for the services and/or to each payer is calculated (1722). As described in relation to the coverage coordination analysis engine 276 of FIG. 2, for example, the portion of costs attributed to each payer and the timing for submission to each payer may be determined based upon a rules analysis.

In some implementations, using the anticipated submission date(s), estimated reimbursement date(s) are calculated (1724). The dates, for example, may be determined using the payment trends analysis engine 239 of FIG. 2. As discussed in relation to the process 700 of FIG. 7, for example, remittance by payer by timeframe may be analyzed to anticipate a number of days between claim submission and receipt of remittance.

In some implementations, the estimated patient's portion, full reimbursement amount by payer, expected reimbursement amount by payer, and estimated reimbursement date(s) are organized for use by the entity providing the service(s) (1726). In some embodiments, the information is presented in real-time to a user via a portal interface responsive to submission of initial claim processing information. Turning to FIG. 18, a screen shot of an example user interface 1800 illustrates information derived from the method 1700 via a portal interface. As illustrated, for the represented patient estimation for an identified visit on an identified date, a total reimbursement estimate 1802 is $4,302.01.

In an insurance information pane 1804, payer "Smart Healthcare" is listed, with a remaining deductible of $300,00 and an out-of-pocket remainder of $1,500.72. A copay value is listed as $0.00.

Next to the insurance information pane 1804, a charges and payments pane 1806 lists the cost for in patient stay as $12,354.38 with a patient responsibility of $450.72 and an insurance responsibility of $3,851.29. The estimated payment (e.g., total insurance responsibility plus patient responsibility) is listed as $4,302,01.

In a bottom portion of the charges and payments section 1806, a statement regarding an estimated reimbursement timeframe is presented. The statement reads, "If a claim and statement are processed today, you can expect to receive payment from the patient in four weeks and the insurance company in two weeks based on payment history for this payer or likelihood to pay statistics of the patient.

Returning to FIG. 17C, the information, in some embodiments, is issued to a requester via an API used for communicating with the method 1700 (e.g., the predictive analytics platform 102 as described in relation to FIG. 1A and FIG. 2). The information, in some embodiments, is provided in a storage region, for example in a file format or as a portion of a series of claims records, for later access by the requesting system. The format of the information, for example, may be determined at least in part based upon preferences and/or a plan type established between the requester and the predictive analytics platform.

Although described as a particular series of operations, in some embodiments, more or fewer steps may be included in the method 1700. For example, in some implementations, rather than receiving information regarding a single claim, a batch of claims may be provided to the method 1700 for processing. In further embodiments, certain steps of the method 1700 may be performed in a different order or in parallel. In some implementations, determining whether pre-authorization is required (1400) occurs while determining active insurance coverage (1340), for example by submitting a single request for subscriber verification and confirmation of whether pre-approval of the treatment code(s) is needed. Other modifications of the method 1700 are possible. Reference has been made to illustrations representing methods and systems according to implementations of this disclosure. Aspects thereof may be implemented by computer program instructions. These computer program instructions may be provided to a processor of a general-purpose computer, special purpose computer, or other programmable data processing apparatus and/or distributed processing systems having processing circuitry, such that the instructions, which execute via the processor of the computer or other programmable data processing apparatus, create means for implementing the functions/operations specified in the illustrations.

One or more processors can be utilized to implement various functions and/or algorithms described herein. Additionally, any functions and/or algorithms described herein can be performed upon one or more virtual processors. The virtual processors, for example, may be part of one or more physical computing systems such as a computer farm or a cloud drive.

Aspects of the present disclosure may be implemented by software logic, including machine readable instructions or commands for execution via processing circuitry. The software logic may also be referred to, in some examples, as machine readable code, software code, or programming instructions. The software logic, in certain embodiments, may be coded in runtime-executable commands and/or compiled as a machine-executable program or file. The software logic may be programmed in and/or compiled into a variety of coding languages or formats.

Aspects of the present disclosure may be implemented by hardware logic (where hardware logic naturally also includes any necessary signal wiring, memory elements and such), with such hardware logic able to operate without active software involvement beyond initial system configuration and any subsequent system reconfigurations (e.g., for different object schema dimensions). The hardware logic may be synthesized on a reprogrammable computing chip such as a field programmable gate array (FPGA) or other reconfigurable logic device. In addition, the hardware logic may be hard coded onto a custom microchip, such as an application-specific integrated circuit (ASIC). In other embodiments, software, stored as instructions to a non-transitory computer-readable medium such as a memory device, on-chip integrated memory unit, or other non-transitory computer-readable storage, may be used to perform at least portions of the herein described functionality.

Various aspects of the embodiments disclosed herein are performed on one or more computing devices, such as a laptop computer, tablet computer, mobile phone or other handheld computing device, or one or more servers. Such computing devices include processing circuitry embodied in one or more processors or logic chips, such as a central processing unit (CPU), graphics processing unit (GPU), field programmable gate array (FPGA), application-specific integrated circuit (ASIC), or programmable logic device (PLD). Further, the processing circuitry may be implemented as multiple processors cooperatively working in concert (e.g., in parallel) to perform the instructions of the inventive processes described above.

The process data and instructions used to perform various methods and algorithms derived herein may be stored in non-transitory (i.e., non-volatile) computer-readable medium or memory. The claimed advancements are not limited by the form of the computer-readable media on which the instructions of the inventive processes are stored. For example, the instructions may be stored on CDs, DVDs, in FLASH memory, RAM, ROM, PROM, EPROM, EEPROM, hard disk or any other information processing device with which the computing device communicates, such as a server or computer. The processing circuitry and stored instructions may enable the computing device to perform, in some examples, the method 150 of FIG. 1A, the method 300 of FIG. 3A, the method 310 of FIG. 3B, the method 320 of FIG. 3C, the method 330 of FIG. 3D, the method 400 of FIG. 4A, the method 410 of FIG. 4B, the method 500 of FIG. 5A, the method 520 of FIG. 5B, the method 600 of FIG. 6, and/or the method 900 of FIG. 9. Further, the processing circuitry and stored instructions may enable the computing device to perform, in some examples, the process 700 of FIG. 7, the process 800 of FIG. 8, the process 1000 of FIG. 10A, the process 1020 of FIG. 10B, the process 1040 of FIG. 10C, the process 1070 of FIG. 10D, the process 1080 of FIG. 10E, the process 1200 of FIG. 12A, the process 1270 of FIG. 12B, the process 1300 of FIG. 13A, the process 1320 of FIG. 13B-1, the process 1330 of FIG. 13B-2, the method 1340 of FIG. 13C-1 through FIG. 13C-2, the method 1400 of FIG. 14, the process 1500 of FIG. 15A, the method 1500 of FIG. 15B-1 through FIG. 15B-2, the process 1600 of FIG. 16A, the process 1620 of FIG. 16B, the method 1630 of FIG. 16C-1 through FIG. 16C-2, and/or the method 1700 of FIG. 17A through FIG. 17C.

These computer program instructions can direct a computing device or other programmable data processing apparatus to function in a particular manner, such that the instructions stored in the computer-readable medium produce an article of manufacture including instruction means which implement the function/operation specified in the illustrated process flows.

Embodiments of the present description rely on network communications. As can be appreciated, the network can be a public network, such as the Internet, or a private network such as a local area network (LAN) or wide area network (WAN) network, or any combination thereof and can also include PSTN or ISDN sub-networks. The network can also be wired, such as an Ethernet network, and/or can be wireless such as a cellular network including EDGE, 3G, 4G, and 5G wireless cellular systems. The wireless network can also include Wi-Fi®, Bluetooth®, Zigbee®, or another wireless form of communication. The network, in some examples, may support communications between the predictive analytics platform 102 and the data universe 104 and/or the predictive analytics platform 102 and the revenue maximizer portal 110 as discussed in relation to FIG. 1A, communications between the predictive analytics platform 102 and the clients 204, claims data sources 206, benefits information sources 208, and/or service providers 212 as discussed in relation to FIG. 2, communications between the predictive analytics platform 102 and the medical transport scheduling/dispatch platform 1002 as discussed in relation to FIG. 10A, communications between the prescription services platform 1022 and the predictive analytics platform 102 as described in relation to FIG. 10B, communications between the predictive analytics platform 102 and the application generating the GUI 1050*a*, 1050*b*, and/or 1050*c* as discussed in relation to FIG. 10C through FIG. 10E, communications between the predictive analytics platform 102 and the application generating the GUI 1102 as discussed in relation to FIG. 11, and/or communications between the predictive analytics platform and the computer-aided dispatch system 1210 and/or the predictive analytics platform 102 and the electronic patient charting service 1220 as discussed in relation to FIG. 12A. The network, in a further example, may support communications between the predictive analytics platform 102 and one or more of the computer-aided dispatch system 1210, the data universe 104 and/or the electronic patient charting service of FIG. 12A.

The computing device, in some embodiments, further includes a display controller for interfacing with a display, such as a built-in display or LCD monitor. A general purpose I/O interface of the computing device may interface with a keyboard, a hand-manipulated movement tracked I/O device (e.g., mouse, virtual reality glove, trackball, joystick, etc.), and/or touch screen panel or touch pad on or separate from the display. The display controller and display may enable presentation of the screen shots illustrated, in some examples, in FIG. 10C, FIG. 10D, FIG. 10E, FIG. 11 and/or FIG. 18.

Moreover, the present disclosure is not limited to the specific circuit elements described herein, nor is the present disclosure limited to the specific sizing and classification of these elements. For example, the skilled artisan will appreciate that the circuitry described herein may be adapted based on changes in battery sizing and chemistry or based on the requirements of the intended back-up load to be powered.

The functions and features described herein may also be executed by various distributed components of a system. For example, one or more processors may execute these system functions, where the processors are distributed across multiple components communicating in a network. The distributed components may include one or more client and server machines, which may share processing, in addition to various human interface and communication devices (e.g., display monitors, smart phones, tablets, personal digital assistants (PDAs)). The network may be a private network, such as a LAN or WAN, or may be a public network, such as the Internet. Input to the system, in some examples, may be received via direct user input and/or received remotely either in real-time or as a batch process.

Although provided for context, in other implementations, methods and logic flows described herein may be performed on modules or hardware not identical to those described. Accordingly, other implementations are within the scope that may be claimed.

In some implementations, a cloud computing environment, such as Google Cloud Platform™ or Amazon™ Web Services (AWS™), may be used perform at least portions of methods or algorithms detailed above. The processes associated with the methods described herein can be executed on a computation processor of a data center. The data center, for example, can also include an application processor that can be used as the interface with the systems described herein to receive data and output corresponding information. The cloud computing environment may also include one or more databases or other data storage, such as cloud storage and a query database. In some implementations, the cloud storage database, such as the Google™ Cloud Storage or Amazon™ Elastic File System (EFS™), may store processed and unprocessed data supplied by systems described herein. For example, the contents of portions of the data universe 104 of FIG. 1A, portions of the data repository 210 of FIG. 2, the remittance data 702, billing codes 710, revenue cycles 708 and/or recent claims 716 of FIG. 7, the historic claims data 256, billing codes 804, recent claims 818, and/or patient data 820 of FIG. 8, the claims data entry session information 1068 of FIG. 10C, the computer-aided dispatch system 1210 and/or the electronic patient charting service 1220 of FIG. 12A, the data store 1302 of FIG. 1300, the data store 1502 of FIG. 15A, and/or the data store 1602 of FIG. 16A may be maintained in a database structure.

The systems described herein may communicate with the cloud computing environment through a secure gateway. In some implementations, the secure gateway includes a database querying interface, such as the Google BigQuery™ platform or Amazon RDS™. The data querying interface, for example, may support access by the predictive analytics platform 102 and/or the revenue maximizer portal 110 of FIG. 1A, the medical transport scheduling/dispatch platform 1002 of FIG. 10A, the prescription services platform 1022 of FIG. 10B, and/or the CAD system 1210 and/or the ePCR service 1220 of FIG. 12A.

While certain embodiments have been described, these embodiments have been presented by way of example only and are not intended to limit the scope of the present disclosures. Indeed, the novel methods, apparatuses and systems described herein can be embodied in a variety of other forms; furthermore, various omissions, substitutions and changes in the form of the methods, apparatuses and systems described herein can be made without departing from the spirit of the present disclosures. The accompanying claims and their equivalents are intended to cover such forms or modifications as would fall within the scope and spirit of the present disclosures.

What is claimed is:

1. A system for generating medical claims payment data, the system comprising:

a predictive analytics platform communicatively coupled via an application programming interface (API) to an external claims processing system, wherein the predictive analytics platform excludes claim generation capabilities and comprises hardware logic and/or software logic configured to execute a process for generating a recommended pre-payment amount in real-time, the process when executed causing the hardware logic and/or software logic to:

receive, via the API from the external claims processing system, medical claim information request for a first patient prior to generation of a medical claim, the medical claim information request comprising at least one billing code and at least one item of demographic data for the first patient, access a hybrid plurality of distributed databases comprising a de-identified database comprising:

at least one patient data collection comprising a plurality of de-identified patient data records for a plurality of second patients, wherein the plurality of deidentified patient data records for the plurality of second patients comprise demographic data for the second patients, at least one health insurer data collection comprising a plurality of health insurer data records for a plurality of health insurers, and a credit agency database comprising a credit history data collection comprising at least one credit history data record for the first patient, identify a portion of the plurality of de-identified patient data records for the plurality of second patients where respective demographic data for the second patients is similar to the at least one item of demographic data for the first patient, identify, for each billing code of the at least one billing code, a health insurer payment pattern for a respective billing code based on a combination of (a) the portion of the plurality of de-identified patient data records for the plurality of second patients where respective demographic data for the second patients is similar to the at least one item of demographic data for the first patient, and (b) the plurality of health insurer data records, and identify, using machine learning analysis, a patient payment pattern for the first patient based on the at least one credit history data record and patient payment outcomes for one or more other patients among the plurality of second patients where respective demographic data for the second patients is similar to the at least one item of demographic data for the first patient, generate aggregated payment pattern data based on the health insurer payment pattern and the patient payment pattern, based on the aggregated payment pattern data, calculate a plurality of likelihoods that the first patient will pay a particular payment amount and a confidence score for each particular payment amount, the plurality of likelihoods comprising at least a first likelihood that the first patient will pay a first particular payment amount and a second likelihood that the first patient will pay a second particular payment amount, generate the recommended pre-payment amount based on the first and second likelihoods, the first and second particular payment amounts, and a threshold for the confidence score for each particular payment amount, convert the medical claim information request to a medical claim information response comprising the recommended pre-payment amount for display at a graphical user interface (GUI) of the external claims processing system, and transmit, via the API to the claims processing system, the medical claim information response comprising the recommended pre-payment amount for display at the GUI of the external claims processing system.

2. The system of claim 1, wherein identifying the health insurer payment pattern for the respective billing code comprises identifying, in the plurality of health insurer data records, remittance data for each billing code of the at least one billing code;

calculating, using the remittance data, a remittance estimate; and calculating a confidence in similarity of the remittance estimate to an actual future remittance value.

3. The system of claim 1, wherein identifying the patient payment pattern comprises matching a credit score of the first patient to a credit score range of a portion of the plurality of second patients.

4. The system of claim 1, wherein generating the aggregated payment pattern data comprises applying at least one deductible amount corresponding to a deductible level of an active health insurer plan of first patient; and automatically determining a first deductible amount of the at least one deductible amount by contacting an external computing system of an active health insurer via a network to request a current balance of a remaining maximum deductible.

5. The system of claim 1, wherein the process when executed causes the hardware logic and/or software logic to identify a liability health insurer for the first patient based on the at least one item of demographic data for the first patient.

6. The system of claim 5, wherein generating the aggregated payment pattern data comprises determining coverage coordination between the liability health insurer and a primary health insurer.

7. The system of claim 1, wherein the predictive analytics platform is configured to identify eligibility for one or more medical payment assistance programs based on the at least one item of demographic data for the first patient.

8. The system of claim 7, wherein the process when executed causes the hardware logic and/or software logic to initiate enrollment of the first patient in the one or more medical payment assistance programs.

9. The system of claim 1, further comprising:

a procedure trends analysis engine comprising hardware logic and/or software logic configured to analyze a plurality of historic claims related to the plurality of second patients to identify a plurality of sets of commonly paired procedures, wherein claim submission of a first procedure of the plurality of sets of commonly paired procedures precedes claim submission of a second procedure of the plurality of sets of commonly paired procedures by up to a threshold period of time, for each set of commonly paired procedures, identifying comprises determining that the first procedure is followed by the second procedure for at least a threshold percentage of a portion of the plurality of historic claims including the first procedure and identify, within the plurality of sets of commonly paired procedures, a likelihood of the second procedure following the first procedure based on a set of demographic groups.

10. The system of claim 1, wherein the process when executed causes the hardware logic and/or software logic to analyze the at least one item of demographic data in view of identification criteria to identify insufficiency of the demographic data, and, based on the insufficiency of the demographic data, locate patient information regarding the first patient in at least one additional data source to supplement the at least one item of demographic data.

11. The system of claim 10, wherein the process when executed causes the hardware logic and/or software logic to identify at least one of a contradiction or an ambiguity in patient information by comparing the at least one item of demographic data to known demographic data for the first patient, and locate patient information regarding the first patient in at least one additional data source resolve the at least one of the contradiction or the ambiguity in the at least one item of demographic data.

12. The system of claim 10, wherein the insufficiency of the demographic data comprises one or more inconsistent elements in an address, spelling of name, and/or date of birth for the first patient.

13. The system of claim 12, wherein supplementing the at least one item of demographic data comprises presenting the demographic data for acceptance by a user.

14. The system of claim 1, wherein the predictive analytics platform is communicatively coupled with one or more of a computer-aided dispatch (CAD) and an electronic patient care record (ePCR) application hosted by an ePCR system and configured to:

receive initial patient demographics for a patient from the CAD and/or the ePCR application;

identify supplemental patient demographics based on the initial patient demographics;

identify insurance coverages for the patient based on the supplemental patient demographics;

provide the supplemental patient demographics and the insurance coverages to the CAD and/or the ePCR application;

receive the initial patient demographics for the patient from the CAD; and provide the supplemental patient demographics and insurance coverages to the ePCR application.

15. The system of claim 1, wherein at least a portion of input is received through the API accessed by a source of input data.

16. The system of claim 1, wherein the medical claim information request comprises a JavaScript Object Notation (JSON) or Extensible Markup Language (XML) format.

17. The system of claim 1, wherein the at least one credit history data record comprises past payment history, personal or family income and credit history information, medical credit history, a medical spending plan available, and/or a deductible amount remaining for the first patient.

18. The system of claim 1, wherein the process when executed causes the hardware logic and/or software logic configured to apply the at least one item of demographic data for the first patient to identify at least one health insurer for the first patient.

19. The system of claim 18, wherein identifying the at least one health insurer comprises automatically verifying, with an external computing system of the at least one health insurer via a network, active coverage of the first patient; and contacting an external computing system of each health insurer of most likely health insurers, via a network, to query existence of active coverage of the first patient with a respective health insurer.

20. The system of claim 18, wherein identifying the at least one health insurer comprises determining, for each billing code of the at least one billing code, a pre-authorization status corresponding to the respective billing code; and wherein determining the pre-authorization status comprises analyzing at least a portion of i) the plurality of health insurer data records and/or ii) the plurality of de-identified patient data records using the respective billing code to identify evidence of authorization requests from one or more of the plurality of second patients.

21. The system of claim 20, wherein analyzing i) the plurality of health insurer data records and/or ii) the plurality of de-identified patient data records comprises determining a historic pattern of coverage declinations associated with the respective billing code indicative of likelihood of a pre-authorization requirement by the at least one health insurer.

22. The system of claim 20, further comprising a pre-approval authorization engine comprising hardware and/or software logic configured to initiate an authorization request submission with a first health insurer of the at least one health insurer on behalf of the first patient.

23. The system of claim 20, wherein determining the pre-authorization status comprises automatically issuing, to an external computing system of the at least one health insurer via a network, a request to determine authorization status of a service corresponding to the respective billing code on behalf of the first patient.

24. The system of claim 1, wherein the at least one health insurer data collection comprising the plurality of health insurer data records for the plurality of health insurers comprises at least one health insurer for the first patient.

25. The system of claim 1, wherein the medical claim information request comprises at least one health insurer plan.

26. The system of claim 25, wherein identifying the health insurer payment pattern for the respective billing code comprises identifying a portion of the plurality of de-identified patient data records associated with one or more health insurer plans, wherein the one or more health insurer plans are the same as or similar to the at least one health insurer plan of the first patient.

27. The system of claim 26, wherein the portion of the plurality of de-identified patient data records associated with the one or more health insurer plans are dated within one year of receiving the medical claim information request.

28. The system of claim 26, wherein the one or more health insurer plans that are the same as or similar to the at least one health insurer plan of the first patient are identified by performing machine learning analysis on the plurality of health insurer data records.

29. The system of claim 1, wherein identifying the health insurer payment pattern for the respective billing code comprises identifying a portion of the plurality of de-identified patient data records associated with one or more billing codes similar to the respective billing code for the first patient, wherein the one or more billing codes similar to the respective billing code are identified by filtering a billing code repository by a closeness in number and/or natural language processing of a description associated with respective billing code.

30. The system of claim 1, wherein identifying the patient payment pattern comprises identifying a portion of the plurality of de-identified patient data records for a plurality of patients similar to the first patient, the plurality of patients similar to the first patient are identified based on one or more similarities in demographic data, disability status, responsible party status, a type of medical service, a range of cost to patient.

31. The system of claim 1, further comprising a patient matching engine for identifying patients similar to the first patient, wherein the patient matching engine identifies patients similar to the first patient in the at least one patient data collection and qualifies respective patient identified to be similar to the first patient with a closeness rating or percentage similarity.

32. The system of claim 1, wherein the predictive analytics platform executes the process for generating the recommended pre-payment amount in real-time during pre-admittance of the first patient.

33. The system of claim 1, wherein the predictive analytics platform executes the process for generating the recommended pre-payment amount in real-time during a visit by the first patient to a medical provider.

34. The system of claim 1, wherein the process when executed causes the hardware logic and/or software logic to identify one or more of a patient health savings account, a flexible spending account, and an available credit balance on a medical spending credit card for the first patient.

35. The system of claim 1, wherein the respective demographic data for the second patients that is similar to the at least one item of demographic data for the first patient comprises at least one of an age range, a gender, an employment status, an income level, and a geographic region.

36. The system of claim 35, wherein the at least one of the age range, the gender, the employment status, the income level, and the geographic region is qualified as similar to the at least one item of demographic data for the first patient according to a closeness rating or a percentage similarity.

\* \* \* \* \*